United States Patent
Carluer et al.

(10) Patent No.: US 12,220,418 B2
(45) Date of Patent: *Feb. 11, 2025

(54) OLANZAPINE COMPOSITIONS AND METHODS OF USE

(71) Applicant: MEDINCELL S.A., Jacou (FR)

(72) Inventors: Mélodie Carluer, Jacou (FR); Maria Ferrand, Aniane (FR); Irina Cherniakov, Rehovot (IL); Anna Elgart Valitsky, Kfar-Saba (IL)

(73) Assignee: MEDINCELL S.A., Jacou (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/736,965

(22) Filed: Jun. 7, 2024

(65) Prior Publication Data

US 2024/0325408 A1 Oct. 3, 2024

Related U.S. Application Data

(63) Continuation of application No. 18/409,158, filed on Jan. 10, 2024.

(60) Provisional application No. 63/516,283, filed on Jul. 28, 2023, provisional application No. 63/479,267, filed on Jan. 10, 2023.

(51) Int. Cl.
| | |
|---|---|
| *A61K 31/5513* | (2006.01) |
| *A61K 9/00* | (2006.01) |
| *A61K 47/20* | (2006.01) |
| *A61K 47/22* | (2006.01) |
| *A61K 47/34* | (2017.01) |
| *A61P 25/18* | (2006.01) |

(52) U.S. Cl.
CPC ........ *A61K 31/5513* (2013.01); *A61K 9/0019* (2013.01); *A61K 47/20* (2013.01); *A61K 47/22* (2013.01); *A61K 47/34* (2013.01); *A61P 25/18* (2018.01)

(58) Field of Classification Search
CPC .. A61K 31/5513; A61K 9/0019; A61K 47/20; A61K 47/22; A61K 47/34; A61P 25/18
See application file for complete search history.

(56) References Cited

U.S. PATENT DOCUMENTS

| | | |
|---|---|---|
| 5,229,382 A | 7/1993 | Chakrabarti et al. |
| 5,736,541 A | 4/1998 | Bunnell et al. |
| 7,323,459 B2 | 1/2008 | Dolitzky et al. |
| 2020/0179518 A1 | 6/2020 | Roberge et al. |

FOREIGN PATENT DOCUMENTS

WO  WO 2012/090070 A2  7/2012

OTHER PUBLICATIONS

"Mental Health and Wellness Information," New York State Office of Mental Health, 2014, URL: <https://www.omh.ny.gov/omhweb/resources/publications/>.

(Continued)

*Primary Examiner* — Carlos A Azpuru
(74) *Attorney, Agent, or Firm* — Birch, Stewart, Kolasch & Birch, LLP

(57) ABSTRACT

The disclosure provides pharmaceutical compositions for subcutaneous administration comprising olanzapine, and organic solvent, and a triblock copolymer, and a diblock copolymer, as well as methods of treating psychiatric diseases and disorders using such compositions.

24 Claims, 11 Drawing Sheets

(56) References Cited

OTHER PUBLICATIONS

Barnes et al., "Long Term Depot Antipsychotics—A Risk-Benefit Assessment," Drug Safety, vol. 10, No. 6, 1994, pp. 464-479.

Carbon et al., "Clinical predictors of therapeutic response to antipsychotics in schizophrenia," Dialogues in Clinical Neuroscience, vol. 16, No. 4, 2014, pp. 505-524.

Detke et al., "Post-injection delirium/sedation syndrome in patients with schizophrenia treated with olanzapine long-acting injection,I: analysis of cases," BMC Psychiatry, vol. 10, No. 43, 2010, pp. 1-10.

European Pharmacopoeia 2.9.34. Method 1, downloaded Nov. 14, 2021, URL: <https://www.drugfuture.com/Pharmacopoeia/EP7/DATA/20934E.PDF>.

Gidal et al., "The application of half-life in clinical decision making: Comparison of the pharmacokinetics of extended-release topiramate (USL255) and immediate-release topiramate," Epilepsy Research, vol. 129, 2017, pp. 26-32.

Guy, "ECDEU Assessment Manual for Psychopharmacology (revised)," U.S. Department of Health, Education, and Welfare: Public Health Service, 1976, 25 pages total.

Heres et al., "Pharmacokinetics of olanzapine long-acting injection; the clinical perspective," International Clinical Psychopharmacology, vol. 29, No. 6, 2014, pp. 299-312.

Hughes, "Estimation of the impact of noncompliance on pharmacokinetics: an analysis of the influence of dosing regimens," British Journal of Clinical Pharmacology, vol. 65, No. 6, 2008, pp. 871-878.

Kane et al., "Non-adherence to medication in patients with psychotic disorders: epidemiology, contributing factors and management strategies," World Psychiatry, vol. 12, No. 3, 2013, pp. 216-226.

Kay et al., "The Positive and Negative Syndrome Scale (PANSS) for Schizophrenia," Schizophrenia Bulletin, vol. 13, No. 2, 1987, pp. 261-276.

Keith et al., "Partial Compliance and Patient Consequences in Schizophrenia: Our Patients Can Do Better," Journal of Clinical Psychiatry, vol. 64, No. 11, 2003, pp. 1308-1315.

Kishimoto et al., "Long-acting injectable versus oral antipsychotics for the maintenance treatment of schizophrenia: a systematic review and comparative meta-analysis of randomised, cohort, and pre-post studies," Lancet Psychiatry, vol. 8, 2021, pp. 387-404.

Krause et al., "Estimation of Attainment of Steady-State Conditions for Compounds With a Long Half-Life," Journal of Clinical Pharmacology, vol. 61, No. 1, 2021, pp. 82-89.

Lieberman et al., "Effectiveness of Antipsychotic Drugs in Patients with Chronic Schizophrenia," New England Journal of Medicine, vol. 353, No. 12, 2005, pp. 1209-1223.

Martin et al., "Factor structure of the Schizophrenia Quality of Life Scale Revision 4 (SQLS-R4)," Psychology, Health & Medicine, vol. 12, No. 2, 2007, pp. 126-134.

Morosini et al., "Development, reliability and acceptability of a new version of the DSM-IV Social and Occupational Functioning Assessment Scale (SOFAS) to assess routine social functioning," Acta Psychiatrica Scandinavica, vol. 101, 2000, pp. 323-329.

Rabin et al., "EQ-5D: a measure of health status from the EuroQol Group," Annals of Medicine, vol. 33, 2001, pp. 337-343.

Rainer, "Risperidone long-acting injection: a review of its long term safety and efficacy," Neuropsychiatric Disease and Treatment, vol. 4, No. 5, 2008, pp. 919-927.

Stefan et al., "An Atlas of Schizophrenia;" The Parthenon Publishing Group, 2002, 90 pages total.

Steinert et al., "PGI-I (Patient's Global Impression) as an Outcome and Quality Indicator of Psychiatric In-patient Treatment: Results and Concordance with Doctor's Assessments," Psychiatrische Praxis, vol. 37, 2010, pp. 343-349, with an English abstract.

The EuroQol Group, "EuroQol*—a new facility for the measurement of health-related quality of life," Health Policy, vol. 16, 1990, pp. 199-208.

Walburn et al., "Systematic review of patient and nurse attitudes to depot antipsychotic medication," British Journal of Psychiatry, vol. 179, 2001, pp. 300-307.

Wilkinson et al., "Self-report quality of life measure for people with schizophrenia: the SQLS;" British Journal of Psychiatry, vol. 177, 2000, pp. 42-46.

International Search Report for International Application No. PCT/EP2024/050429, dated Apr. 2, 2024.

Roberge et al., "BEPO®: Bioresorbable diblock mPEG-PDLLA and triblock PDLLA-PEG-PDLLA based in situ forming depots with flexible drug delivery kinetics modulation," Journal of Controlled Release, vol. 319, 2020, pp. 416-427.

OLANZAPINE COMPOSITIONS AND METHODS OF USE

CROSS-REFERENCE TO RELATED APPLICATIONS

This application is a Continuation of copending application Ser. No. 18/409,158, filed on Jan. 10, 2024, which claims priority under 35 U.S.C. § 119(e) to U.S. Provisional Application No. 63/479,267, filed on Jan. 10, 2023, and U.S. Provisional Application No. 63/516,283, filed on Jul. 28, 2023, all of which are hereby expressly incorporated by reference into the present application.

TECHNICAL FIELD

The disclosure relates to pharmaceutical compositions for subcutaneous administration comprising olanzapine, and organic solvent, and a triblock copolymer and a diblock copolymer, as well as methods of treating psychiatric diseases and disorders responsive to olanzapine using such compositions.

BACKGROUND

Schizophrenia is a severely debilitating psychotic disorder characterized by positive symptoms (e.g., delusions, hallucinations, and grossly disorganized behavior) and negative symptoms (e.g., affective flattening, alogia, and avolition) (New York State Office of Mental Health, 2019, Stefan et al, 2002).

The worldwide lifetime morbidity risk of the disorder is approximately 1% across diverse geographic, cultural, and socio economic regions. Since, in most patients, the disease follows a chronic course with long lasting impairment, long term treatment with antipsychotic agents is usually required.

Noncompliance and high discontinuation rates are particularly problematic in patients with schizophrenia. Premature discontinuation of antipsychotic drug therapy is a common phenomenon; in the Clinical Antipsychotic Trials of Intervention Effectiveness (CATIE) study, 74% of patients discontinued their drug within 18 months due to either poor tolerability or lack of efficacy, patient choice (ie, nonadherence/study withdrawal) or for investigator reasons (Lieberman et al, 2005). Even among those who do not explicitly discontinue drug therapy, nonadherence to long term oral medication regimes is one of the most significant therapeutic issues in the therapy of schizophrenia and related disorders (Kane et al, 2013). As a result, many of these patients do not experience the full benefit of antipsychotic drug therapy and suffer frequent relapses or exacerbations that require rehospitalization (Carbon and Correll, 2014), often in the context of psychiatric emergency (Rainer, 2008).

Thus, the availability of a long-acting injectable (LAI) antipsychotic agent may increase compliance in patients with schizophrenia (Barnes and Curson, 1994, Hughes, 2008, Keith and Kane, 2003, Kishimoto et al, 2021, Walburn et al, 2001) and have been shown to significantly reduce relapse and rehospitalization as well as improve many clinically relevant outcomes significantly more than oral antipsychotics in randomized trials, cohort studies and mirror-image studies.

Olanzapine is a well characterized and commonly prescribed atypical antipsychotic drug that has been approved for the treatment of schizophrenia and is available in oral and im formulations. Olanzapine is currently marketed in the United States (US) as ZYPREXA tablets (2.5, 5, 7.5, 10, 15, and 20 mg); ZYPREXA INTRAMUSCULAR for rapid acting injection (10 mg/mL) and as ZYPREXA ZYDIS® orally disintegrating tablets (5, 10, 15, and 20 mg) (ZYPREXA, ZYPREXA ZYDIS, ZYPREXA INTRAMUSCULAR United States Prescribing Information [USPI] 2021). ZYPREXA RELPREVV®, an extended release olanzapine pamoate powder and solvent for suspension, is administered by deep intramuscular gluteal injection either every 2 weeks (150, 210, and 300 mg) or every 4 weeks (300 and 405 mg), depending on the target oral olanzapine dose (10, 15, or 20 mg/day). ZYPREXA RELPREVV® (ZYPREXA RELPREVV® PI, 2021) is currently approved and marketed in the US for the treatment of schizophrenia; however, it is only available through a restricted distribution program. ZypAdhera® is a further olanzapine pamoate product which has the same composition as ZYPREXA RELPREVV®.

ZYPREXA RELPREVV® must be administered in a registered healthcare facility with ready access to emergency response services. After each treatment, a healthcare professional must continuously observe the patient at the healthcare facility for at least 3 hours and must confirm that the patient is alert, oriented, and absent of any signs and symptoms of Post-injection Delirium/Sedation Syndrome (PDSS), which can occur as a consequence of the route of administration, prior to being released. PDSS is characterized by heavy sedation (possibly including coma) and/or delirium after injection. During PDSS events, patients show higher plasma concentrations of olanzapine, leading to the assumption that unintended partial intravascular injection or blood vessel injury during the injection induces an acceleration of dissolution of the salt which may be causative of PDSS. See, e.g., Heres S, Kraemer S, Bergstrom R F, Detke H C. *Pharmacokinetics of olanzapine long-acting injection: the clinical perspective.* Int Clin Psychopharmacol. 2014.

All patients must be vigilant for symptoms of PDSS and be able to obtain emergency medical assistance in a facility capable of medical monitoring and resuscitation. Because of the extensive and inconvenient precautions required for safe use of ZYPREXA RELPREVV®, the product is rarely used in routine clinical practice. As a consequence, the options available to psychiatrists for clinical management of schizophrenia are curtailed. Alternative treatment options are needed.

WO2012090070 describes pharmaceutical formulations comprising biodegradable PLA-PEG-PLA triblock and mPEG-PLA diblock polymers, which are useful for the delivery of a variety of actives.

SUMMARY

In some aspects, the disclosure provides a pharmaceutical composition for administration by subcutaneous injection wherein the composition comprises:
  20%-45% (w/w) of olanzapine;
  35%-65% (w/w) of an organic solvent comprising dimethyl sulfoxide, N-methyl-2-pyrrolidinone (NMP), or a combination thereof;
  a diblock copolymer comprising polylactic acid and polyethylene glycol and having a number average molecular weight of 6 to 15 kg/mol and comprising 70%-90% by weight (w/w) polylactic acid; and
  a triblock copolymer comprising polylactic acid and polyethylene glycol and having a number average molecular weight of 6 to 19 kg/mol and comprising 80%-90% by weight (w/w) polylactic acid;

and wherein the diblock copolymer and triblock copolymer together comprise 10%-25% by weight (w/w) of the composition.

In other aspects, the disclosure provides a pharmaceutical compositions for administration by subcutaneous injection wherein the composition consists essentially of:
20%-45% (w/w) of olanzapine;
35%-65% (w/w) of an organic solvent comprising dimethyl sulfoxide, N-methyl-2-pyrrolidinone (NMP), or a combination thereof;
a diblock copolymer comprising polylactic acid and polyethylene glycol and having a number average molecular weight of 6 to 15 kg/mol and comprising 70%-90% by weight (w/w) polylactic acid; and
a triblock copolymer comprising polylactic acid and polyethylene glycol and having a number average molecular weight of 6 to 19 kg/mol and comprising 80%-90% by weight (w/w) polylactic acid;
and wherein the diblock copolymer and triblock copolymer together comprise 10%-25% by weight (w/w) of the composition.

In some aspects, the disclosure provides a pharmaceutical composition for administration by subcutaneous injection wherein the composition consists of:
20%-45% (w/w) of olanzapine;
35%-65% (w/w) of an organic solvent comprising dimethyl sulfoxide, N-methyl-2-pyrrolidinone (NMP), or a combination thereof;
a diblock copolymer comprising polylactic acid and polyethylene glycol and having a number average molecular weight of 6 to 15 kg/mol and comprising 70%-90% by weight (w/w) polylactic acid; and
a triblock copolymer comprising polylactic acid and polyethylene glycol and having a number average molecular weight of 6 to 19 kg/mol and comprising 80%-90% by weight (w/w) polylactic acid;
and wherein the diblock copolymer and triblock copolymer together comprise 10%-25% by weight (w/w) of the composition.

The above-mentioned pharmaceutical compositions enable safe and effective treatment of schizophrenia, schizoaffective disorder, bipolar disorder, or depression in a patient with a convenient once per month dosing regimen. The composition can be administered to a patient and provides an olanzapine plasma $C_{max}$ of less than 100 ng/mL. Without being bound by theory, it is understood that when the olanzapine plasma $C_{max}$ is below 100 ng/mL, treatment is clinically effective and PDSS can be avoided. Thus the compositions of the invention can be administered on a monthly basis with minimal to no monitoring or intervention from a medical practitioner during the intervening period.

Methods of preparing the compositions of the disclosure are also provided, as are methods of administering olanzapine to a patient using compositions of the disclosure, and methods of treating a disease or disorder that is schizophrenia, schizoaffective disorder, bipolar disorder, or depression in a patient using compositions of the disclosure.

The disclosure also provides kits comprising:
a container containing 318 mg-950 mg, optionally 550 mg-950 mg, optionally 450 mg-800 mg of olanzapine; and
a container containing a 0.73-2.5 grams, optionally 1.3-2.5 grams, optionally 0.9-2.1 grams of a mixture of an organic solvent that is dimethyl sulfoxide (DMSO), N-methyl-2-pyrrolidinone (NMP), or a combination thereof, a diblock copolymer comprising polylactic acid and polyethylene glycol and having a number average molecular weight of 6 to 15 kg/mol and comprising 70%-90% by weight (w/w) polylactic acid, and a triblock copolymer comprising polylactic acid and polyethylene glycol and having a number average molecular weight of 6 to 19 kg/mol and comprising 80%-90% by weight (w/w) polylactic acid.

Methods of treating a patient using the kits of the disclosure are also provided.

Also provided are methods of switching a patient from a daily oral olanzapine therapy to a therapy comprising once per month administration of a composition of the disclosure, and methods of switching a patient from a long acting intramuscular injectable olanzapine formulation to a composition of the disclosure.

Also provided are pharmaceutical compositions as defined above for use in medicine.

Also provided are pharmaceutical compositions as defined above for use in a method as defined above.

Figure 1:
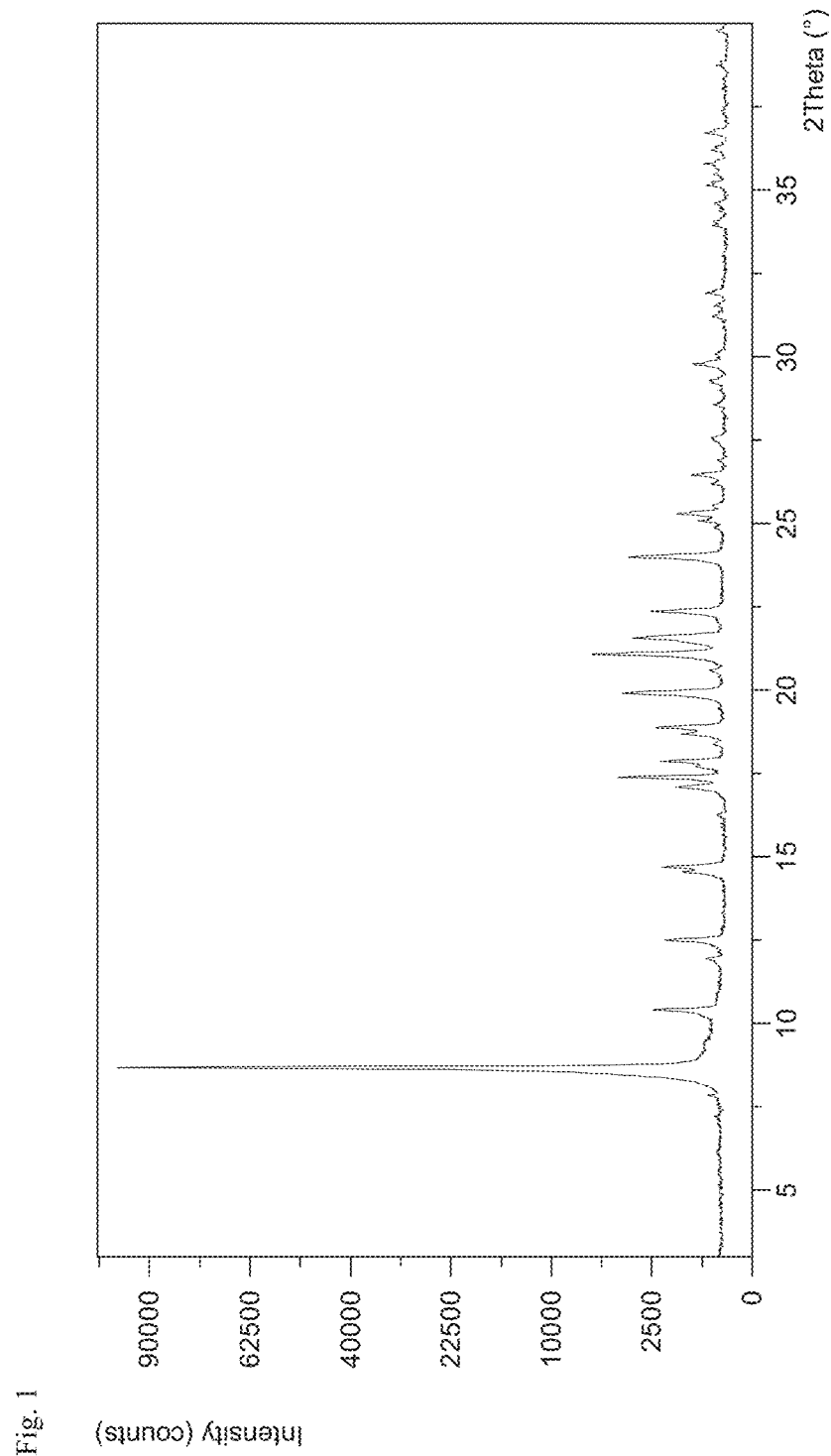
FIG. 1 shows an X-ray diffraction analysis (XRD) profile of olanzapine Form II.

Patients entering the study who have not previously received oral olanzapine will receive 2 oral doses of olanzapine for 2 consecutive days during the screening period (the second dose should be administered at least 24 hours prior to randomization) to assess patient tolerability (oral olanzapine 10 mg/day or higher [but not exceeding 20 mg/day] per investigator decision). Patients who received olanzapine within the last year will not be required to receive the 2 doses of oral treatment. The investigator will verify the previous use, tolerability, and duration of olanzapine treatment to assure prior tolerability. In order to maintain the blind in Period 1, all patients will be randomized again between Period 1 and Period 2; patients who were previously assigned to the active treatment groups will retain their Period 1 treatment assignment (the re-randomization of patients in the Formulation 1 groups is being done only to maintain blinding of Period 1, and de facto is a deterministic assignment and not randomization), and patients who were previously assigned to the placebo group will be randomized to one of the active treatment groups in a 1:1:1 ratio. Revealing of the treatment assignment in Period 2 will be performed only after completion and reporting of the relevant study procedures related to assessment of efficacy and safety endpoints in Period 1, on a patient-by-patient basis. The revealing of the Period 2 treatment assignment will be performed between week 8 and week 12 by the sponsor or delegates according to a process predefined in the relevant study plans, provided that all requirements stipulated in this process were met. Therefore, the dosing at week 8, although assigned to Period 2, will be handled in a blinded manner by all parties, similarly to the dosing in Period 1. qlm=once monthly; R=randomization.

Figure 10:
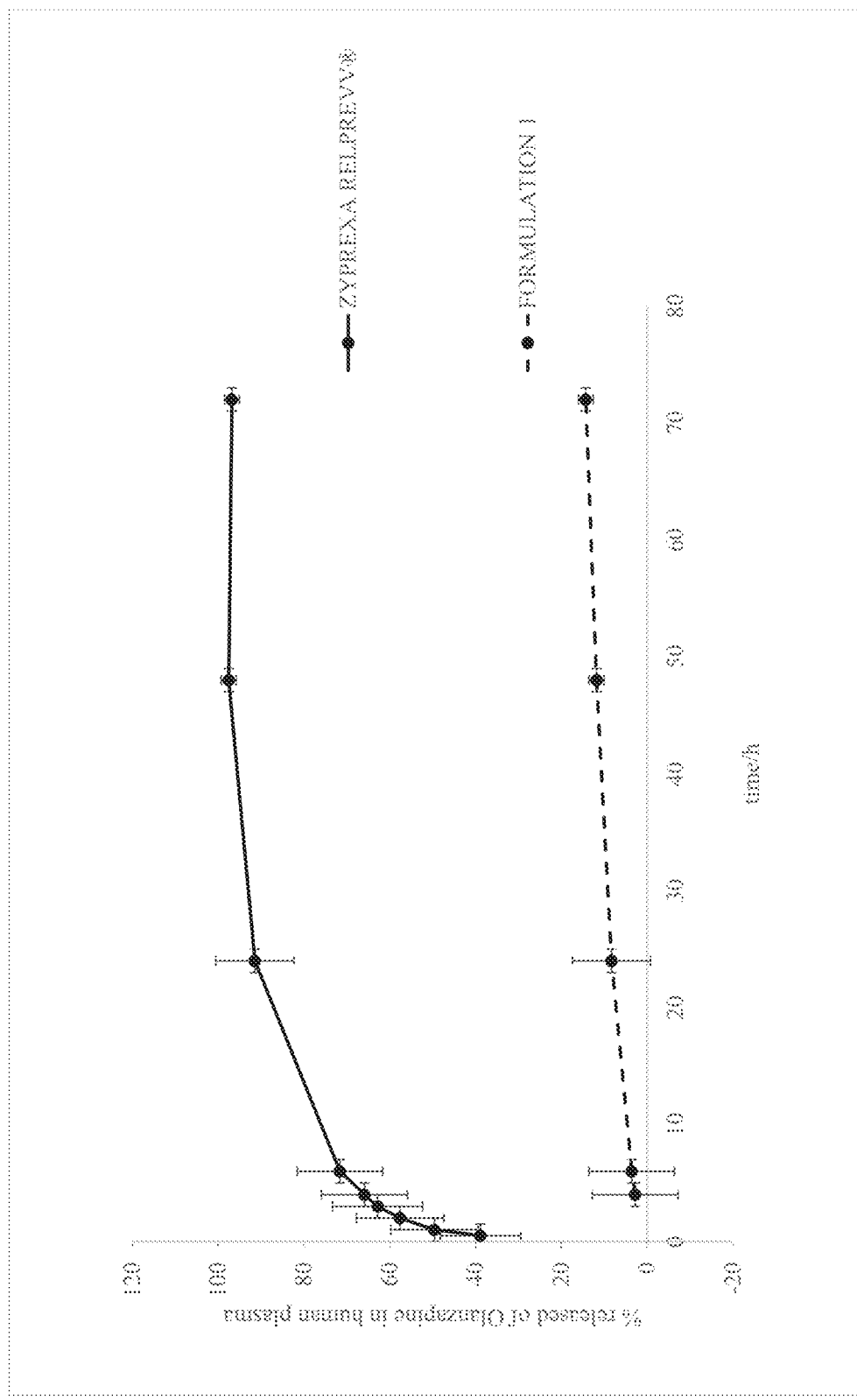

FIG. 10 shows in vitro release results of Formulation 1 and Zyprexa Relprevv® in human plasma at 37° C. See Example 7.

DETAILED DESCRIPTION OF ILLUSTRATIVE EMBODIMENTS

Unless otherwise defined, all technical and scientific terms used herein have the same meaning as commonly understood by one of ordinary skill in the art to which this disclosure pertains. The terminology used in the description is for describing particular embodiments only and is not intended to be limiting of the disclosure.

Where a range of values is provided, it is understood that the upper limit of the range, the lower limit of the range, and each intervening value between the upper and lower limit of that range is encompassed within the disclosure.

As used herein, the term "about" refers to the indicated value and any number within the range+10% of the indicated value. Thus, for example, the term "about 10%" refers to any value within the range of 9 to 11, inclusive.

The articles "a" and "an" as used herein refer to one or to more than one (e.g., to at least one) of the grammatical object of the article unless the context clearly indicates otherwise. For example, "a composition" means one composition or more than one composition.

The term "olanzapine", refers to the compound having the chemical name 2-methyl-4-(4-methyl-1-piperazinyl)-10H-thieno[2,3-b] [1,5]benzodiazepine and the chemical structure:

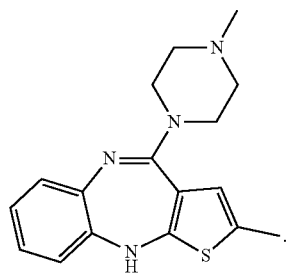 [SMILES: Cc1cc2c(s1)Nc1ccccc1N=C2N1CCN(C)CC1]

Pharmaceutically acceptable salts of olanzapine are also within the scope of the disclosure.

U.S. Pat. Nos. 5,229,382 and 5,736,541 describe olanzapine Form I and Form II, respectively. U.S. Pat. No. 7,323,459 describes olanzapine crystalline Forms H, G, Y, X, K, S, Q, Z, and J. As a free base or salt, e.g., hydrochloride or pamoate, olanzapine is an active pharmaceutical ingredient (API) of medications used in the treatment of schizophrenia and other neuropsychiatric diseases and disorders.

"Pharmaceutically acceptable" means approved or approvable by a regulatory agency of the Federal or a state government of the United States or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, pamoic acid, propionic acid, hexanoic acid, cyclopentanepropionic acid, glycolic acid, pyruvic acid, lactic acid, malonic acid, succinic acid, malic acid, maleic acid, oxalic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith.

The term "alkyl," when used alone or as part of a substituent group, refers to a straight- or branched-chain saturated hydrocarbon group having from 1 to 6 carbons atoms ("$C_1$-$C_6$"), in the group. Examples of alkyl groups include methyl, ethyl, n-propyl, iso-propyl, n-butyl, t-butyl, iso-butyl, sec-butyl, n-pentyl, n-hexyl, and the like. When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The terms "a patient" or "the patient" is used throughout the specification to describe a human being to whom treatment, including prophylactic treatment, with the compositions according to the present disclosure is provided. As used herein, the terms "a patient" or "the patient" also refers to either an individual human being, or where the context permits, a population of human beings. Thus, in some embodiments, the patient is an individual human being. In other embodiments, the patient is a population of human beings.

The terms "a subject" or "the subject" as used herein refers to a human being to whom the compositions according to the present disclosure is administered.

"Treating" or "treatment" of any disease or disorder refers, in one embodiment, to ameliorating the disease or disorder (e.g., arresting or reducing the development of the disease or at least one of the clinical symptoms thereof). In another embodiment "treating" or "treatment" refers to ameliorating at least one physical or psychological parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder or its symptoms. In some embodiments, "treating" or "treatment" encompasses maintenance therapy, i.e., treatment aimed at maintaining a patient's improved condition by reducing or eliminating adverse changes in the patient's clinical symptoms, or physical or psychological parameters.

The term "effective" as used to describe a treatment, refers to a treatment that is efficacious, i.e., that produces the desired result, including, but not limited to, achievement of primary and/or secondary clinical endpoints.

"Post-injection Delirium/Sedation Syndrome" or "PDSS" shall be understood to be defined as those symptoms or combination of symptoms and circumstances as defined in Detke, H. C. et al, BMC Psychiatry 2010, 10:43, which is incorporated by reference herein, or as any physician skilled in the art would understand the term. For example, delirium-related symptoms include disorientation, confusion, ataxia, and dysarthria. Sedation-related symptoms include, for example, somnolence, sedation, or other change in level of consciousness.

The number average molecular weight (Mn) is typically measured by gel permeation chromatography (GPC), usually with a polystyrene standard. The polymers can also be characterized by the weight-average molecular weight (Mw). This can also be measured by gel permeation chromatography (GPC), usually with a polystyrene standard. The polydispersity index is defined as the ratio of Mw over Mn and is typically above 1 and below 2.

In addition, or as an alternative to defining the polymer in terms of number average molecular weight, the polymers can be defined in terms of their theoretical molecular weight. The term "theoretical molecular weight" refers to the molecular weight of the copolymer determined by calculating the sum of the molar weights of the repeat units making the polymer. The theoretical molecular weight indicates the average length of the target polymer chains.

As used herein, the terms "once monthly" or "q1m" or "once per month" mean one time per month and they may be used interchangeably. In some embodiments, "once monthly", or "q1m" or "once per month" mean once every 28 days±5 days, such as, for example, once every 23 days, once every 24 days, once every 25 days, once every 26 days, once every 27 days, once every 28 days, once every 29 days, once every 30 days, once every 31 days, once every 32 days, or once every 33 days. In some embodiments, "once monthly", or "q1m" or "once per month" mean once every 28 days±3 days, such as, for example, once every 25 days, once every 26 days, once every 27 days, once every 28 days, once every 29 days, once every 30 days, or once every 31 days. A "once monthly", "q1m", or "once per month" administration may be made on any day of the month, such as, for example, the 1st day, 2nd day, 3rd day, and so on. A subsequent administration of a "once monthly", "q1m", or "once per month" formulation is then made one month, for example 28 days±5 days, or 28 days±3 days, later.

In some aspects, the disclosure provides pharmaceutical compositions for administration by subcutaneous injection wherein the compositions comprise 20%-45% (w/w) of olanzapine; 35%-65% (w/w) of an organic solvent comprising dimethyl sulfoxide, N-methyl-2-pyrrolidinone (NMP), or a combination thereof; a diblock copolymer comprising polylactic acid and polyethylene glycol and having a number average molecular weight of 6 to 15 kg/mol and comprising 70%-90% by weight (w/w) of polylactic acid; and a triblock copolymer comprising polylactic acid and polyethylene glycol and having a number average molecular weight of 6 to 19 kg/mol and comprising 80%-90% by weight (w/w) of polylactic acid; and wherein the diblock copolymer and triblock copolymer together comprise 10%-25% by weight (w/w) of the composition.

The pharmaceutical compositions of the disclosure are administered by subcutaneous injection. The subcutaneous injection may be made at any suitable site on the skin of the subject to whom the composition is being administered. Exemplary locations are in the abdomen, arm, small of the back, thigh, and the like.

In some aspects, the compositions of the disclosure comprise 20%-45%, optionally 22%-34%, optionally 30%-32%, by weight (w/w) of olanzapine, such as, for example, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5% 40.0%, 41.0%, 41.5%, 42.0%, 42.5%, 43.0%, 43.5%, 44.0%, 44.5%, or 45.0% by weight (w/w) of olanzapine.

In some aspects, the compositions of the disclosure comprise about 20%—about 45% by weight (w/w) of olanzapine, such as, for example, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41.0%, about 41.5%, about 42.0%, about 42.5%, about 43.0%, about 43.5%, about 44.0%, about 44.5%, or about 45.0% by weight (w/w) of olanzapine.

In some embodiments, the compositions of the disclosure comprise 22%-34% by weight (w/w) olanzapine, such as, for example, 22.0%, 22.5%, 23%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5% or 34.0% by weight (w/w) of olanzapine.

In other embodiments, the compositions of the disclosure comprise about 22%—about 34% by weight (w/w) olanzapine, such as, for example, about 22%, about 23%, about 24%, about 25%, about 26%, about 27%, about 28%, about 29%, about 30%, about 31%, about 32%, about 33%, or about 34% by weight (w/w) of olanzapine.

In some embodiments, the compositions of the disclosure comprise 20%-24% by weight (w/w) olanzapine, such as, for example, 20.0, 20.5%, 21.0%, 21.5%, 22.0%, 22.5%, 23%, 23.5%, or 24.0% by weight (w/w) of olanzapine.

In other embodiments, the compositions of the disclosure comprise about 20%-24% by weight (w/w) olanzapine, such as, for example, about 20.0%, about 20.5%, about 21.0%, about 21.5%, about 22.0%, about 22.5%, about 23%, about 23.5%, or about 24.0% by weight (w/w) of olanzapine.

In some embodiments, the compositions of the disclosure comprise 20.5% by weight (w/w) olanzapine.

In other embodiments, the compositions of the disclosure comprise about 20.5% by weight (w/w) olanzapine.

In some embodiments, the compositions of the disclosure comprise 22.0% by weight (w/w) olanzapine.

In other embodiments, the compositions of the disclosure comprise about 22.0% by weight (w/w) olanzapine.

In some embodiments, the compositions of the disclosure comprise 23.5% by weight (w/w) olanzapine.

In other embodiments, the compositions of the disclosure comprise about 23.5% by weight (w/w) olanzapine.

In some embodiments, the compositions of the disclosure comprise 30%-32% by weight (w/w) olanzapine, such as, for example, 30.0%, 30.5%, 31%, 31.5% or 32.0%, by weight (w/w) of olanzapine.

In other embodiments, the compositions of the disclosure comprise about 30%—about 32% by weight (w/w) olanzapine, such as, for example, about 30%, about 31%, or about 32% by weight (w/w) of olanzapine.

In some embodiments, the compositions of the disclosure comprise 26.5% by weight (w/w) olanzapine.

In other embodiments, the compositions of the disclosure comprise about 26.5% by weight (w/w) olanzapine.

In some embodiments, the compositions of the disclosure comprise 29.0% by weight (w/w) olanzapine.

In other embodiments, the compositions of the disclosure comprise about 29.0% by weight (w/w) olanzapine.

In some embodiments, the compositions of the disclosure comprise 30.5% by weight (w/w) olanzapine.

In other embodiments, the compositions of the disclosure comprise about 30.5% by weight (w/w) olanzapine.

In some embodiments, the compositions of the disclosure comprise 32.0% by weight (w/w) olanzapine.

In other embodiments, the compositions of the disclosure comprise about 32.0% by weight (w/w) olanzapine.

In some embodiments, the compositions of the disclosure comprise 33.5% by weight (w/w) olanzapine.

In other embodiments, the compositions of the disclosure comprise about 33.5% by weight (w/w) olanzapine.

In some embodiments, the compositions of the disclosure comprise 40%-45% by weight (w/w) olanzapine, such as, for example, 40.0%, 40.5%, 40.7%, 41.0%, 41.5%, 42.0%, 42.5%, 43.0%, 43.5%, 44.0%, 44.5%, or 45.0% by weight (w/w) of olanzapine.

In other embodiments, the compositions of the disclosure comprise about 40%—about 45% by weight (w/w) olanzapine, such as, for example, about 40.0%, about 40.5%, about 40.7%, about 41.0%, about 41.5%, about 42.0%, about 42.5%, about 43.0%, about 43.5%, about 44.0%, about 44.5%, or about 45.0% by weight (w/w) of olanzapine.

In some embodiments, the compositions of the disclosure comprise 40.7% by weight (w/w) olanzapine.

In other embodiments, the compositions of the disclosure comprise about 40.7% by weight (w/w) olanzapine.

In some embodiments, the compositions of the disclosure comprise 42.0% by weight (w/w) olanzapine.

In other embodiments, the compositions of the disclosure comprise about 42.0% by weight (w/w) olanzapine.

In some embodiments, the compositions of the disclosure comprise 43.5% by weight (w/w) olanzapine.

In other embodiments, the compositions of the disclosure comprise about 43.5% by weight (w/w) olanzapine.

In some embodiments, compositions of the disclosure contain from about 220 mg—about 340 mg of olanzapine per gram of composition, such as, for example, about 220 mg, about 221 mg, about 222 mg, about 223 mg, about 224 mg, about 225 mg, about 226 mg, about 227 mg, about 228 mg, about 229 mg, about 230 mg, about 231 mg, about 232 mg, about 233 mg, about 234 mg, about 235 mg, about 236 mg, about 237 mg, about 238 mg, about 239 mg, about 240 mg, about 241 mg, about 242 mg, about 243 mg, about 244 mg, about 245 mg, about 246 mg, about 247 mg, about 248 mg, about 249 mg, about 250 mg, about 251 mg, about 252 mg, about 253 mg, about 254 mg, about 255 mg, about 256 mg, about 257 mg, about 258 mg, about 259 mg, about 260 mg, about 261 mg, about 262 mg, about 263 mg, about 264 mg, about 265 mg, about 266 mg, about 267 mg, about 268 mg, about 269 mg, about 270 mg, about 271 mg, about 272 mg, about 273 mg, about 274 mg, about 275 mg, about 276 mg, about 277 mg, about 278 mg, about 279 mg, about 280 mg, about 281 mg, about 282 mg, about 283 mg, about 284 mg, about 285 mg, about 286 mg, about 287 mg, about 288 mg, about 289 mg, about 290 mg, about 291 mg, about 292 mg, about 293 mg, about 294 mg, about 295 mg, about 296 mg, about 297 mg, about 298 mg, about 299 mg, about 300 mg, about 301 mg, about 302 mg, about 303 mg, about 304 mg, about 305 mg, about 306 mg, about 307 mg, about 308 mg, about 309 mg, about 310 mg, about 311 mg, about 312 mg, about 313 mg, about 314 mg, about 315 mg, about 316 mg, about 317 mg, about 318 mg, about 319 mg, about 320 mg, about 321 mg, about 322 mg, about 323 mg, about 324 mg, about 325 mg about 326 mg, about 327 mg, about 328 mg, about 329 mg, about 330 mg, about 331 mg, about 332 mg, about 333 mg, about 334 mg, about 335 mg, about 336 mg, about 337 mg, about 338 mg, about 339 mg, or about 340 mg, of olanzapine per gram of composition.

In some embodiments, the compositions of the disclosure contains 265 mg of olanzapine per gram of composition. In some embodiments, the compositions of the disclosure contains about 265 mg of olanzapine per gram of composition.

In some embodiments, the compositions of the disclosure contains 290 mg of olanzapine per gram of composition. In some embodiments, the compositions of the disclosure contains about 290 mg of olanzapine per gram of composition.

In some embodiments, the compositions of the disclosure contains 305 mg of olanzapine per gram of composition. In some embodiments, the compositions of the disclosure contains about 305 mg of olanzapine per gram of composition.

In some embodiments, the compositions of the disclosure contains 320 mg of olanzapine per gram of composition. In some embodiments, the compositions of the disclosure contains about 320 mg of olanzapine per gram of composition.

In some embodiments, the compositions of the disclosure contains 335 mg of olanzapine per gram of composition. In some embodiments, the compositions of the disclosure contains about 335 mg of olanzapine per gram of composition.

In some aspects, the compositions of the disclosure comprise an organic solvent. Organic solvents suitable for use in compositions of the disclosure include benzyl alcohol, benzyl benzoate, diethylene glycol dimethyl ether (Diglyme), diethylene glycol monoethyl ether (DEGMEE), dimethyl isosorbide (DMI), dimethyl sulfoxide (DMSO), ethyl acetate, ethyl benzoate, ethyl lactate, ethylene glycol monoethyl ether acetate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin, or triethylene glycol dimethyl ether (triglyme), or mixtures of the foregoing solvents.

In some aspects, the compositions of the disclosure comprise 35%-65%, optionally 50%-55%, by weight (w/w) of the organic solvent, such as, for example, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, 50.0%, 50.5%, 51.0%, 51.5%, 52.0%, 52.5%, 53.0%, 53.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, or 65.0% by weight (w/w) of an organic solvent.

In some aspects, the compositions of the disclosure comprise about 35%—about 65% by weight (w/w) of the organic solvent, such as, for example, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, or about 65% by weight (w/w) of an organic solvent.

In some aspects, the organic solvent comprises dimethyl sulfoxide, N-methyl-2-pyrrolidinone (NMP), or a combination thereof.

In some embodiments, the organic solvent comprises dimethyl sulfoxide (DMSO). In some embodiments, the organic solvent is preferably dimethyl sulfoxide (DMSO).

In other embodiments, the organic solvent comprises N-methyl-2-pyrrolidinone (NMP). In other embodiments, the organic solvent is N-methyl-2-pyrrolidinone (NMP).

In yet other embodiments, the organic solvent is a mixture of dimethyl sulfoxide (DMSO) and N-methyl-2-pyrrolidinone (NMP). In such embodiments, the DMSO and the NMP may be present in any proportions. In yet another embodiment, the DMSO is preferably present in a higher weight proportion than NMP.

In some embodiments, the compositions of the disclosure comprise 35%-40% by weight (w/w) of the organic solvent, such as, for example 35.0%, 35.5%, 36.0%, 36.5%, 37.0%, 37.5%, 38.0%, 38.5%, 39.0%, 39.5%, or 40.0% by weight (w/w) of the organic solvent.

In other embodiments, the compositions of the disclosure comprise about 35%—about 40% by weight (w/w) of the organic solvent, such as, for example about 35.0%, about 35.5%, about 36.0%, about 36.5%, about 37.0%, about 37.5%, about 38.0%, about 38.5%, about 39.0%, about 39.5%, or about 40.0% by weight (w/w) of the organic solvent.

In some embodiments, the compositions of the disclosure comprise 35% by weight (w/w) of the organic solvent.

In other embodiments, the compositions of the disclosure comprise about 35% by weight (w/w) of the organic solvent.

In some embodiments, the compositions of the disclosure comprise 37.1% by weight (w/w) of the organic solvent.

In other embodiments, the compositions of the disclosure comprise about 37.1% by weight (w/w) of the organic solvent.

In some embodiments, the compositions of the disclosure comprise 38% by weight (w/w) of the organic solvent.

In other embodiments, the compositions of the disclosure comprise about 38% by weight (w/w) of the organic solvent.

In some embodiments, the compositions of the disclosure comprise 50%-55% by weight (w/w) of the organic solvent, such as, for example 50.0%, 50.5%, 51.0%, 51.5%, 52.0%, 52.5%, 53.0%, 53.5%, 54.0%, 54.5% or 55.0% by weight (w/w) of the organic solvent.

In other embodiments, the compositions of the disclosure comprise about 50%—about 55% by weight (w/w) of the organic solvent, such as, for example, about 50%, about 51%, about 52%, about 53%, about 54%, or about 55% by weight (w/w) of an organic solvent.

In some embodiments, the compositions of the disclosure comprise 50% by weight (w/w) of the organic solvent.

In other embodiments, the compositions of the disclosure comprise about 50% by weight (w/w) of the organic solvent.

In some embodiments, the compositions of the disclosure comprise 52% by weight (w/w) of the organic solvent.

In other embodiments, the compositions of the disclosure comprise about 52% by weight (w/w) of the organic solvent.

In some embodiments, the compositions of the disclosure comprise 53.5% by weight (w/w) of the organic solvent.

In other embodiments, the compositions of the disclosure comprise about 53.5% by weight (w/w) of the organic solvent.

In some embodiments, the compositions of the disclosure comprise 54% by weight (w/w) of the organic solvent.

In other embodiments, the compositions of the disclosure comprise about 54% by weight (w/w) of the organic solvent.

In some embodiments, the compositions of the disclosure comprise 55% by weight (w/w) of the organic solvent.

In other embodiments, the compositions of the disclosure comprise about 55% by weight (w/w) of the organic solvent.

In some embodiments, the compositions of the disclosure comprise 58%-62% by weight (w/w) of the organic solvent, such as, for example 58.0%, 58.5%, 59.0%, 59.5%, 60.0%, 60.5%, 61.0%, 61.5%, or 62.0% by weight (w/w) of the organic solvent.

In other embodiments, the compositions of the disclosure comprise about 58%—about 62% by weight (w/w) of the organic solvent, such as, for example about 58.0%, about 58.5%, about 59.0%, about 59.5%, about 60.0%, about 60.5%, about 61.0%, about 61.5%, or about 62.0% by weight (w/w) of the organic solvent.

In some embodiments, the compositions of the disclosure comprise 58.5% by weight (w/w) of the organic solvent.

In other embodiments, the compositions of the disclosure comprise about 58.5% by weight (w/w) of the organic solvent.

In some embodiments, the compositions of the disclosure comprise 60.0% by weight (w/w) of the organic solvent.

In other embodiments, the compositions of the disclosure comprise about 60.0% by weight (w/w) of the organic solvent.

In some embodiments, the compositions of the disclosure comprise 61.5% by weight (w/w) of the organic solvent.

In other embodiments, the compositions of the disclosure comprise about 61.5% by weight (w/w) of the organic solvent.

In some aspects, the compositions of the disclosure comprise a diblock copolymer and a triblock copolymer.

In some aspects, the diblock copolymer in the compositions of the disclosure comprises polylactic acid (PLA) and polyethylene glycol (PEG).

In some embodiments, the polylactic acid (PLA) in the diblock copolymer is composed of randomly distributed D-lactic acid and L-lactic acid monomeric units.

In some embodiments, the polyethylene glycol (PEG) in the diblock copolymer is capped at one end by a $C_1$-$C_6$ alkyl group, such as, for example —$CH_3$, —$CH_2CH_3$, and the like. That is, the terminal hydroxyl group at one end of the polyethylene glycol (PEG) chain is capped with a $C_1$-$C_6$ alkyl group, and the terminal hydroxyl group at the other end of the PEG chain forms an ester bond to the polylactide (PLA) chain.

In some embodiments, the polyethylene glycol (PEG) in the diblock copolymer is capped at one end by —$CH_3$. Such capped PEG may be designated as mPEG. That is, the terminal hydroxyl group at one end of the polyethylene glycol (PEG) chain is capped with —$CH_3$, and the terminal hydroxyl group at the other end of the PEG chain forms an ester bond to the polylactide (PLA) chain. Typically, the diblock copolymer may be obtained by ring-opening polymerization of D,L-lactide initiated by the terminal hydroxyl group of the mPEG chain.

In some aspects, the diblock copolymer in the compositions of the disclosure has the structure:

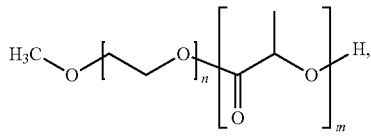

wherein n is the number of ethylene oxide units in the PEG, and m is the number of lactic acid units in the PLA. The theoretical molecular weight of the diblock copolymer can be calculated using the molar masses of lactic acid unit (M(LA)=72 g/mol) and ethylene oxide unit (M(EO)=44 g/mol) and the number of repeat units of each block as follow: MW(mPEG-PLA)=n*44+m*72+32. Typically, the diblock copolymer in the composition of the disclosure has a theoretical molecular weight of 6 to 15 kg/mol. In one embodiment the diblock copolymer has a theoretical molecular weight of 8.0 to 12.5 kg/mol or 6.0 to 9.5 kg/mol.

In some aspects, the diblock copolymer in the compositions of the disclosure has a number average molecular weight of 6 to 15 kg/mol and comprises 70%-90% by weight (w/w) of polylactic acid.

In some aspects, the diblock copolymer in the compositions of the disclosure has a number average molecular weight of 6 to 15 kg/mol, optionally 6.5 to 13.5 kg/mol such as, for example, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, or 15.0 kg/mol.

In some aspects, the diblock copolymer in the compositions of the disclosure has a number average molecular weight of about 6 to about 15 kg/mol, such as, for example, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, about 12.0, about 12.1, about 12.2, about 12.3, about 12.4, about 12.5, about 12.6, about 12.7, about 12.8, about 12.9, about 13.0, about 13.1, about 13.2, about 13.3, about 13.4, about 13.5, about 13.6, about 13.7, about 13.8, about 13.9, about 14.0, about 14.1, about 14.2, about 14.3, about 14.4, about 14.5, about 14.6, about 14.7, about 14.8, about 14.9, or about 15.0 kg/mol.

In some embodiments, the diblock copolymer has a number average molecular weight of 7.0 to 12.5 kg/mol. In other embodiments, the diblock copolymer has a number average molecular weight of from 7.0 to 11.0 kg/mol. In some embodiments, the diblock copolymer has a number average molecular weight of about 10.0 kg/mol. In other embodiments, the diblock copolymer has a number average molecular weight of about 9.0 kg/mol.

In some aspects, the diblock copolymer in the compositions of the disclosure has a molar ratio of lactic acid to ethylene oxide of 1.9-4.0, such as, for example, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0.

In some aspects, the diblock copolymer in the compositions of the disclosure has a molar ratio of lactic acid to ethylene oxide of about 1.9—about 3.5, optionally about 1.9—about 2.9, such as, for example, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, or about 3.5.

In some embodiments, the diblock copolymer in the compositions of the disclosure has a molar ratio of lactic acid to ethylene oxide of 2.4.

In other embodiments, the diblock copolymer in the compositions of the disclosure has a molar ratio of lactic acid to ethylene oxide of about 2.4.

In other embodiments, the diblock copolymer in the compositions of the disclosure has a molar ratio of lactic acid to ethylene oxide of 2.8.

In other embodiments, the diblock copolymer in the compositions of the disclosure has a molar ratio of lactic acid to ethylene oxide of about 2.8.

In some embodiments, the diblock copolymer in the compositions of the disclosure has a molar ratio of lactic acid to ethylene oxide of 3.2.

In other embodiments, the diblock copolymer in the compositions of the disclosure has a molar ratio of lactic acid to ethylene oxide of about 3.2.

In some embodiments, the diblock copolymer in the compositions of the disclosure has a molar ratio of lactic acid to ethylene oxide of 3.5.

In other embodiments, the diblock copolymer in the compositions of the disclosure has a molar ratio of lactic acid to ethylene oxide of about 3.5.

In some aspects, the diblock copolymer in the compositions of the disclosure comprises 70%-90%, optionally 75% to 84%, optionally 84% to 88%, by weight (w/w) of polylactic acid, such as, for example, 70%, 71%, 72%, 73%, 74%, 75%, 76%, 77%, 78%, 79%, 80%, 81%, 82%, 83%, 84%, 85%, 86%, 87%, 88%, 89%, or 90% by weight (w/w) of polylactic acid.

In some aspects, the diblock copolymer in the compositions of the disclosure comprises about 70%—about 90% by weight (w/w) of polylactic acid, such as, for example, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% by weight (w/w) of polylactic acid.

In some embodiments, the diblock copolymer in the compositions of the disclosure comprises 75%-84% by weight (w/w) of polylactic acid, such as, for example, 75%, 76%, 77%, 78%, 79%, 80%, 81%, 82%, 83%, or 84% by weight (w/w) of polylactic acid.

In other embodiments, the diblock copolymer in the compositions of the disclosure comprises about 75%—about 84% by weight (w/w) of polylactic acid, such as, for example, about 75%, about 76%, about 77%, about 78%, about 79%, about 80%, about 81%, about 82%, about 83% or about 84% by weight (w/w) of polylactic acid.

In some embodiments, the diblock copolymer in the compositions of the disclosure comprises 76% by weight (w/w) of polylactic acid.

In other embodiments, the diblock copolymer in the compositions of the disclosure comprises about 76% by weight (w/w) of polylactic acid.

In some embodiments, the diblock copolymer in the compositions of the disclosure comprises 80% by weight (w/w) of polylactic acid.

In other embodiments, the diblock copolymer in the compositions of the disclosure comprises about 80% by weight (w/w) of polylactic acid.

In some embodiments, the diblock copolymer in the compositions of the disclosure comprises 82% by weight (w/w) of polylactic acid.

In other embodiments, the diblock copolymer in the compositions of the disclosure comprises about 82% by weight (w/w) of polylactic acid.

In some embodiments, the diblock copolymer in the compositions of the disclosure comprises 73%-77% by weight (w/w) of polylactic acid, such as, for example, 73%, 74%, 75%, 76%, or 77% by weight (w/w) of polylactic acid.

In other embodiments, the diblock copolymer in the compositions of the disclosure comprises about 73%—about 77% by weight (w/w) of polylactic acid, such as, for example, about 73%, about 74%, about 75%, about 76%, or about 77% by weight (w/w) of polylactic acid.

In some embodiments, the diblock copolymer in the compositions of the disclosure comprises 73% by weight (w/w) of polylactic acid.

In other embodiments, the diblock copolymer in the compositions of the disclosure comprises about 73% by weight (w/w) of polylactic acid.

In some embodiments, the diblock copolymer in the compositions of the disclosure comprises 75% by weight (w/w) of polylactic acid.

In other embodiments, the diblock copolymer in the compositions of the disclosure comprises about 75% by weight (w/w) of polylactic acid.

In some embodiments, the diblock copolymer in the compositions of the disclosure comprises 77% by weight (w/w) of polylactic acid.

In other embodiments, the diblock copolymer in the compositions of the disclosure comprises about 77% by weight (w/w) of polylactic acid.

In some embodiments, the diblock copolymer in the compositions of the disclosure comprises 84%-88% by weight (w/w) of polylactic acid, such as, for example, 84%, 85%, 86%, 87%, or 88%, by weight (w/w) of polylactic acid.

In other embodiments, the diblock copolymer in the compositions of the disclosure comprises about 84%-88% by weight (w/w) of polylactic acid, such as, for example, about 84%, about 85%, about 86%, about 87%, or about 88%, by weight (w/w) of polylactic acid.

In some embodiments, the diblock copolymer in the compositions of the disclosure comprises 84% by weight (w/w) of polylactic acid.

In some embodiments, the diblock copolymer in the compositions of the disclosure comprises about 84% by weight (w/w) of polylactic acid.

In some embodiments, the diblock copolymer in the compositions of the disclosure comprises 86% by weight (w/w) of polylactic acid.

In some embodiments, the diblock copolymer in the compositions of the disclosure comprises about 86% by weight (w/w) of polylactic acid.

In some embodiments, the diblock copolymer in the compositions of the disclosure comprises 88% by weight (w/w) of polylactic acid.

In some embodiments, the diblock copolymer in the compositions of the disclosure comprises about 88% by weight (w/w) of polylactic acid.

In some aspects, the weight ratio of the diblock copolymer to the triblock copolymer is from 6:1 to 2:1, optionally about 4:1.

In some aspects, the compositions of the disclosure comprise 10%-18% by weight (w/w), optionally 10-15%, optionally 12-17%, of the diblock copolymer, such as, for example, 10%, 11%, 12%, 13%, 14%, 15%, 16%, 17%, or 18% by weight (w/w) of the diblock copolymer.

In some aspects, the compositions of the disclosure comprise about 10%—about 17% by weight (w/w) of the diblock copolymer, such as, for example, about 10%, about 11%, about 12%, about 13%, about 14%, about 15%, about 16%, about 17%, or about 18% by weight (w/w) of the diblock copolymer.

In some embodiments, the compositions of the disclosure comprise 17.8% by weight (w/w) of the diblock copolymer.

In other embodiments, the compositions of the disclosure comprise about 17.8% by weight (w/w) of the diblock copolymer.

In some aspects, the compositions of the disclosure comprise 10%-15% by weight (w/w) of the diblock copolymer, such as, for example, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0% by weight (w/w) of the diblock copolymer.

In some aspects, the compositions of the disclosure comprise about 10—about 15% by weight (w/w) of the diblock copolymer, such as, for example, about 10%, about 11%, about 12%, about 13%, about 14%, or about 15% by weight (w/w) of the diblock copolymer.

In some embodiments, the compositions of the disclosure comprise 12.2% by weight (w/w) of the diblock copolymer.

In other embodiments, the compositions of the disclosure comprise about 12.2% by weight (w/w) of the diblock copolymer.

In some embodiments, the compositions of the disclosure comprise 12.8% by weight (w/w) of the diblock copolymer.

In other embodiments, the compositions of the disclosure comprise about 12.8% by weight (w/w) of the diblock copolymer.

In some embodiments, the compositions of the disclosure comprise 13.2% by weight (w/w) of the diblock copolymer.

In other embodiments, the compositions of the disclosure comprise about 13.2% by weight (w/w) of the diblock copolymer.

In some embodiments, the compositions of the disclosure comprise 13.6% by weight (w/w) of the diblock copolymer.

In other embodiments, the compositions of the disclosure comprise about 13.6% by weight (w/w) of the diblock copolymer.

In some embodiments, the compositions of the disclosure comprise 14.0% by weight (w/w) of the diblock copolymer.

In other embodiments, the compositions of the disclosure comprise about 14.0% by weight (w/w) of the diblock copolymer.

In some embodiments, the compositions of the disclosure comprise 14.4% by weight (w/w) of the diblock copolymer.

In other embodiments, the compositions of the disclosure comprise about 14.4% by weight (w/w) of the diblock copolymer.

In some aspects, the triblock copolymer in the compositions of the disclosure comprises polylactic acid (PLA) and polyethylene glycol (PEG).

In some embodiments, the polylactic acid (PLA) in the triblock copolymer is composed of randomly distributed D-lactic acid and L-lactic acid monomeric units.

In some embodiments, the triblock copolymer in the compositions of the disclosure is an A-B-A copolymer in which the A groups are polylactic acid and the B group is polyethylene glycol (PEG). In these embodiments, the terminal hydroxyl group at either end of the polyethylene glycol (PEG) chain forms an ester bond to the polylactide (PLA) chain. Typically, the triblock copolymer may be obtained by ring-opening polymerization of D,L-lactide initiated by the terminal hydroxyl group of the PEG chain.

In some aspects, the triblock copolymer in the compositions of the disclosure has the structure:

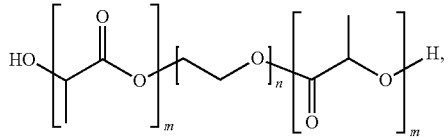

wherein n is the number of ethylene oxide units in the PEG, and each m is the number of lactic acid units in the PLA group to which it refers. The theoretical molecular weight of the triblock copolymer can be calculated using the molar masses of lactic acid unit (M(LA), 72 g/mol) and ethylene oxide unit (M(EO), 44 g/mol) and the number of repeat units of each block as follow: MW(PLA-PEG-PLA)=n*44+2*m*72+18. The triblock copolymer in the compositions of the disclosure has a theoretical molecular weight of 6 to 19 kg/mol, In one embodiment the triblock copolymer has a theoretical molecular weight of 6.5 to 9.0 kg/mol or 10.0 to 17.0 kg/mol.

In some aspects, the triblock copolymer in the compositions of the disclosure has a number average molecular weight of 6 to 19 kg/mol and comprises 80%-90% by weight (w/w) of polylactic acid.

In some aspects, the triblock copolymer in the compositions of the disclosure has a number average molecular weight of 6 to 19 kg/mol, optionally 6 to 13 kg/mol, optionally 9 to 18 kg/mol, optionally 7 to 12 kg/mol, optionally 10 to 17 kg/mol, such as, for example, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, or 19.0 kg/mol.

In some aspects, the triblock copolymer in the compositions of the disclosure has a number average molecular weight of about 6 to about 19 kg/mol, optionally about 6 to about 13 kg/mol, optionally about 9 to about 18 kg/mol, optionally about 7 to about 12 kg/mol, optionally about 10 to about 17 kg/mol, such as, for example, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, about 12.0, about 12.1, about 12.2, about 12.3, about 12.4, about 12.5, about 12.6, about 12.7, about 12.8, about 12.9, about 13.0, about 13.1, about 13.2, about 13.3, about 13.4, about 13.5, about 13.6, about 13.7, about 13.8, about 13.9, about 14.0, about 14.1, about 14.2, about 14.3, about 14.4, about 14.5, about 14.6, about 14.7, about 14.8, about 14.9, about 15.0, about 16.0, about 16.1, about 16.2, about 16.3, about 16.4, about 16.5, about 16.6, about 16.7, about 16.8, about 16.9, about 17.0, about 17.1, about 17.2, about 17.3, about 17.4, about 17.5, about 17.6, about 17.7, about 17.8, about 17.9, about 18.0, about 18.1, about 18.2, about 18.3, about 18.4, about 18.5, about 18.6, about 18.7, about 18.8, about 18.9, or about 19.0 kg/mol.

The triblock copolymer may have a number average molecular weight of about 6 to about 13 kg/mol, optionally about 7 to about 12 kg/mol. The triblock copolymer may have a number average molecular weight of 9 to 18 kg/mol, optionally 10 to 17 kg/mol. The triblock copolymer may have a number average molecular weight of about 9.5 kg/mol. The triblock copolymer may have a number average molecular weight of about 14 kg/mol.

In some aspects, the triblock copolymer in the compositions of the disclosure has a molar ratio of lactic acid to ethylene oxide of 2.8-4.5, such as, for example, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5.

In some aspects, the triblock copolymer in the compositions of the disclosure has a molar ratio of lactic acid to ethylene oxide of about 2.8—about 4.5, such as, for example, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, or about 4.5.

In some embodiments, the triblock copolymer in the compositions of the disclosure has a molar ratio of lactic acid to ethylene oxide of 3.5-4.5, such as, for example, 3.5, 3.6, 3.7, 3.8, 3.9, 4.0, 4.1, 4.2, 4.3, 4.4 or 4.5.

In some embodiments, the triblock copolymer in the compositions of the disclosure has a molar ratio of lactic acid to ethylene oxide of about 3.5—about 4.5, such as, for example about 3.5, about 3.6, about 3.7, about 3.8, about 3.9, about 4.0, about 4.1, about 4.2, about 4.3, about 4.4 or about 4.5.

In some embodiments, the triblock copolymer in the compositions of the disclosure has a molar ratio of lactic acid to ethylene oxide of 3.6.

In other embodiments, the triblock copolymer in the compositions of the disclosure has a molar ratio of lactic acid to ethylene oxide of about 3.6.

In some embodiments, the triblock copolymer in the compositions of the disclosure has a molar ratio of lactic acid to ethylene oxide of 3.8.

In other embodiments, the triblock copolymer in the compositions of the disclosure has a molar ratio of lactic acid to ethylene oxide of about 3.8.

In some embodiments, the triblock copolymer in the compositions of the disclosure has a molar ratio of lactic acid to ethylene oxide of 4.0.

In other embodiments, the triblock copolymer in the compositions of the disclosure has a molar ratio of lactic acid to ethylene oxide of about 4.0.

In some embodiments, the triblock copolymer in the compositions of the disclosure has a molar ratio of lactic acid to ethylene oxide of 4.2.

In other embodiments, the triblock copolymer in the compositions of the disclosure has a molar ratio of lactic acid to ethylene oxide of about 4.2.

In some embodiments, the triblock copolymer in the compositions of the disclosure has a molar ratio of lactic acid to ethylene oxide of 4.4.

In other embodiments, the triblock copolymer in the compositions of the disclosure has a molar ratio of lactic acid to ethylene oxide of about 4.4.

In some aspects, the triblock copolymer in the compositions of the disclosure comprises 80%-90% by weight (w/w) of polylactic acid, such as, for example, 80%, 81%, 82%, 83%, 84%, 85%, 86%, 87%, 88%, 89%, or 90% by weight (w/w) of polylactic acid.

In some aspects, the triblock copolymer in the compositions of the disclosure comprises about 80%—about 90%, optionally 83%-88%, optionally 85%-88%, optionally about 88% by weight (w/w) of polylactic acid, such as, for example, about 80%, about 81%, about 82%, about 83%, about 84%, about 85%, about 86%, about 87%, about 88%, about 89%, or about 90% by weight (w/w) of polylactic acid.

In some embodiments, the triblock copolymer in the compositions of the disclosure comprises 83%-88% by weight (w/w) of polylactic acid, such as, for example, 83%, 84%, 85%, 86%, or 87% or 88% by weight (w/w) of polylactic acid.

In other embodiments, the triblock copolymer in the compositions of the disclosure comprises about 83%—about 88% by weight (w/w) of polylactic acid, such as, for example, about 83%, about 84%, about 85%, about 86%, about 87%, or about 88% by weight (w/w) of polylactic acid.

In some embodiments, the triblock copolymer in the compositions of the disclosure comprises 85%-88% by weight (w/w) of polylactic acid, such as, for example, 85%, 86%, 87% or 88% by weight (w/w) of polylactic acid.

In some embodiments, the triblock copolymer in the compositions of the disclosure comprises about 85%—about 88% by weight (w/w) of polylactic acid, such as, for example, about 85%, about 86%, about 87% or about 88% by weight (w/w) of polylactic acid.

In some embodiments, the triblock copolymer in the compositions of the disclosure comprises preferably about 85% by weight (w/w) of polylactic acid.

In some embodiments, the triblock copolymer in the compositions of the disclosure comprises preferably about 87% by weight (w/w) of polylactic acid.

In some embodiments, the triblock copolymer in the compositions of the disclosure comprises 82%-87% by weight (w/w) of polylactic acid, such as, for example, 82%, 83%, 84%, 85%, 86%, or 87% by weight (w/w) of polylactic acid. In some embodiments, the triblock copolymer in the compositions of the disclosure preferably comprises 85% by weight (w/w) of polylactic acid.

In some embodiments, the triblock copolymer in the compositions of the disclosure comprises about 82%—about 87% by weight (w/w) of polylactic acid, such as, for example, about 82%, about 83%, about 84%, about 85%, about 86%, about 87% or about 88% by weight (w/w) of polylactic acid. In some embodiments, the triblock copolymer in the compositions of the disclosure preferably comprises about 85% by weight (w/w) of polylactic acid.

In some aspects, the compositions of the disclosure comprise 3%-5%, optionally 3%-4%, by weight (w/w) of the triblock copolymer, such as, for example, 3%, 4%, or 5% by weight (w/w) of the triblock copolymer.

In some aspects, the compositions of the disclosure comprise about 3%—about 5% by weight (w/w) of the triblock copolymer, such as, for example, about 3%, about 4%, or about 5% by weight (w/w) of the triblock copolymer.

In some aspects, the compositions of the disclosure comprise 3%-4% by weight (w/w) of the triblock copolymer, such as, for example, 3%, or 4% by weight (w/w) of the triblock copolymer.

In some aspects, the compositions of the disclosure comprise about 3%—about 4% by weight (w/w) of the triblock copolymer, such as, for example, about 3%, or about 4% by weight (w/w) of the triblock copolymer.

In some embodiments, the compositions of the disclosure comprise 3.0% by weight (w/w) of the triblock copolymer.

In other embodiments, the compositions of the disclosure comprise about 3.0% by weight (w/w) of the triblock copolymer.

In some embodiments, the compositions of the disclosure comprise 3.2% by weight (w/w) of the triblock copolymer.

In other embodiments, the compositions of the disclosure comprise about 3.2% by weight (w/w) of the triblock copolymer.

In some embodiments, the compositions of the disclosure comprise 3.5% by weight (w/w) of the triblock copolymer.

In other embodiments, the compositions of the disclosure comprise about 3.5% by weight (w/w) of the triblock copolymer.

In some embodiments, the compositions of the disclosure comprise 3.6% by weight (w/w) of the triblock copolymer.

In other embodiments, the compositions of the disclosure comprise about 3.6% by weight (w/w) of the triblock copolymer.

In some embodiments, the compositions of the disclosure comprise 3.7% by weight (w/w) of the triblock copolymer.

In other embodiments, the compositions of the disclosure comprise about 3.7% by weight (w/w) of the triblock copolymer.

In some embodiments, the compositions of the disclosure comprise 4.5% by weight (w/w) of the triblock copolymer.

In other embodiments, the compositions of the disclosure comprise about 4.5% by weight (w/w) of the triblock copolymer.

In some aspects, in the compositions of the disclosure, the diblock copolymer and the triblock copolymer together comprise 10%-25%, optionally 10-20%, optionally 14-20%, by weight (w/w) of the composition, such as, for example, 10%, 11%, 12%, 13%, 14%, 15%, 16%, 17%, 18%, 19%, 20%, 21%, 22%, 23%, 24%, or 25% by weight (w/w) of the composition.

In some embodiments, in the compositions of the disclosure, the diblock copolymer and the triblock copolymer together comprise about 10%—about 25%, optionally about 10—about 20%, optionally about 14—about 20%, by weight (w/w) of the composition, such as, for example, about 10%, about 11%, about 12%, about 13%, about 14%, about 15%, about 16%, about 17%, about 18%, about 19%, about 20%, about 21%, about 22%, about 23%, about 24%, or about 25% by weight (w/w) of the composition.

In some embodiments, in the compositions of the disclosure, the diblock copolymer and the triblock copolymer together comprise 12% by weight (w/w) of the composition.

In other embodiments, in the compositions of the disclosure, the diblock copolymer and the triblock copolymer together comprise about 12% by weight (w/w) of the composition.

In some embodiments, in the compositions of the disclosure, the diblock copolymer and the triblock copolymer together comprise 14% by weight (w/w) of the composition.

In other embodiments, in the compositions of the disclosure, the diblock copolymer and the triblock copolymer together comprise about 14% by weight (w/w) of the composition.

In some embodiments, in the compositions of the disclosure, the diblock copolymer and the triblock copolymer together comprise 16% by weight (w/w) of the composition.

In other embodiments, in the compositions of the disclosure, the diblock copolymer and the triblock copolymer together comprise about 16% by weight (w/w) of the composition.

In some embodiments, in the compositions of the disclosure, the diblock copolymer and the triblock copolymer together comprise 18% by weight (w/w) of the composition.

In other embodiments, in the compositions of the disclosure, the diblock copolymer and the triblock copolymer together comprise about 18% by weight (w/w) of the composition.

In some embodiments, in the compositions of the disclosure, the diblock copolymer and the triblock copolymer together comprise 20% by weight (w/w) of the composition.

In other embodiments, in the compositions of the disclosure, the diblock copolymer and the triblock copolymer together comprise about 20% by weight (w/w) of the composition.

In some embodiments, in the compositions of the disclosure, the diblock copolymer and the triblock copolymer together comprise 22% by weight (w/w) of the composition.

In other embodiments, in the compositions of the disclosure, the diblock copolymer and the triblock copolymer together comprise about 22% by weight (w/w) of the composition.

In one embodiment, the composition comprises:
20%-45% (w/w) of olanzapine;
35%-65% (w/w) of an organic solvent comprising dimethyl sulfoxide, N-methyl-2-pyrrolidinone (NMP), or a combination thereof;
10%-17% (w/w) of a diblock copolymer comprising polylactic acid and polyethylene glycol and having a number average molecular weight of 6 to 15 kg/mol and comprising 70%-90% by weight (w/w) polylactic acid; and
3%-5% (w/w) of a triblock copolymer comprising polylactic acid and polyethylene glycol and having a number average molecular weight of 6 to 19 kg/mol and comprising 80%-90% by weight (w/w) polylactic acid;
and wherein the diblock copolymer and triblock copolymer together comprise 13%-22% by weight (w/w) of the composition.

In one embodiment, the composition comprises:
22%-34% (w/w) of olanzapine;
50%-55% (w/w) of an organic solvent comprising dimethyl sulfoxide, N-methyl-2-pyrrolidinone (NMP), or a combination thereof;
10%-15% (w/w) of a diblock copolymer comprising polylactic acid and polyethylene glycol and having a number average molecular weight of 6 to 15 kg/mol and comprising 70%-90% by weight (w/w) polylactic acid; and
3%-4% (w/w) of a triblock copolymer comprising polylactic acid and polyethylene glycol and having a number average molecular weight of 6 to 19 kg/mol and comprising 80%-90% by weight (w/w) polylactic acid;
and wherein the diblock copolymer and triblock copolymer together comprise 13%-19% by weight (w/w) of the composition.

In one embodiment, the composition comprises:
30%-32% (w/w) of olanzapine;
52%-54% (w/w) of an organic solvent comprising dimethyl sulfoxide, N-methyl-2-pyrrolidinone (NMP), or a combination thereof;
12%-14% (w/w) of a diblock copolymer comprising polylactic acid and polyethylene glycol and having a number average molecular weight of 6 to 15 kg/mol and comprising 70%-90% by weight (w/w) polylactic acid; and
3%-3.5% (w/w) of a triblock copolymer comprising polylactic acid and polyethylene glycol and having a number average molecular weight of 6 to 19 kg/mol and comprising 80%-90% by weight (w/w) polylactic acid;
and wherein the diblock copolymer and triblock copolymer together comprise 15%-17.5% by weight (w/w) of the composition.

In one embodiment, the composition comprises:
20%-45% (w/w) of olanzapine;
35%-65% (w/w) of an organic solvent comprising dimethyl sulfoxide, N-methyl-2-pyrrolidinone (NMP), or a combination thereof;
10%-17% (w/w) of a diblock copolymer comprising polylactic acid and polyethylene glycol and having a number average molecular weight of 6.5 to 13.5 kg/mol and comprising 75%-84% by weight (w/w) polylactic acid; and
3%-5% (w/w) of a triblock copolymer comprising polylactic acid and polyethylene glycol and having a number average molecular weight of 6 to 13 kg/mol and comprising 83%-88% by weight (w/w) polylactic acid;
and wherein the diblock copolymer and triblock copolymer together comprise 13%-22% by weight (w/w) of the composition.

In one embodiment, the composition comprises:
22%-34% (w/w) of olanzapine;
50%-55% (w/w) of an organic solvent comprising dimethyl sulfoxide, N-methyl-2-pyrrolidinone (NMP), or a combination thereof;
10%-15% (w/w) of a diblock copolymer comprising polylactic acid and polyethylene glycol and having a number average molecular weight of 6.5 to 12.5 kg/mol and comprising 75%-84% by weight (w/w) polylactic acid; and
3%-4% (w/w) of a triblock copolymer comprising polylactic acid and polyethylene glycol and having a number average molecular weight of 6 to 13 kg/mol and comprising 83%-88% by weight (w/w) polylactic acid;
and wherein the diblock copolymer and triblock copolymer together comprise 13%-19% by weight (w/w) of the composition.

In one embodiment, the composition comprises:
30%-32% (w/w) of olanzapine;
52%-54% (w/w) of an organic solvent comprising dimethyl sulfoxide, N-methyl-2-pyrrolidinone (NMP), or a combination thereof;
12%-14% (w/w) of a diblock copolymer comprising polylactic acid and polyethylene glycol and having a number average molecular weight of 6.5 to 12.5 kg/mol and comprising 75%-84% by weight (w/w) polylactic acid; and
3%-3.5% (w/w) of a triblock copolymer comprising polylactic acid and polyethylene glycol and having a number average molecular weight of 6 to 13 kg/mol and comprising 83%-88% by weight (w/w) polylactic acid;
and wherein the diblock copolymer and triblock copolymer together comprise 15%-17.5% by weight (w/w) of the composition.

In one embodiment, the composition comprises:
30%-32% (w/w) of olanzapine;
52%-54% (w/w) of dimethyl sulfoxide;
12%-14% (w/w) of a diblock copolymer comprising polylactic acid and polyethylene glycol and having a number average molecular weight of 6.5 to 12.5 kg/mol and comprising 75%-84% by weight (w/w) polylactic acid; and
3%-3.5% (w/w) of a triblock copolymer comprising polylactic acid and polyethylene glycol and having a number average molecular weight of 6 to 13 kg/mol and comprising 83%-88% by weight (w/w) polylactic acid;
and wherein the diblock copolymer and triblock copolymer together comprise 15%-17.5% by weight (w/w) of the composition.

In one embodiment, the composition comprises:
20%-45% (w/w) of olanzapine;
35%-65% (w/w) of an organic solvent comprising dimethyl sulfoxide, N-methyl-2-pyrrolidinone (NMP), or a combination thereof;
10%-17% (w/w) of a diblock copolymer comprising polylactic acid and polyethylene glycol and having a number average molecular weight of 6.5 to 13.5 kg/mol and comprising 75%-84% by weight (w/w) polylactic acid; and
3%-5% (w/w) of a triblock copolymer comprising polylactic acid and polyethylene glycol and having a number average molecular weight of 9 to 18 kg/mol and comprising 83%-88% by weight (w/w) polylactic acid;
and wherein the diblock copolymer and triblock copolymer together comprise 13%-22% by weight (w/w) of the composition.

In one embodiment, the composition comprises:
22%-34% (w/w) of olanzapine;
50%-55% (w/w) of an organic solvent comprising dimethyl sulfoxide, N-methyl-2-pyrrolidinone (NMP), or a combination thereof;
10%-15% (w/w) of a diblock copolymer comprising polylactic acid and polyethylene glycol and having a number average molecular weight of 6.5 to 12.5 kg/mol and comprising 75%-84% by weight (w/w) polylactic acid; and
3%-4% (w/w) of a triblock copolymer comprising polylactic acid and polyethylene glycol and having a number average molecular weight of 9 to 18 kg/mol and comprising 83%-88% by weight (w/w) polylactic acid;
and wherein the diblock copolymer and triblock copolymer together comprise 13%-19% by weight (w/w) of the composition.

In one embodiment, the composition comprises:
30%-32% (w/w) of olanzapine;
52%-54% (w/w) of an organic solvent comprising dimethyl sulfoxide, N-methyl-2-pyrrolidinone (NMP), or a combination thereof;
12%-14% (w/w) of a diblock copolymer comprising polylactic acid and polyethylene glycol and having a number average molecular weight of 6.5 to 12.5 kg/mol and comprising 75%-84% by weight (w/w) polylactic acid; and
3%-3.5% (w/w) of a triblock copolymer comprising polylactic acid and polyethylene glycol and having a number average molecular weight of 9 to 18 kg/mol and comprising 83%-88% by weight (w/w) polylactic acid;
and wherein the diblock copolymer and triblock copolymer together comprise 15%-17.5% by weight (w/w) of the composition.

In one embodiment, the composition comprises:
20%-40% (w/w) of olanzapine;
40%-65% (w/w) of an organic solvent comprising dimethyl sulfoxide, N-methyl-2-pyrrolidinone (NMP), or a combination thereof;
10%-17% (w/w) of a diblock copolymer comprising polylactic acid and polyethylene glycol and having a number average molecular weight of 7.0 to 12.5 kg/mol and comprising 78%-81% by weight (w/w) polylactic acid; and
3%-5% (w/w) of a triblock copolymer comprising polylactic acid and polyethylene glycol and having a number average molecular weight of 7.0 to 12.0 kg/mol and comprising 85%-88% by weight (w/w) polylactic acid;
and wherein the diblock copolymer and triblock copolymer together comprise 13%-22% by weight (w/w) of the composition.

In one embodiment, the composition comprises:
22%-34% (w/w) of olanzapine;
50%-55% (w/w) of an organic solvent comprising dimethyl sulfoxide, N-methyl-2-pyrrolidinone (NMP), or a combination thereof;
10%-15% (w/w) of a diblock copolymer comprising polylactic acid and polyethylene glycol and having a number average molecular weight of 7.0 to 12.5 kg/mol and comprising 78%-81% by weight (w/w) polylactic acid; and 3%-4% (w/w) of a triblock copolymer comprising polylactic acid and polyethylene glycol and having a number average molecular weight of 7.0 to 12.0 kg/mol and comprising 85%-88% by weight (w/w) polylactic acid;

and wherein the diblock copolymer and triblock copolymer together comprise 13%-19% by weight (w/w) of the composition.

In one embodiment, the composition comprises:
30%-32% (w/w) of olanzapine;
52%-54% (w/w) of an organic solvent comprising dimethyl sulfoxide, N-methyl-2-pyrrolidinone (NMP), or a combination thereof;
12%-14% (w/w) of a diblock copolymer comprising polylactic acid and polyethylene glycol and having a number average molecular weight of 7.0 to 12.5 kg/mol and comprising 78%-81% by weight (w/w) polylactic acid; and
3%-3.5% (w/w) of a triblock copolymer comprising polylactic acid and polyethylene glycol and having a number average molecular weight of 7.0 to 12.0 kg/mol and comprising 85%-88% by weight (w/w) polylactic acid;

and wherein the diblock copolymer and triblock copolymer together comprise 15%-17.5% by weight (w/w) of the composition.

In some aspects, the disclosure is directed to a kit comprising a container containing 318 mg-950 mg, optionally 550-950 mg, optionally 450 mg-800 mg of olanzapine; and a container containing a 0.73-2.5 grams, optionally 1.3-2.5 grams, optionally 0.9-2.1 grams of a mixture of an organic solvent that is dimethyl sulfoxide (DMSO), N-methyl-2-pyrrolidinone (NMP), or a combination thereof, a diblock copolymer comprising polylactic acid and polyethylene glycol and having a number average molecular weight of 6.5 to 15 kg/mol and comprising 70%-90% by weight (w/w) of polylactic acid, and a triblock copolymer comprising polylactic acid and polyethylene glycol and having a number average molecular weight of 7 to 15 kg/mol and comprising 80%-90% by weight (w/w) of polylactic acid.

In some aspects, the kits of the disclosure comprise a container containing olanzapine.

In some aspects, the kits of the disclosure comprise a container containing 318 mg-950 mg, optionally 550-950 mg, optionally 450 mg-800 mg of olanzapine, such as, for example, 318 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 531 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 637 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 743 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, or 950 mg of olanzapine.

In some aspects, the kits of the disclosure comprise a container containing about 318 mg—about 950 mg, optionally about 550-950 mg, optionally 450 mg-800 mg of olanzapine, such as, for example, about 318 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 505 mg, about 510 mg, about 515 mg, about 520 mg, about 525 mg, about 530 mg, about 531 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 605 mg, about 610 mg, about 615 mg, about 620 mg, about 625 mg, about 630 mg, about 635 mg, about 637 mg, about 640 mg, about 645 mg, about 650 mg, about 655 mg, about 660 mg, about 665 mg, about 670 mg, about 675 mg, about 680 mg, about 685 mg, about 690 mg, about 695 mg, about 700 mg, about 705 mg, about 710 mg, about 715 mg, about 720 mg, about 725 mg, about 730 mg, about 735 mg, about 740 mg, about 743 mg, about 745 mg, about 750 mg, about 755 mg, about 760 mg, about 765 mg, about 770 mg, about 775 mg, about 780 mg, about 785 mg, about 790 mg, about 795 mg, about 800 mg, about 805 mg, about 810 mg, about 815 mg, about 820 mg, about 825 mg, about 830 mg, about 835 mg, about 840 mg, about 845 mg, about 850 mg, about 855 mg, about 860 mg, about 865 mg, about 870 mg, about 875 mg, about 880 mg, about 885 mg, about 890 mg, about 895 mg, about 900 mg, about 905 mg, about 910 mg, about 915 mg, about 920 mg, about 925 mg, about 930 mg, about 935 mg, about 940 mg, about 945 mg, or about 950 mg of olanzapine.

In some embodiments, the kits of the disclosure comprise a container containing 318 mg of olanzapine.

In other embodiments, the kits of the disclosure comprise a container containing about 318 mg of olanzapine.

In some embodiments, the kits of the disclosure comprise a container containing 575 mg of olanzapine.

In other embodiments, the kits of the disclosure comprise a container containing about 575 mg of olanzapine.

In some embodiments, the kits of the disclosure comprise a container containing 600 mg of olanzapine.

In other embodiments, the kits of the disclosure comprise a container containing about 600 mg of olanzapine.

In some embodiments, the kits of the disclosure comprise a container containing 710 mg of olanzapine.

In other embodiments, the kits of the disclosure comprise a container containing about 710 mg of olanzapine.

In some embodiments, the kits of the disclosure comprise a container containing 815 mg of olanzapine.

In other embodiments, the kits of the disclosure comprise a container containing about 815 mg of olanzapine.

In some embodiments, the kits of the disclosure comprise a container containing 885 mg of olanzapine.

In other embodiments, the kits of the disclosure comprise a container containing about 885 mg of olanzapine.

In some aspects, the kits of the disclosure comprise a container containing a mixture of organic solvent, a diblock copolymer, and a triblock copolymer.

In some aspects, the kits of the disclosure comprise a container containing 0.73-2.5 grams, optionally 1.3-2.5 grams, optionally 0.9-2.1 grams of a mixture of organic solvent, a diblock copolymer, and a triblock copolymer, such as, for example, 0.73, 0.8, 0.9, 1.0, 1.1, 1.2, 1.26, 1.3, 1.4, 1.5, 1.50, 1.6, 1.7, 1.74, 1.8, 1.9, 2.0, 2.1, 2.2, 2.3, 2.4, or 2.5 grams of a mixture of organic solvent, a diblock copolymer, and a triblock copolymer.

In some aspects, the kits of the disclosure comprise a container containing about 0.73—about 2.5 grams, optionally about 1.3—about 2.5 grams, of a mixture of organic solvent, a diblock copolymer, and a triblock copolymer, such as, for example, about 0.73, about 0.8, about 0.9, about 1.0, about 1.1, about 1.2, about 1.26, about 1.3, about 1.4, about 1.5, about 1.50, about 1.6, about 1.7, about 1.74, about 1.8, about 1.9, about 2.0, about 2.1, about 2.2, about 2.3, about 2.4, or about 2.5 grams of a mixture of organic solvent, a diblock copolymer, and a triblock copolymer.

In some aspects, the kits of the disclosure comprise a container containing 0.73-2.5 grams of a mixture of an organic solvent that is dimethyl sulfoxide (DMSO), N-methyl-2-pyrrolidinone (NMP), or a combination thereof, a diblock copolymer comprising polylactic acid and polyethylene glycol and having a number average molecular weight of 6.5 to 15 kg/mol and comprising 70%-90% by weight (w/w) of polylactic acid, and a triblock copolymer comprising polylactic acid and polyethylene glycol and having a number average molecular weight of 7 to 15 kg/mol and comprising 80%-90% by weight (w/w) of polylactic acid.

In some embodiments, the container containing the mixture of organic solvent, the diblock copolymer, and the triblock copolymer contains about 0.73 grams of the mixture.

In some embodiments, the container containing the mixture of organic solvent, the diblock copolymer, and the triblock copolymer contains about 1.4 grams of the mixture.

In some embodiments, the container containing the mixture of organic solvent, the diblock copolymer, and the triblock copolymer contains about 1.5 grams of the mixture.

In some embodiments, the container containing the mixture of organic solvent, the diblock copolymer, and the triblock copolymer contains about 1.7 grams of the mixture.

In some embodiments, the container containing the mixture of organic solvent, the diblock copolymer, and the triblock copolymer contains about 2.0 grams of the mixture.

In some embodiments of the kits of the disclosure, the olanzapine in the kit has a particle size distribution characterized by a D(90) of from about 20 µm to about 37 µm, a particle size distribution characterized by a D(3,2) of from about 5.5 µm to about 7.5 µm, or a tapped density from about 0.35 g/ml to 0.44 g/ml, or any combination thereof. Olanzapine having these characteristics is described in U.S. Provisional Application No. 63/301,202, filed on Jan. 20, 2022.

As used herein, the term "D(90)" means that that 90% (by volume) of the particles have a diameter less than or equal to the indicated value. For example, a D(90) (or d(90) of 25 µm, means that 90% (by volume) of the particles have a diameter less than or equal to 25 µm. As used herein, the term "D(3,2)" refers to the surface area moment mean (Sauter Mean Diameter, SMD) and may be relevant where surface area is important e.g. dissolution and reflects the amount of fine particles in the sample. Particle size is typically determined by means of laser diffractometry, optionally using a Mastersizer device from Malvern Instruments.

As used herein, "tapped density" (TD) refers to the ability of a powder sample to pack under taps and gives a measure of the powder cohesiveness which can be linked to its flowability and filling performance. Tapped density may be determined by methods known to those skilled in the art. For example, bulk density/tapped density may be determined by European Pharmacopoeia 2.9.34. Method 1 (https://www-.drugfuture.com/Pharmacopoeia/EP7/DATA/20934E.PDF; PDF downloaded Nov. 14, 2021). In particular, the bulk and tapped densities may be determined using the Tapped Density Tester SVM 122 from ERWEKA, equipped with a 100 mL glass cylinder. Approximately 30 g of the powder is poured into the 100 mL measuring cylinder with a funnel. Bulk density is calculated by dividing the amount of powder (in gram) by the measured volume (mL). The tapped density is then determined as follows:

Step (i) Tap the sample 10 times and read the volume $V_{10}$;
Step (ii) Tap the sample 500 times (10+490) and read the volume $V_{500}$;
Step (iii) Tap the sample 1250 times (500+750) and read the volume $V_{1250}$;
Step (iv) Tap the sample 2500 times (1250+1250) and read the volume $V_{2500}$;
Step (v) If the difference between $V_{500}$ and $V_{1250}$ is more than 2 mL the taps are repeated: i.e. the sample is tapped another 1250 times and repeated until the difference is below 2 mL.

Bulk density=sample weight/volume before tapping.
Tapped density=weight/volume after tapping.
Calculation:

$$\text{Bulk density} = m \,(\text{mg})/V_0 \,(\text{mL})$$

$$\text{Tapped density} = m \,(\text{mg})/V_{2500} \,(\text{mL})$$

See, also, Example 1, infra.

In some embodiments of the kits of the disclosure, the olanzapine has a particle size distribution characterized by a D(90) of from 20 µm to 37 µm, such as, for example, µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, or 37 µm.

In other embodiments of the kits of the disclosure, the olanzapine has a particle size distribution characterized by a D(90) of from about 20 µm to about 37 µm, such as, for example, about 20 µm, about 21 µm, about 22 µm, about 23 µm, about 24 µm, about 25 µm, about 26 µm, about 27 µm, about 28 µm, about 29 µm, about 30 µm, about 31 µm, about 32 µm, about 33 µm, about 34 µm, about 35 µm, about 36 µm, or about 37 µm.

In some embodiments of the kits of the disclosure, the olanzapine has a particle size distribution characterized by a D(90) of from 24 µm to 35 µm, such as, for example, 24 µm, 25 µm, 26 µm, 27 µm, 28 µm, 29 µm, 30 µm, 31 µm, 32 µm, 33 µm, 34 µm, or 35 µm.

In other embodiments of the kits of the disclosure, the olanzapine has a particle size distribution characterized by a D(90) of from about 24 µm to about 35 µm, such as, for example, about 24 µm, about 25 µm, about 26 µm, about 27 µm, about 28 µm, about 29 µm, about 30 µm, about 31 µm, about 32 µm, about 33 µm, about 34 µm, or about 35 µm.

In some embodiments of the kits of the disclosure, the olanzapine has a particle size distribution characterized by a D(3,2) of from 5.5 µm to 7.5 µm, such as, for example, 5.5 µm, 5.6 µm, 5.7 µm, 5.8 µm, 5.9 µm, 6.0 µm, 6.1 µm, 6.2 µm, 6.3 µm, 6.4 µm, 6.5 µm, 6.6 µm, 6.7 µm, 6.8 µm, 6.9 µm, 7.0 µm, 7.1 µm, 7.2 µm, 7.3 µm, 7.4 µm, or 7.5 µm.

In other embodiments of the kits of the disclosure, the olanzapine has a particle size distribution characterized by a D(3,2) of from about 5.5 µm to about 7.5 µm, such as, for example, about 5.5 µm, about 5.6 µm, about 5.7 µm, about 5.8 µm, about 5.9 µm, about 6.0 µm, about 6.1 µm, about 6.2 µm, about 6.3 µm, about 6.4 µm, about 6.5 µm, about 6.6 µm, about 6.7 µm, about 6.8 µm, about 6.9 µm, about 7.0 µm, about 7.1 µm, about 7.2 µm, about 7.3 µm, about 7.4 µm, or about 7.5 µm.

In some embodiments of the kits of the disclosure, the olanzapine has a particle size distribution characterized by a D(3,2) of from 5.8 µm to 7.0 µm, such as, for example, 5.8 µm, 5.9 µm, 6.0 µm, 6.1 µm, 6.2 µm, 6.3 µm, 6.4 µm, 6.5 µm, 6.6 µm, 6.7 µm, 6.8 µm, 6.9 µm, or 7.0 µm.

In other embodiments of the kits of the disclosure, the olanzapine has a particle size distribution characterized by a D(3,2) of from about 5.8 µm to about 7.0 µm, such as, for example, about 5.8 µm, about 5.9 µm, about 6.0 µm, about 6.1 µm, about 6.2 µm, about 6.3 µm, about 6.4 µm, about 6.5 µm, about 6.6 µm, about 6.7 µm, about 6.8 µm, about 6.9 µm, or about 7.0 µm.

In some embodiments of the kits of the disclosure, the tapped density of the olanzapine is from 0.35 g/ml to 0.44 g/ml, such as, for example, 0.35 g/ml, 0.36 g/ml, 0.37 g/ml, 0.38 g/ml, 0.39 g/ml, 0.40 g/ml, 0.41 g/ml, 0.42 g/ml, 0.43 g/ml, or 0.44 g/ml.

In some embodiments of the kits of the disclosure, the tapped density of the olanzapine is from about 0.35 g/ml to about 0.44 g/ml, such as, for example, about 0.35 g/ml, about 0.36 g/ml, about 0.37 g/ml, about 0.38 g/ml, about 0.39 g/ml, about 0.40 g/ml, about 0.41 g/ml, about 0.42 g/ml, about 0.43 g/ml, or about 0.44 g/ml.

In some embodiments of the kits of the disclosure, the olanzapine has a particle size distribution characterized by a D(90) of from about 20 µm to about 37 µm and by a D(3,2) of from about 5.5 µm to about 7.5 µm.

In other embodiments of the kits of the disclosure, the olanzapine has a particle size distribution characterized by a D(90) of from about 20 µm to about 37 µm, and has a tapped density of about 0.35 g/ml to about 0.44 g/ml.

In some embodiments of the kits of the disclosure, the olanzapine has a particle size distribution characterized by a D(3,2) of from about 5.5 µm to about 7.5 µm, and has a tapped density of about 0.35 g/ml to about 0.44 g/ml.

In other embodiments of the kits of the disclosure, the olanzapine has a particle size distribution characterized by a D(90) of from about 20 µm to about 37 µm and by a D(3,2) of from about 5.5 µm to about 7.5 µm, and has a tapped density of about 0.35 g/ml to about 0.44 g/ml.

In some embodiments of the kits of the disclosure, the olanzapine comprises polymorph form II. In some embodiments of the kits of the disclosure, the olanzapine is polymorph form II.

As used herein, olanzapine Form II is the polymorphic form described in U.S. Pat. No. 5,736,541. The Form II polymorph has an XRPD spectrum substantially as shown in FIG. 1. Main typical peaks of olanzapine Form II are defined as peaks at about 8.7, 12.5, 17.4, 19.9, 21.1, 21.6, 22.4, 24.0, 25.3 and 29.8±0.2 deg. 20.

In some embodiments of the kits of the disclosure, the container containing olanzapine is a vial.

In some embodiments of the kits of the disclosure, the container containing olanzapine is a glass vial.

In some embodiments of the kits of the disclosure, the container containing olanzapine is a 10 mL glass vial.

In some embodiments of the kits of the disclosure, the container containing olanzapine is a sterile glass vial.

In some embodiments of the kits of the disclosure, the container containing olanzapine is a 10 mL sterile glass vial.

In some embodiments of the kits of the disclosure, the container containing the mixture of organic solvent, diblock copolymer, and a triblock copolymer, is a syringe.

In some embodiments of the kits of the disclosure, the container containing the mixture of organic solvent, diblock copolymer, and a triblock copolymer, is a 2.0-2.5 mL syringe.

In some embodiments of the kits of the disclosure, the container containing the mixture of organic solvent, diblock copolymer, and a triblock copolymer, is a 2.25 mL syringe.

In some embodiments of the kits of the disclosure, the container containing the mixture of organic solvent, diblock copolymer, and a triblock copolymer, is a sterile syringe.

In some embodiments of the kits of the disclosure, the container containing the mixture of organic solvent, diblock copolymer, and a triblock copolymer, is a sterile 2.0-2.5 mL syringe.

In some embodiments of the kits of the disclosure, the container containing the mixture of organic solvent, diblock copolymer, and a triblock copolymer, is a sterile, 2.25 mL syringe.

In some embodiments of the kits of the disclosure, the container containing the mixture of organic solvent, diblock copolymer, and a triblock copolymer, is a pre-filled syringe.

In some embodiments of the kits of the disclosure, the container containing the mixture of organic solvent, diblock copolymer, and a triblock copolymer, is a prefilled 2.0-2.5 mL syringe.

In some embodiments of the kits of the disclosure, the container containing the mixture of organic solvent, diblock copolymer, and a triblock copolymer, is a prefilled 2.25 mL syringe.

In some embodiments of the kits of the disclosure, the container containing the mixture of organic solvent, diblock copolymer, and a triblock copolymer, is a sterile, pre-filled syringe.

In some embodiments of the kits of the disclosure, the container containing the mixture of organic solvent, diblock copolymer, and a triblock copolymer, is a sterile, prefilled 2.0-2.5 mL syringe.

In some embodiments of the kits of the disclosure, the container containing the mixture of organic solvent, diblock copolymer, and a triblock copolymer, is a sterile, prefilled 2.25 mL syringe.

In some embodiments, the kits of the disclosure further comprise a needle.

The needle is capable of being fitted to the syringe and to allow for subcutaneous injection of the composition of the disclosure. In some embodiments, the needle is a 21 gauge needle.

These embodiments are advantageous over other formulations known in the art, such as, for example, of ZYPREXA RELPREVV®, which requires a much larger bore, 16 gauge needle. The smaller bore, 21 gauge needle generally creates less injection site pain and generates less patient anxiety.

In some embodiments, the needle has a ⅝ inch length. These embodiments are advantageous over other formulations known in the art, such as, for example, ZYPREXA RELPREVV®, which utilizes a 1.5. inch long needle. The shorter needle generally creates less injection site pain and generates less patient anxiety.

In some aspects, the kits of the disclosure are used in preparing a pharmaceutical composition of the disclosure.

In some embodiments, the pharmaceutical compositions of the disclosure are prepared from the kits by 1) charging the contents of the prefilled syringe (organic solvent, diblock copolymer, and a triblock copolymer) into the vial containing olanzapine; 2) mixing the contents of the vial to form the pharmaceutical composition. The composition may then be administered to a patient by withdrawing all or a portion of the composition from the vial using the syringe, and then subcutaneously injecting the composition into the patient In some aspects, the disclosure is directed to methods of preparing a pharmaceutical composition of the disclosure, wherein the methods comprise adding a mixture of the organic solvent, the diblock copolymer, and the triblock copolymer, to solid olanzapine.

In some embodiments of the methods of preparing the pharmaceutical compositions of the disclosure, the olanzapine has a particle size distribution characterized by a D(90) of from about 20 μm to about 37 μm, a particle size distribution characterized by a D(3,2) of from about 5.5 μm to about 7.5 μm, or a tapped density from about 0.35 g/ml to 0.44 g/ml, or any combination thereof.

In some embodiments of the methods of preparing the pharmaceutical compositions of the disclosure, the olanzapine has a particle size distribution characterized by a D(90) of from 20 μm to 37 μm, such as, for example, 20 μm, 21 μm, 22 μm, 23 μm, 24 μm, 25 m, 26 μm, 27 μm, 28 μm, 29 μm, 30 μm, 31 μm, 32 μm, 33 μm, 34 μm, 35 μm, 36 μm, or 37 m.

In some embodiments of the methods of preparing the pharmaceutical compositions of the disclosure, the olanzapine has a particle size distribution characterized by a D(90) of from about 20 μm to about 37 μm, such as, for example, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, or about 37 μm.

In some embodiments of the methods of preparing the pharmaceutical compositions of the disclosure, the olanzapine has a particle size distribution characterized by a D(90) of from 24 μm to 35 μm, such as, for example, 24 μm, 25 μm, 26 μm, 27 μm, 28 μm, 29 m, 30 μm, 31 μm, 32 μm, 33 μm, 34 μm, or 35 μm.

In some embodiments of the methods of preparing the pharmaceutical compositions of the disclosure, the olanzapine has a particle size distribution characterized by a D(90) of from about 24 μm to about 35 μm, such as, for example, about 24 μm, about 25 μm, about 26 μm, about 27 μm, about 28 μm, about 29 μm, about 30 μm, about 31 μm, about 32 μm, about 33 μm, about 34 μm, or about 35 μm.

In some embodiments of the methods of preparing the pharmaceutical compositions of the disclosure, the olanzapine has a particle size distribution characterized by a D(3,2) of from 5.5 μm to 7.5 μm, such as, for example, 5.5 μm, 5.6 μm, 5.7 μm, 5.8 μm, 5.9 μm, 6.0 μm, 6.1 μm, 6.2 μm, 6.3 μm, 6.4 μm, 6.5 μm, 6.6 μm, 6.7 μm, 6.8 μm, 6.9 μm, 7.0 μm, 7.1 μm, 7.2 μm, 7.3 μm, 7.4 μm, or 7.5 μm.

In some embodiments of the methods of preparing the pharmaceutical compositions of the disclosure, the olanzapine has a particle size distribution characterized by a D(3,2) of from about 5.5 μm to about 7.5 μm, such as, for example, about 5.5 μm, about 5.6 μm, about 5.7 μm, about 5.8 μm, about 5.9 μm, about 6.0 μm, about 6.1 μm, about 6.2 μm, about 6.3 μm, about 6.4 μm, about 6.5 μm, about 6.6 μm, about 6.7 μm, about 6.8 μm, about 6.9 μm, about 7.0 μm, about 7.1 μm, about 7.2 μm, about 7.3 μm, about 7.4 μm, or about 7.5 μm.

In some embodiments of the methods of preparing the pharmaceutical compositions of the disclosure, the olanzapine has a particle size distribution characterized by a D(3,2) of from 5.8 μm to 7.0 μm, such as, for example, 5.8 μm, 5.9 μm, 6.0 μm, 6.1 μm, 6.2 μm, 6.3 μm, 6.4 μm, 6.5 μm, 6.6 μm, 6.7 μm, 6.8 μm, 6.9 μm, or 7.0 μm.

In some embodiments of the methods of preparing the pharmaceutical compositions of the disclosure, the olanzapine has a particle size distribution characterized by a D(3,2) of from about 5.8 μm to about 7.0 μm, such as, for example, about 5.8 μm, about 5.9 μm, about 6.0 μm, about 6.1 μm, about 6.2 μm, about 6.3 μm, about 6.4 μm, about 6.5 μm, about 6.6 μm, about 6.7 μm, about 6.8 μm, about 6.9 μm, or about 7.0 μm.

In some embodiments of the methods of preparing the pharmaceutical compositions of the disclosure, the tapped density of the olanzapine is from 0.35 g/ml to 0.44 g/ml, such as, for example, 0.35 g/ml, 0.36 g/ml, 0.37 g/ml, 0.38 g/ml, 0.39 g/ml, 0.40 g/ml, 0.41 g/ml, 0.42 g/ml, 0.43 g/ml, or 0.44 g/ml.

In some embodiments of the methods of preparing the pharmaceutical compositions of the disclosure, the tapped density of the olanzapine is from about 0.35 g/ml to about 0.44 g/ml, such as, for example, about 0.35 g/ml, about 0.36 g/ml, about 0.37 g/ml, about 0.38 g/ml, about 0.39 g/ml, about 0.40 g/ml, about 0.41 g/ml, about 0.42 g/ml, about 0.43 g/ml, or about 0.44 g/ml.

In some embodiments of the methods of preparing the pharmaceutical compositions of the disclosure, the olanzapine has a particle size distribution characterized by a D(90) of from about 20 μm to about 37 μm and by a D(3,2) of from about 5.5 μm to about 7.5 m.

In some embodiments of the methods of preparing the pharmaceutical compositions of the disclosure, the olanzapine has a particle size distribution characterized by a D(90) of from about 20 μm to about 37 μm, and has a tapped density of about 0.35 g/ml to about 0.44 g/ml.

In some embodiments of the methods of preparing the pharmaceutical compositions of the disclosure, the olanzapine has a particle size distribution characterized by a D(3,2) of from about 5.5 μm to about 7.5 μm, and has a tapped density of about 0.35 g/ml to about 0.44 g/ml.

In some embodiments of the methods of preparing the pharmaceutical compositions of the disclosure, the olanzapine has a particle size distribution characterized by a D(90) of from about 20 μm to about 37 μm and by a D(3,2) of from about 5.5 μm to about 7.5 m, and has a tapped density of about 0.35 g/ml to about 0.44 g/ml.

In some embodiments of the methods of preparing the pharmaceutical compositions of the disclosure, the olanzapine comprises polymorph form II. In some embodiments of the methods of preparing the pharmaceutical compositions of the disclosure, the olanzapine is polymorph form II.

In some embodiments of the methods of preparing the pharmaceutical compositions of the disclosure, the mixture of the organic solvent, the diblock copolymer comprising polylactic acid and polyethylene glycol, and the triblock copolymer comprising polylactic acid and polyethylene glycol is added by syringe to the solid olanzapine contained in a vial.

In some aspects, the disclosure is directed to methods of administering olanzapine to a patient, wherein the method comprises subcutaneously injecting the patient with a pharmaceutical composition of the disclosure.

In some aspects, the disclosure is directed to methods of treating a disease or disorder that is schizophrenia, schizoaffective disorder, bipolar disorder, or depression, in a patient in need thereof, wherein the method comprises subcutaneously administering to the patient a pharmaceutical composition of the disclosure.

In a specific embodiment, prior to initiating treatment with the subcutaneous injection, tolerability is established with oral olanzapine treatment.

In some aspects, the disclosed methods comprise subcutaneously injecting the patient a pharmaceutical composition of the disclosure. In such aspects, the subcutaneous injection may be made to any suitable site on the patient's body. In some embodiments, the subcutaneous injection is made in the patient's abdomen. In other embodiments, the subcutaneous injection is made in the patient's upper arm. In other embodiments, the subcutaneous injection is made in the patient's thigh. In other embodiments, the subcutaneous injection is made in the patient's back.

In some embodiments, the disease or disorder is schizophrenia.

In some embodiments, the disease or disorder is schizoaffective disorder.

In some embodiments, the disease or disorder is bipolar disorder.

In some embodiments, the disease or disorder is depression.

In some embodiments of the methods of treatment of the disclosure, the patient has a PANSS total score between 80 and 120, inclusive, prior to subcutaneous administration of the composition of the disclosure (e.g., at the initiation of treatment of a single patient, or at baseline (prior to randomization) for a population of patients) with a score ≥4 on at least 2 of the following 4 items of the PANSS positive subscale: hallucinatory behavior, delusions, conceptual disorganization, or suspiciousness/persecution.

In some aspects of the disclosed methods of treatment, the subcutaneously administered pharmaceutical composition comprises 300 mg-600 mg of olanzapine, such as, for example, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, or 600 mg of olanzapine.

In some embodiments of the disclosed methods of treatment, the subcutaneously administered pharmaceutical composition comprises 300-350 mg, optionally 310-320 mg, of olanzapine, such as, for example, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, or 350 mg.

In some embodiments, the subcutaneously administered pharmaceutical composition comprises about 318 mg of olanzapine. In some embodiments, the subcutaneously administered pharmaceutical composition comprises about 323 mg of olanzapine. In some embodiments, the subcutaneously administered pharmaceutical composition comprises about 328 mg of olanzapine.

In some embodiments of the disclosed methods of treatment, the subcutaneously administered pharmaceutical composition comprises 400-450 mg, optionally 415-435 mg, of olanzapine, such as, for example, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, or 450 mg.

In some embodiments, the subcutaneously administered pharmaceutical composition comprises about 425 mg of olanzapine. In some embodiments, the subcutaneously administered pharmaceutical composition comprises about 430 mg of olanzapine. In some embodiments, the subcutaneously administered pharmaceutical composition comprises about 435 mg of olanzapine.

In some embodiments of the disclosed methods of treatment, the subcutaneously administered pharmaceutical composition comprises 500-550 mg, optionally 520-540 mg, of olanzapine, such as, for example, 500 mg, 501 mg, 502 mg, 503 mg, 504 mg, 505 mg, 506 mg, 507 mg, 508 mg, 509 mg, 510 mg, 511 mg, 512 mg, 513 mg, 514 mg, 515 mg, 516 mg, 517 mg, 518 mg, 519 mg, 520 mg, 521 mg, 522 mg, 523 mg, 524 mg, 525 mg, 526 mg, 527 mg, 528 mg, 529 mg, 530 mg, 531 mg, 532 mg, 533 mg, 534 mg, 535 mg, 536 mg, 537 mg, 538 mg, 539 mg, 540 mg, 541 mg, 542 mg, 543 mg, 544 mg, 545 mg, 546 mg, 547 mg, 548 mg, 549 mg, or 550 mg.

In some embodiments, the subcutaneously administered pharmaceutical composition comprises 531 mg of olanzapine. In some embodiments, the subcutaneously administered pharmaceutical composition comprises about 536 mg of olanzapine. In some embodiments, the subcutaneously administered pharmaceutical composition comprises about 541 mg of olanzapine.

In some aspects of the disclosed methods of treatment, the subcutaneously administered composition comprises about 300 mg—about 600 mg of olanzapine, such as, for example, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 505 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, or about 600 mg of olanzapine.

In some embodiments of the disclosed methods of treatment, the subcutaneously administered composition comprises about 318 mg of olanzapine.

In some embodiments of the disclosed methods of treatment, the subcutaneously administered composition comprises about 425 mg of olanzapine.

In some embodiments of the disclosed methods of treatment, the subcutaneously administered composition comprises about 531 mg of olanzapine.

In some aspects of the disclosed methods of treatment, the subcutaneously administered pharmaceutical composition has a volume of 0.5 mL-2.0 mL, such as, for example, 0.5 mL, 0.6 mL, 0.7 mL, 0.8 mL, 0.9 mL, 1.0 mL, 1.1 mL, 1.2 mL, 1.3 mL, 1.4 mL, 1.5 mL, 1.6 mL, 1.7 mL, 1.8 mL, 1.9 mL, or 2.0 mL.

In some aspects of the disclosed methods of treatment, the subcutaneously administered pharmaceutical composition has a volume of about 0.5 mL—about 2.0 mL, such as, for example, about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, about 1.6 mL, about 1.7 mL, about 1.8 mL, about 1.9 mL, or about 2.0 mL.

In some aspects of the disclosed methods of treatment, the subcutaneously administered pharmaceutical composition has a volume of 0.5 mL-1.8 mL, such as, for example, 0.5 mL, 0.6 mL, 0.7 mL, 0.8 mL, 0.9 mL, 1.0 mL, 1.1 mL, 1.2 mL, 1.3 mL, 1.4 mL, 1.5 mL, 1.6 mL, 1.7 mL, or 1.8 mL.

In some aspects of the disclosed methods of treatment, the subcutaneously administered pharmaceutical composition has a volume of about 0.5 mL—about 1.8 mL, such as, for example, about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, about 1.5 mL, about 1.6 mL, about 1.7 mL, or about 1.8 mL.

In some embodiments of the disclosed methods of treatment, the subcutaneously administered pharmaceutical composition has a volume of 0.9 mL-1.5 mL.

In some embodiments of the disclosed methods of treatment, the subcutaneously administered pharmaceutical composition has a volume of 0.9 mL.

In some embodiments of the disclosed methods of treatment, the subcutaneously administered pharmaceutical composition has a volume of about 0.9 mL.

In some embodiments of the disclosed methods of treatment, the subcutaneously administered pharmaceutical composition has a volume of 1.2 mL.

In some embodiments of the disclosed methods of treatment, the subcutaneously administered pharmaceutical composition has a volume of about 1.2 mL.

In some embodiments of the disclosed methods of treatment, the subcutaneously administered pharmaceutical composition has a volume of 1.5 mL.

In some embodiments of the disclosed methods of treatment, the subcutaneously administered pharmaceutical composition has a volume of about 1.5 mL.

In some aspects of the disclosed methods of treatment, the dose-normalized ratio of $AUC_\infty$ (after a single subcutaneous dose of the pharmaceutical composition) to the $AUC_{tau}$ of oral olanzapine (calculated for 28 days) is between 0.97-1.29.

In some embodiments of the disclosed methods of treatment, the dose-normalized ratio of $AUC^\infty$ (after a single subcutaneous dose of the pharmaceutical composition) to the $AUC_{tau}$ of oral olanzapine (calculated for 28 days) is about 1.1.

In some aspects of the disclosed methods of treatment, administration of the pharmaceutical composition to the patient by subcutaneous injection results in the patient having an olanzapine plasma $C_{max}$ within 11-14 days after administration.

As used herein, the term $C_{max}$ refers to the maximum plasma concentration of olanzapine.

Without intending to be bound by theory, it is believed that upon subcutaneous injection of the pharmaceutical compositions of the disclosure, the organic solvent diffuses away and the block copolymers (which are not soluble in aqueous medium) precipitate thereby forming a depot that entraps the olanzapine. Olanzapine is slowly released from this depot by drug diffusion and/or gradual depot degradation to achieve and maintain therapeutic levels of the drug over a period of time. In some embodiments, the time period is 28 days±5 days, for example 25 days, 26 days, 27 days, 28 days, 29 days, 30 days, or 31 days. In some embodiments, the time period is 30 days or about 30 days. In some embodiments, the time period is 60 days or about 60 days.

In the methods of the disclosure, the pharmaceutical compositions of the disclosure are subcutaneously administered once per month. Thus, a treatment regimen using the compositions of the disclosure comprises a series of monthly subcutaneous injections. Each monthly subcutaneous injection has associated pharmacokinetic parameters, such as, for example, a maximum plasma concentration of olanzapine, $C_{max}$, $t_{max}$, AUC, etc.

In some aspects of the disclosed methods of treatment, the patient reaches a steady-state such that there are not significant changes in the patient's olanzapine pharmacokinetic parameters in consecutive monthly subcutaneous injections. In some embodiments, steady state is reached between the first and second monthly subcutaneous injections. In other embodiments, steady state is reached between the second and third monthly subcutaneous injections.

In some embodiments of the disclosed methods of treatment, the patient reaches a steady-state $C_{max}$, such that there is no significant change in the olanzapine $C_{max}$ in consecutive monthly subcutaneous injections. In some embodiments, steady state is reached after the second monthly subcutaneous injection. In other embodiments, steady state is reached after the third monthly subcutaneous injection.

In some aspects of the disclosed methods of treatment, administration of the pharmaceutical composition to the patient by subcutaneous injection results in the patient having an olanzapine plasma $C_{max}$ of less than 100 ng/mL.

In some aspects of the disclosed methods of treatment, administration of the pharmaceutical composition to the patient by subcutaneous injection results in the patient having an olanzapine plasma $C_{max}$ of less than 100 ng/mL after the first subcutaneous injection.

In some aspects of the disclosed methods of treatment, administration of the pharmaceutical composition to the patient by subcutaneous injection results in the patient having an olanzapine plasma $C_{max}$ of less than 100 ng/mL after the second subcutaneous injection.

In some aspects of the disclosed methods of treatment, administration of the pharmaceutical composition to the patient by subcutaneous injection results in the patient having an olanzapine plasma $C_{max}$ of less than 100 ng/mL after the third subcutaneous injection.

In some aspects of the disclosed methods of treatment, administration of the pharmaceutical composition to the patient by subcutaneous injection results in the patient having an olanzapine plasma $C_{max}$ of less than 90 ng/mL.

In some aspects of the disclosed methods of treatment, administration of the pharmaceutical composition to the patient by subcutaneous injection results in the patient having an olanzapine plasma $C_{max}$ of less than 90 ng/mL after the first subcutaneous injection.

In some aspects of the disclosed methods of treatment, administration of the pharmaceutical composition to the patient by subcutaneous injection results in the patient having an olanzapine plasma $C_{max}$ of less than 90 ng/mL after the second subcutaneous injection.

In some aspects of the disclosed methods of treatment, administration of the pharmaceutical composition to the patient by subcutaneous injection results in the patient having an olanzapine plasma $C_{max}$ of less than 90 ng/mL after the third subcutaneous injection.

In some aspects of the disclosed methods of treatment, administration of the pharmaceutical composition to the patient by subcutaneous injection results in the patient having an olanzapine plasma $C_{max}$ of less than 80 ng/mL.

In some aspects of the disclosed methods of treatment, administration of the pharmaceutical composition to the patient by subcutaneous injection results in the patient having an olanzapine plasma $C_{max}$ of less than 80 ng/mL after the first subcutaneous injection.

In some aspects of the disclosed methods of treatment, administration of the pharmaceutical composition to the patient by subcutaneous injection results in the patient having an olanzapine plasma $C_{max}$ of less than 80 ng/mL after the second subcutaneous injection.

In some aspects of the disclosed methods of treatment, administration of the pharmaceutical composition to the patient by subcutaneous injection results in the patient having an olanzapine plasma $C_{max}$ of less than 80 ng/mL after the third subcutaneous injection.

In some aspects of the disclosed methods of treatment, administration of the pharmaceutical composition to the patient by subcutaneous injection results in the patient having an olanzapine plasma $C_{max}$ of less than 70 ng/mL.

In some aspects of the disclosed methods of treatment, administration of the pharmaceutical composition to the patient by subcutaneous injection results in the patient having an olanzapine plasma $C_{max}$ of less than 70 ng/mL after the first subcutaneous injection.

In some aspects of the disclosed methods of treatment, administration of the pharmaceutical composition to the patient by subcutaneous injection results in the patient having an olanzapine plasma $C_{max}$ of less than 70 ng/mL after the second subcutaneous injection.

In some aspects of the disclosed methods of treatment, administration of the pharmaceutical composition to the patient by subcutaneous injection results in the patient having an olanzapine plasma $C_{max}$ of less than 70 ng/mL after the third subcutaneous injection.

In some aspects of the disclosed methods of treatment, administration of the pharmaceutical composition to the patient by subcutaneous injection results in the patient having an olanzapine plasma $C_{max}$ of less than 60 ng/mL.

In some aspects of the disclosed methods of treatment, administration of the c pharmaceutical composition to the patient by subcutaneous injection results in the patient having an olanzapine plasma $C_{max}$ of less than 60 ng/mL after the first subcutaneous injection.

In some aspects of the disclosed methods of treatment, administration of the pharmaceutical composition to the patient by subcutaneous injection results in the patient having an olanzapine plasma $C_{max}$ of less than 60 ng/mL after the second subcutaneous injection.

In some aspects of the disclosed methods of treatment, administration of the pharmaceutical composition to the patient by subcutaneous injection results in the patient having an olanzapine plasma $C_{max}$ of less than 60 ng/mL after the third subcutaneous injection.

In some aspects of the disclosed methods of treatment, administration of the pharmaceutical composition to the patient by subcutaneous injection results in the patient having an olanzapine plasma $C_{max}$ of less than 50 ng/mL.

In some aspects of the disclosed methods of treatment, administration of the pharmaceutical composition to the patient by subcutaneous injection results in the patient having an olanzapine plasma $C_{max}$ of less than 50 ng/mL after the first subcutaneous injection.

In some aspects of the disclosed methods of treatment, administration of the pharmaceutical composition to the patient by subcutaneous injection results in the patient having an olanzapine plasma $C_{max}$ of less than 50 ng/mL after the second subcutaneous injection.

In some aspects of the disclosed methods of treatment, administration of the pharmaceutical composition to the patient by subcutaneous injection results in the patient having an olanzapine plasma $C_{max}$ of less than 50 ng/mL after the third subcutaneous injection.

In some aspects of the disclosed methods of treatment, administration of the pharmaceutical composition to the patient by subcutaneous injection results in the patient having an olanzapine plasma $C_{max}$ of less than 40 ng/mL.

In some aspects of the disclosed methods of treatment, administration of the pharmaceutical composition to the patient by subcutaneous injection results in the patient having an olanzapine plasma $C_{max}$ of less than 40 ng/mL after the first subcutaneous injection.

In some aspects of the disclosed methods of treatment, administration of the pharmaceutical composition to the patient by subcutaneous injection results in the patient having an olanzapine plasma $C_{max}$ of less than 40 ng/mL after the second subcutaneous injection.

In some aspects of the disclosed methods of treatment, administration of the pharmaceutical composition to the patient by subcutaneous injection results in the patient having an olanzapine plasma $C_{max}$ of less than 40 ng/mL after the third subcutaneous injection.

In some aspects of the disclosed methods of treatment, administration of the pharmaceutical composition to the patient by subcutaneous injection results in the patient having an olanzapine plasma concentration of at least 10 ng/mL for at least 21 days of the 30 days following the injection. In these aspects, the 21 days during which the olanzapine plasma concentration is at least 10 ng/mL are not necessarily the first 21 days of the 30 days following the injection, and are not necessarily a contiguous 21 day period.

In some aspects of the disclosed methods of treatment, administration of the pharmaceutical composition to the patient by subcutaneous injection results in the patient having an olanzapine plasma concentration of at least 20 ng/mL for at least 21 days of the 30 days following the injection. In these aspects, the 21 days during which the olanzapine plasma concentration is at least 20 ng/mL are not necessarily the first 21 days of the 30 days following the injection, and are not necessarily a contiguous 21 day period.

In some aspects of the disclosed methods of treatment, administration of the pharmaceutical composition to the patient by subcutaneous injection results in the patient having an olanzapine plasma concentration of at least 10 ng/mL for at least 30 days of the 30 days following the injection.

In some aspects of the disclosed methods of treatment, administration of the pharmaceutical composition to the patient by subcutaneous injection results in the patient having an olanzapine plasma concentration of at least 20 ng/mL for at least 30 days of the 30 days following the injection.

In some aspects, the disclosure is directed to methods of treating a patient with olanzapine comprising a) providing a kit of the disclosure; b) withdrawing the mixture of organic solvent, diblock copolymer, and triblock copolymer from the container in the kit containing said mixture; c) adding the mixture from b) to the container in the kit containing olanzapine and then mixing to form a subcutaneous olanzapine pharmaceutical composition; and d) subcutaneously administering the subcutaneous olanzapine pharmaceutical composition to the patient in need of olanzapine treatment; wherein the treatment is effective in treating the patient for about one month.

In some aspects of the disclosed methods of treatment, administration of the pharmaceutical composition to the patient by subcutaneous injection results in the patient having a lower score on the Positive and Negative Syndrome Scale (PANSS) than the patient had prior to receiving the subcutaneous injection of the composition. In some aspect, the disclosed methods of treatment are superior to placebo in reducing the PANSS total score, for example a reduction relative to placebo of 1, 2, 3, 4, 5, 6, 7, 8, 9, 10, 11, 12, 13, 14, 15, 16. 17, 18, 19 or 20 points, preferably at least 6 points, more preferably at least 8 points, most preferably at least 10 points.

The PANSS is a 30-item scale used to evaluate positive and negative symptoms of schizophrenia (Kay S R, Fiszbein A, Opler L A. The positive and negative syndrome scale (PANSS) for schizophrenia. Schizophr Bull 1987; 13(2): 261-76.) The PANSS is used to identify the presence and severity of psychopathology symptoms, the relationship of these symptoms to one another, and the global psychopathology. Each item is scored on a 7-point scale ranging from 1 (absent) to 7 (extreme). The positive symptom scale includes 7 items with a maximum score of 49; the negative symptom scale includes 7 items with a maximum score of 49; and the general psychopathology scale includes 16 items with a maximum score of 112.

In some aspects of the disclosed methods of treatment, administration of the pharmaceutical composition to the patient by subcutaneous injection results in the patient having a lower score on the Clinical Global Impression-Improvement (CGI-I) scale than the patient had prior to receiving the subcutaneous injection of the composition.

The CGI-I scale permits a global evaluation of the patient's overall improvement in symptoms. The CGI-I scale rates the patient's improvement relative to his or her symptoms on a 7-point scale ranging from 1 (very much improved) to 7 (very much worse). See Guy, W. ECDEU Assessment Manual for Psychopharmacology (revised). Rockville (Maryland): US Department of Health, Education, and Welfare; Public Health service; Alcohol, Drug Abuse, and Mental Health Administration; National Institute of Mental Health, Psychopharmacology Research Branch. 1976b; 218-22.

In some aspects of the disclosed methods of treatment, administration of the pharmaceutical composition to the patient by subcutaneous injection results in the patient having a lower score on the Clinical Global Impression—Severity of Illness Scale (CGI-S) scale than the patient had prior to receiving the subcutaneous injection of the composition.

The CGI-S allows a rater to assess the patient's current severity of illness on a scale of 1 to 7, where 1=normal/not at all ill, 2=borderline mentally ill, 3=mildly ill, 4=moderately ill, 5=markedly ill, 6=severely ill, and 7=among the most extremely ill patients. See Guy, W. ECDEU Assessment Manual for Psychopharmacology (revised). Rockville (Maryland): US Department of Health, Education, and Welfare; Public Health service; Alcohol, Drug Abuse, and Mental Health Administration; National Institute of Mental Health, Psychopharmacology Research Branch. 1976b; 218-22.

In some aspects of the disclosed methods of treatment, administration of the pharmaceutical composition to the patient by subcutaneous injection results in the patient having a lower score on the Patient Global Impression-Improvement (PGI-I) than the patient had prior to receiving the subcutaneous injection of the composition.

The PGI-I scale is a 1-item patient-rated instrument that measures improvement of the patient's disease; the patient rates the perceived change in his/her condition in response to therapy. The patient is instructed to select a response option on a scale of 1 to 7, where 1=very much better, 2=much better, 3=a little better, 4=no change, 5=a little worse, 6=much worse, 7=very much worse. See Steinert T, Eisele F, Langle G, Albani C, Flammer E, Borbé R. [PGI-I (patient's global impression) as an outcome and quality indicator of psychiatric in-patient treatment: results and concordance with doctor's assessments]. Psychiatr Prax 2010; 37(7):343-9.

In some aspects of the disclosed methods of treatment, administration of the pharmaceutical composition to the patient by subcutaneous injection results in the patient having a higher score on the Personal and Social Performance Scale (PSP) than the patient had prior to receiving the subcutaneous injection of the composition.

The PSP is a clinician-rated instrument that measures personal and social functioning in patients with schizophrenia. See Morosini P L, Magliano L, Brambilla L, Ugolini S, Pioli R. Development, reliability and acceptability of a new version of the DSM-IV Social and Occupational Functioning Assessment Scale (SOFAS) to assess routine social functioning. Acta Psychiatr Scand 2000 April; 101(4):323-9. The PSP is a 100-point single-item rating scale, divided into 10 equal intervals. The score is based on the assessment of patient's functioning in 4 categories: 1) socially useful activities, including work and study; 2) personal and social relationships; 3) self-care; and 4) disturbing and aggressive behaviors.

Higher scores represent better personal and social functioning, with ratings from 91 to 100 indicating more than adequate functioning, while scores under 30 indicate functioning so poor that intensive supervision is required.

In some aspects of the disclosed methods of treatment, administration of the pharmaceutical composition to the patient by subcutaneous injection results in the patient having a lower score on the Schizophrenia Quality of Life Scale (SQLS) Revision 4 than the patient had prior to receiving the subcutaneous injection of the composition.

The Schizophrenia Quality of Life Scale (SQLS) Revision 4 (Martin C R, Allan R. Factor structure of the Schizophrenia Quality of Life Scale Revision 4 (SQLS-R4). Psychol Health Med 2007; 12(2):126-34) is a 33-item measure that yields 3 subscale scores: psychosocial, motivation/energy, and symptoms/side effects. See Wilkinson G, Hesdon B, Wild D, Cookson R, Farina C, Sharma V, et al. Self-report quality of life measure for people with schizophrenia: the SQLS. Br J Psychiatry 2000; 177:42-6. Higher scores on the scales indicate worse quality of life.

In some aspects of the disclosed methods of treatment, administration of the pharmaceutical composition to the patient by subcutaneous injection results in the patient having a lower score on the 3-Level EuroQol Five Dimensions Questionnaire (EQ-5D-3L).

The 3-Level EuroQol Five Dimensions Questionnaire (EQ-5D-3L) is a standardized questionnaire that assesses overall state of health. The EQ-5D-3L consists of 2 parts. In Part 1, patients rate their health state in 5 domains (mobility, self-care, usual activities, pain/discomfort, and anxiety/depression) using a scale of 1 to 3, where 1=no problems, 2=some problems, and 3=extreme problems. In Part 2, patients rate their health state on a visual analog scale numbered from 0 to 100; a rating of 0 represents the worst imaginable health state, and a rating of 100 represents the best imaginable health state. See EuroQol Group. EuroQol—a new facility for the measurement of health-related quality of life. Health Policy 1990; 16:199-208; Rabin R, de Charro F. EQ-5D: a measure of health status from the EuroQol Group. Ann Med 2001; 33(5):337-43.

In some aspects of the disclosed methods of treatment, administration of the pharmaceutical composition results in the patient having a $D_2$-receptor occupancy of 60-80%, optionally 65-80%, optionally 65-70%, as determined by positron emission tomography (PET).

The level of dopamine D2 receptor occupancy (D2RO) is recognized as one of the drivers of the clinical efficacy and safety response to antipsychotic drugs. The currently accepted hypothesis is that the D2RO receptor occupancy in the striatum should lie between 60 and 80% for optimal antipsychotic effect and minimal side effects; the lower threshold is required for clinical efficacy, whereas exceeding the higher threshold leads to an increased risk of side effects, in particular, extrapyramidal symptoms (EPS). The relationship between olanzapine concentrations and the striatal D2RO receptor occupancy was described by an Emax model:

$$D2RO = RO \max \frac{Cp}{Kd + Cp}$$

where D2RO is the dopamine D2 receptor occupancy, Cp is the olanzapine plasma concentration and Kd is the apparent equilibrium dissociation constant, which is the active moiety plasma concentration at which 50% D2 receptor occupancy is observed. ROmax is the maximal receptor occupancy that can be achieved. As for most antipsychotics, the value of ROmax was fixed to 100% in the model. The Kd parameter value was estimated to 11 ng/mL (Mamo D et al, D2 receptor occupancy of olanzapine pamoate depot using positron emission tomography: an open-label study in patients with schizophrenia. Neuropsychopharmacology. 2008 January; 33(2):298-304.)

In some aspects, the disclosure is directed to methods of switching a patient from a daily oral olanzapine therapy to a pharmaceutical composition of the disclosure wherein the method comprises i) orally administering a final administration of the daily oral olanzapine therapy, after which no further oral olanzapine therapy is administered; and the next day subcutaneously administering to the patient a pharmaceutical composition of the disclosure; thereby switching the subject from a daily oral olanzapine therapy to a long acting injectable olanzapine formulation.

In some aspects, the disclosure is directed to methods of switching a patient from a daily oral olanzapine therapy to a pharmaceutical composition of the disclosure wherein the method comprises i) orally administering a final administration of the daily oral olanzapine therapy, after which no further oral olanzapine therapy is administered; and then from 2 to 7 days after the final oral dose subcutaneously administering to the patient a pharmaceutical composition of the disclosure; thereby switching the subject from a daily oral olanzapine therapy to a long acting injectable olanzapine formulation.

In other aspects, the disclosure is directed to methods of switching a patient from a long acting intramuscular injectable olanzapine formulation to a pharmaceutical composition of the disclosure without a need for supplemental oral olanzapine therapy wherein the method comprises administering a final dose the long acting intramuscularly injectable olanzapine formulation; and at the next dosing, optionally one month after the preceding dose when the preceding dose is a once monthly dose, or optionally two weeks after the preceding dose when the preceding dose is a once every two-weeks dose, subcutaneously administering the pharmaceutical composition of the disclosure; wherein the method is performed without administering to the patient a supplemental oral olanzapine therapy.

Further provided is a method switching a patient from a long acting intramuscular injectable olanzapine formulation to a pharmaceutical composition of the disclosure, comprising:
  a) administering the final dose the long acting intramuscularly injectable olanzapine formulation; and
  b) at the next dosing, administering to the patient a pharmaceutical composition of the disclosure wherein:
    the final dose of the long acting intramuscular injectable olanzapine formulation comprises 150 mg of olanzapine and the pharmaceutical composition of the disclosure comprises 318 mg of olanzapine; or
    wherein the final dose of the long acting intramuscular injectable olanzapine formulation comprises 300 mg of olanzapine and the pharmaceutical composition of the disclosure comprises 318 mg of olanzapine; or
    wherein the final dose of the long acting intramuscular injectable olanzapine formulation comprises 210 mg of olanzapine and the pharmaceutical composition of the disclosure comprises 425 mg of olanzapine; or
    wherein the final dose of the long acting intramuscular injectable olanzapine formulation comprises 405 mg of olanzapine and the pharmaceutical composition of the disclosure comprises 425 mg of olanzapine; or
    wherein the final dose of the long acting intramuscular injectable olanzapine formulation comprises 405 mg of olanzapine and the pharmaceutical composition of the disclosure comprises 531 mg of olanzapine.

In embodiments of the above methods, after switching there are no clinically meaningful changes from baseline in psychiatric, neurological, and clinical symptoms and subjects remain clinically stable.

As used in this context, the phrase "at the next dosing" refers to the dosing event at which the next dose of the long acting intramuscular injectable olanzapine formulation would be administered if the long acting intramuscular injectable olanzapine formulation were not being discontinued. In some embodiments the long acting intramuscular injectable olanzapine formulation is ZYPREXA RELPREVV®. In some embodiments the long acting intramuscular injectable olanzapine formulation is a once-monthly dose. In other embodiments the long acting intramuscular injectable olanzapine formulation is a once-every two weeks dose.

In some aspects, the disclosure is directed to methods of treating an olanzapine naïve patient, comprising administering to the patient an oral daily dose of 10 mg-20 mg olanzapine for 2 consecutive days to assess the patient's tolerance of olanzapine, and if the patient tolerates the oral olanzapine, then subcutaneously administering a pharmaceutical composition of the disclosure. As used herein, an "olanzapine naïve patient" is a patient to whom olanzapine has not been previously administered.

The methods of treatment disclosed herein provide safe and effective treatment of schizophrenia, schizoaffective disorder, bipolar disorder, or depression. The efficacy of the disclosed methods may be demonstrated by the clinical instruments described herein (e.g., PANSS, CGI-S, etc.).

The safety of the disclosed methods may be demonstrated by one or more of: lack of serious adverse events, lack of extrapyramidal symptoms, lack of injection pain and other injection site reactions [local tolerability]), vital signs (blood pressure, pulse and orthostatic changes, and temperature), body weight, laboratory tests, electrocardiogram, concomitant medication use, time to all-cause discontinuation, all-cause discontinuation rates and discontinuation rates due to adverse events (tolerability), and the following rating scales: Abnormal Involuntary Movement Scale, Simpson-Angus Scale, Barnes Akathisia Rating Scale, Columbia Suicide Severity Rating Scale, and Calgary Depression Scale for Schizophrenia.

In some embodiments, the subject has an increase in body mass of less than 10%, optionally less than 9%, optionally less than 8%, optionally less than 7%, optionally less than 6%, optionally less than 5% relative to their body mass at the start of the method of treatment. The body mass of the subject is typically measured over the time period of the method of treatment. The body mass can be measured over a time period of 8, 48 or 56 weeks.

The safety of the disclosed methods is such that in some embodiments of the disclosed methods, monitoring the patient for PDSS is unnecessary. In these embodiments, the administering physician is not required to monitor the patient for PDSS.

EXAMPLES

List of Abbreviations

| Abbreviation | Term |
| --- | --- |
| AIMS | Abnormal Involuntary Movement Scale |
| ALT | Alanine aminotransferase |
| ALT | alanine aminotransferase |
| API | Active pharmaceutical ingredient |
| AST | aspartate aminotransferase |
| AUC | area under the plasma concentration-time curve |
| $AUC_{0-28}$ | Area under the plasma concentration-time curve from time 0 to 28 days after study drug administration |
| $AUC_{0-30}$ | Area under the plasma concentration-time curve from time 0 to 30 days after study drug administration |
| $AUC_{0-60}$ | Area under the plasma concentration-time curve from time 0 to 60 days after study drug administration |
| $AUC_{0-tau}$ | Area under the plasma concentration-time curve from time 0 to the end of the study drug administration period |
| $AUC_{tau}$ | area under the plasma drug concentration-time curve over dosing interval |
| BAN | British Approved Name |
| BARS | Barnes Akathisia Rating Scale |
| BMI | Body mass index |
| BPRS | Brief Psychiatric Rating Scale |
| BPRS-C | Anchored Version of the Brief Psychiatric Rating Scale for Children |
| $C_{28}$ | Plasma drug concentration after 28 days of study drug administration |
| CAS | Chemical Abstracts Service |
| CATIE | Clinical Antipsychotic Trials of Intervention Effectiveness |
| $C_{av}$ | Average observed plasma drug concentration |
| CDMS | clinical data management system |
| CDSS | Calgary Depression Scale for Schizophrenia |
| CFR | Code of Federal Regulations (USA) |
| CGI | Clinical Global Impression |
| CGI-I | Clinical Global Impression-Improvement |
| CGI-S | Clinical Global Impression-Severity |
| $C_{max}$ | Maximum observed plasma drug concentration |
| $C_{max}$ | maximum observed drug concentration |
| CNS | Central nervous system |
| COVID-19 | coronavirus disease 2019 |
| CPK | Creatine phosphokinase |
| CRF | case report form (refers to any media used to collect study data [ie, paper or electronic]) |
| CRO | contract research organization |
| CSR | clinical study report |
| C-SSRS | Columbia Suicide Severity Rating Scale |
| $C_{trough}$ | Trough plasma drug concentration |
| CV % | Percentage coefficient of variation |
| CYP | Cytochrome P450 |
| D2 | Dopamine |
| D2RO | Dopamine D2 receptor occupancy |
| DMSO | Dimethyl sulfoxide |
| DSM | Diagnostic and Statistical Manual of Mental Disorders |
| DSM-5 | Diagnostic and Statistical Manual of Mental Disorders, $5^{th}$ Edition |
| $EC_{50}$ | Effective concentration in 50% of the population |
| ECG | Electrocardiogram |
| $ED_{50}$ | Effective dose in 50% of the population |
| EOT | end-of-treatment |
| EPS | Extrapyramidal symptoms |
| EQ-5D-3L | 3-Level EuroQol Five Dimensions Questionnaire |
| ET | early termination |
| EU | European Union |
| EO | Ethylene oxide |
| FDA | United States Food and Drug Administration |
| FSH | follicle-stimulating hormone |
| FU | follow-up (period) |
| GABA | Gamma-aminobutyric acid |
| GCP | Good Clinical Practice |
| GGT | Gamma-glutamyl transferase |
| GLP | Good Laboratory Practice |
| GMP | Good Manufacturing Practices |
| GPSP | Global Patient Safety and Pharmacovigilance |
| $HbA_{1c}$ | Glycated hemoglobin |
| HDL | High density lipoprotein |
| HIV | human immunodeficiency virus |
| IB | Investigator's Brochure |
| ICE | intercurrent event |
| ICF | informed consent form |
| ICH | The International Council for Harmonisation of Technical Requirements for Pharmaceuticals for Human Use |
| IDMC | Independent Data Monitoring Committee |
| IEC | Independent Ethics Committee |
| $I_{Kr}$ | Delayed rectifier potassium current |
| im | Intramuscular |
| IMP | investigational medicinal product |
| INN | International Non-Proprietary Name |
| ip | Intraperitoneal |
| IRB | Institutional Review Board |
| ISR | injection site reaction |
| IUPAC | International Union of Pure and Applied Chemistry |
| iv | Intravenous |
| Ki | Binding affinity |
| K-SADS-PL | Kiddie Schedule for Affective Disorders and Schizophrenia for School Aged Children-Present and Lifetime Version |
| LA | Lactic acid |
| LA/EO | Lactic acid/ethylene oxide |
| LAI | Long-acting injectable |
| LC/MS/MS | Liquid chromatography/tandem mass spectrometry |
| LDL | Low density lipoprotein |
| LSO | local safety officer |
| M&S | Modeling and simulations |
| MAR | missing at random |
| MM | medical monitor |
| MMRM | mixed-model repeated measures |
| MNAR | missing not at random |
| mPEG-PDL | Methoxy-poly(ethylene glycol)-co-poly(D,L-lactide) |
| n | Number |
| NCA | noncompartmental analysis |
| NMDA | N-methyl-D-aspartate |
| NMS | Neuroleptic malignant syndrome |
| NOAEL | No observable adverse effect level |
| $OLA_{10}$ | Oligomeric lactic acid |
| OLAI | olanzapine long-acting injection |
| PANSS | Positive and Negative Syndrome Scale |
| PCP | Phencyclidine |
| PDAESI | protocol-defined adverse event of special interest |

-continued

| Abbreviation | Term |
|---|---|
| PDL-PEG-PDL | Poly(D,L-lactide)-co-poly(ethylene glycol)-co-poly(D,L-lactide) |
| PDSS | Post-injection Delirium/Sedation Syndrome |
| PEG | Polyethylene glycol |
| PET | Positron emission tomography |
| PFS | Prefilled syringe |
| PGI-I | Patient Global Impression-Improvement |
| pKa | Dissociation constant |
| PLA | Poly(lactic acid) |
| PP | per-protocol |
| PPI | Prepulse inhibition |
| PSP | Personal and Social Performance Scale |
| q1m | once monthly |
| RDQ | Readiness for Discharge Questionnaire |
| RER | Respiratory exchange ratio |
| RNA | ribonucleic acid |
| RSI | reference safety information |
| RTSM | Randomization and Trial Supply Management |
| SANS | Scale for Assessing Negative Symptoms |
| SAR | Serious adverse reaction |
| SAS | Simpson-Angus Scale |
| sc | Subcutaneous |
| SCID-5-CT | Structured Clinical Interview for DSM-5, Clinical Trials Version |
| SmPC | Summary of Product Characteristics |
| SOP | Standard Operating Procedure |
| SQLS | Schizophrenia Quality of Life Scale |
| SUSAR | Suspected unexpected serious adverse reactions |
| TC | Teleconference |
| $t_{max}$ | Time to maximum observed drug concentration |
| UK | United Kingdom |
| ULN | upper limit of normal |
| US | United States (of America) |
| US(A) | United States (of America) |
| USAN | United States Adopted Name |
| USP | United States Pharmacopoeia |
| USPI | United States Prescribing Information |
| VC | Videoconference |
| WBC | White blood cells |
| β-HCG | Beta-human chorionic gonadotropin |

For reference, the pharmacokinetics and dose proportionality of IM olanzapine are given:

Intramuscular Olanzapine Pharmacokinetics

Immediate release im injection (ZYPREXA INTRAMUSCULAR) results in rapid absorption with peak plasma concentrations occurring within 15 to 45 minutes. Based upon a pharmacokinetic study in healthy volunteers, a 5-mg dose of im olanzapine for injection produces, on average, a maximum plasma concentration approximately 5 times higher than the maximum plasma concentration produced by the equivalent dose of oral olanzapine. AUC achieved after an im dose is similar to that achieved after oral administration of the same dose. The half life observed after im administration is similar to that observed after oral dosing. The pharmacokinetic profile is linear over the clinical dosing range. Metabolic profiles after im administration are qualitatively similar to metabolic profiles after oral administration.

Extended release (slow dissolution) im injection (ZYPREXA RELPREVV® [olanzapine pamoate]) results in prolonged systemic olanzapine plasma concentrations for weeks to months. The fundamental pharmacokinetic properties of olanzapine are similar for ZYPREXA RELPREVV® and daily orally administered olanzapine. The change to a slow release, rate controlled absorption process is the only fundamental pharmacokinetic difference between the administration of ZYPREXA RELPREVV® and orally administered olanzapine. ZYPREXA RELPREVV® injection every 2 or 4 weeks provides olanzapine plasma concentrations that are similar to those achieved by daily doses of oral olanzapine. The steady state plasma concentrations for ZYPREXA RELPREVV® for doses of 150 mg to 405 mg every 2 or 4 weeks are within the range of steady state olanzapine plasma concentration known to have been associated with oral doses of 5 to 20 mg olanzapine once daily. The effective half life for olanzapine after im ZYPREXA RELPREVV® administration is approximately 30 days as compared to a half life after oral administration of approximately 30 hours. Exposure to olanzapine may persist for a period of months after a ZYPREXA RELPREVV® injection. The long persistence of systemic concentrations of olanzapine may be an important consideration for the long term clinical management of the patient. Typical systemic olanzapine plasma concentrations reach a peak within the first week after injection and are at trough level immediately prior to the next injection. The olanzapine plasma concentration fluctuation between the peak and trough is comparable to the peak and trough fluctuations associated with once daily oral dosing.

Dose Proportionality and Oral Dose Correspondence

ZYPREXA RELPREVV® is available at the following dosing regimens: 150 mg/2 wks, 300 mg/4 wks, 210 mg/2 wks, 405 mg/4 wks, or 300 mg/2 wks. An injection of a larger dose produces a dose proportional increase in the systemic exposure. The olanzapine exposure of ZYPREXA RELPREVV® corresponds to the oral doses of olanzapine and dose regimen as detailed in the following Table of Recommended Dosing for ZYPREXA PELPREVV Based on Correspondence to Oral ZYPREXA Doses

| Target Oral ZYPREXA Dose (mg/day) | Dosing of ZYPREXA RELPREVV ® During the First 8 Weeks | Maintenance Dose After 8 Weeks of ZYPREXA RELPREVV ® Treatment |
|---|---|---|
| 10 | 210 mg/2 weeks or 405 mg/4 weeks | 150 mg/2 weeks or 300 mg/4 weeks |
| 15 | 300 mg/2 weeks | 210 mg/2 weeks or 405 mg/4 weeks |
| 20 | 300 mg/2 weeks | 300 mg/2 weeks |

Source: ZYPREXA RELPREVV ® USPI 2018

Example 1: Material

Copolymers were synthesized according to the method described in the U.S. Pat. No. 6,350,812, incorporated herein by reference, with minor modifications. Typically, the necessary amount of PEG (gives the triblock co-polymer) or methoxy-PEG (gives the diblock copolymer) was heated at 65° C. and dried under vacuum for 2 hours in a reactor vessel. D,L-lactide (corresponding to the targeted lactic acid/ethylene oxide (LA/EO) molar ratio) and zinc lactate (1/1000 of amount of lactide) were added. The reaction mixture was first dehydrated by three short vacuum/N2 cycles. The reaction mixture was heated at 140° C. and rapidly degassed under vacuum. The reaction was conducted for four days at 140° C. under constant nitrogen flow (0.2 bar). The reaction was cooled to room temperature and its content was dissolved in acetone and then subjected to precipitation with ethanol. The product obtained was subsequently dried under reduced pressure. Alternatively, the copolymers may be purchased from Corbion.

The product obtained was characterized by $^1$H NMR for its residual lactide content and for the determination of the LA/EO molar ratio. $^1$H NMR spectroscopy was performed using a Brucker Advance 300 MHz spectrometer. For all $^1$H NMR spectrograms, TopSpin software was used for the integration of PLA and PEG characteristic peaks and their analyses. Chemical shifts were referenced to the δ=7.26 ppm solvent value of CDCl$_3$.

The product obtained were further characterized by gel permeation chromatography (GPC) for the determination of its molecular weight distribution. GPC was performed using a LC system equipped with a refractive index detector. The equipment can be equipped with a series of Waters styragel columns selected from HR4, HR3 HR2 and HR1 kept at constant temperature. The sample are run in BHT-stabilized THF at a constant flow rate. Molecular weights distributions (Mn; Mw and polydispersity index) are determined by conventional calibration using polystyrene calibration standards.

Olanzapine polymorph form II was used. Characterization includes X-ray diffraction analysis (XRD), particle size distribution, and bulk/tapped density.

A typical XRD profile obtained is shown in FIG. 1. Main typical peaks of olanzapine Form II are defined as peaks at about 8.7, 12.5, 17.4, 19.9, 21.1, 21.6, 22.4, 24.0, 25.3 and 29.8±0.2 deg. 2θ.

For the purposes herein, particle size distribution (PSD) is determined as the percent volume, i.e. D(90) and D(3,2) and was measured by laser diffraction using a Malvern Mastersizer 2000 equipped with a Hydro 2000 S dispersion unit.

The measurements were performed in saturated water dispersion medium (refractive index=1.22 (general purpose)). The samples were added as concentrated suspension under stirring until an obscuration rate of 10-20% was reached. The results were values arising from ten measurement cycles with a recirculation time (after sonification) of 30 sec. The following parameters were used:
Dispersion unit: Hydro 2000 S
Measuring range: 0.02-2000 µm
Analysis model: General purpose, normal, Mie model
Sensitivity: Normal
Particle shape: Irregular
Sample refractive index: 1.709
Absorption: 0.01
Dispersant: Olanzapine saturated water dispersion medium
Dispersion medium refractive index: 1.330
Obscuration: 10-20%
W Pump/stirrer speed: 2500 rpm
Level sensor threshold: 64%
Sample measurement time: 10 s
Background measurement time: 10 s
Repeated measurements (per aliquot): 10
Internal ultrasound: 30 s at 90% power
Recirculation time (after sonication): 30 s
Number of measurements (aliquots): 1

Sample preparation: Samples were prepared as concentrated suspensions. About 50-100 mg of the olanzapine sample was added with a spatula to a small sized glass beaker and several drops of saturated water dispersion medium was added. A paste was obtained by mild mixing, and an additional quantity (1 ml) of saturated water dispersion medium was added in order to obtain a concentrated homogeneous suspension.

Bulk density/tapped density were determined by European Pharmacopoeia 2.9.34. Method 1 (https://www.drugfuture.com/Pharmacopoeia/EP7/DATA/20934E.PDF; PDF downloaded Nov. 14, 2021).

The bulk and tapped densities were determined using the Tapped Density Tester SVM 122 from ERWEKA, equipped with a 100 mL glass cylinder. Approximately 30 g of the powder was carefully poured into the 100 mL measuring cylinder with a funnel. Bulk density was calculated by dividing the amount of powder (in gram) by the measured volume (mL). The tapped density was then determined as follows:

$$\text{Tap } 10x - \text{Read volume}( = V10)$$

$$\text{Tap } 500x(10 + 490) - \text{Read volume}( = V500)$$

$$\text{Tap } 1250x(500 + 750) - \text{Read volume}( = V1250)$$

$$\text{Tap } 2500x(1250 + 1250) - \text{Read volume}( = V2500)$$

If the difference between V500 and V1250 was greater than 2 mL, taps were repeated: i.e. tapped another 1250× and repeated until the difference was below 2 mL.

Bulk density=sample weight/volume before tapping.

Tapped density=weight/volume after tapping.

Calculation:

$$\text{Bulk density} = m\,(\text{mg})/V0\,(\text{mL})$$

$$\text{Tapped density} = m\,(\text{mg})/V2500\,(\text{mL})$$

Example 2

A pharmacokinetics study was performed on young naïve female dogs of around 8 kg with a selection of test items. Six animals were assigned to each treatment group and identified before study start.

Animals of control group (group 1) received repeated intramuscular administrations of ZYPADHERA (which is identical to ZYPREXA RELPREVV® sold in the United States) in the femoral muscles every 2 weeks for 2 months. Reconstitution of the reference product was performed according to the instructions described in the SPC (summary of product characteristics) to achieve a 150 mg/mL concentration of olanzapine. 300 mg of olanzapine (2 mL) were administered per animal per injection using a 19G 1"½ needle.

Animals of group 2 to 5 received a single subcutaneous injection of corresponding test item. Olanzapine dose was fixed at 405 mg and volume of administration was adjusted based of the test item composition. Test items were reconstituted shortly before administration and injected using a 21G 1" needle. The injection of test item of group 3 was reported to be harder compared to the ones of other groups and therefore not optimal.

Table 2.1 presents an overview of the PK study design.

TABLE 2.1

| Group | Test item | Dose (mg) | Route of admin | Dose regimen | OLZ content (wt %) | DMSO content (wt %) | NMP content (wt %) | Volume of injection (mL) |
|---|---|---|---|---|---|---|---|---|
| 1 | Zyp-Adhera ® | 300 | IM | Every 2 W | 150 mg/mL | N/A | N/A | 2.00 |

TABLE 2.1-continued

| | | | | | | | | |
|---|---|---|---|---|---|---|---|---|
| 2 | A | 405 | SC | Single | 22.0% | 60.0 | N/A | 1.60 |
| 3 | B | 405 | SC | Single | 40.7% | 37.1 | N/A | 0.80 |
| 4 | C | 405 | SC | Single | 22.0% | 50.0 | 10.0 | 1.65 |
| 5 | D | 405 | SC | Single | 30.5% | 53.5 | N/A | 1.10 |

| Group | Test item | Triblock Content (wt. %) | Triblock Mn (kDa) | Triblock f(PLA) (%) | Diblock Content (wt. %) | Diblock Mn (kDa) | Diblock f(PLA) (wt. %) |
|---|---|---|---|---|---|---|---|
| 1 | ZypAdhera® | N/A | N/A | N/A | N/A | N/A | N/A |
| 2 | A | 3.6 | 16.1 | 85 | 14.4 | 9.9 | 75 |
| 3 | B | 4.5 | 9.6 | 87 | 17.8 | 9.9 | 75 |
| 4 | C | 3.6 | 16.1 | 85 | 14.4 | 9.9 | 75 |
| 5 | D | 3.2 | 9.6 | 87 | 12.8 | 9.9 | 75 |

N/A: Not applicable
f(PLA)—fraction (wt. %) of polymer that is polylactic acid

The diblock copolymer consists of polylactic acid and polyethylene glycol and has a number average molecular weight of 6.5 to 15 kg/mol and comprising 70%-90% by weight (w/w) polylactic acid. The triblock copolymer consists of polylactic acid and polyethylene glycol and has a number average molecular weight of 6 to 15 kg/mol and comprising 80%-90% by weight (w/w) polylactic acid. In these experiments, the diblock copolymer was kept constant and two different triblock copolymers, having different number average molecular weights, were tested.

The first day of treatment was designated as day 0 (D0) and blood samples were collected as follows:

Group 1: before each injection and 1 h, 3 h, 6 h, 12 h, 24h (D1), 48h (D2), 72h (D3), 144h (D6), 216h (D9), 288h (D12) after each IM administration;

Groups 2-5: before each injection and 1 h, 3 h, 6 h, 12 h, 24h (D1), 48h (D2), 72h (D3), 144h (D6), 216h (D9), 288h (D12), 360h (D15), 432h (D18), 504h (D21), 576h (D24), 648h (D27), 720h (D30), 792h (D33), 864h (D36), 936h (D39), 1008h (D42), 1080h (D45), 1152 (D48), 1224 (D51), 1296 (D54), 1368 (D57), and 1440 (D60) after SC administration. After centrifugation, the plasma was collected into tubes containing $K_2$-EDTA and stored at −80° C. until analysis by LC MS/MS.

Figure 2:
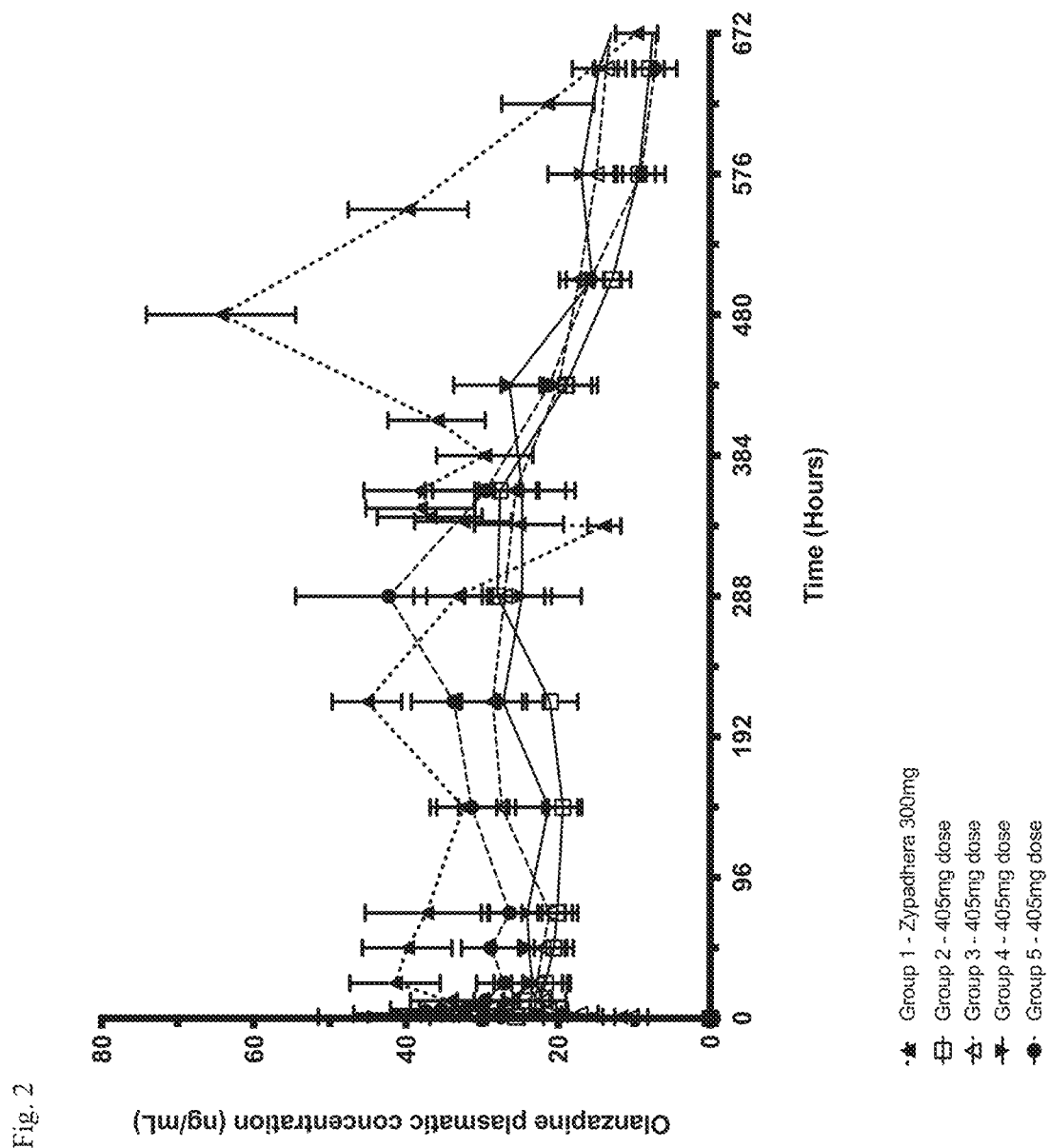
FIG. 2 shows a plot of Mean (±SD) Olanzapine Plasma Concentrations versus time following 1 single subcutaneous administration of different compositions at a 405 mg dose or after 2 repeated intramuscular administrations every 2 weeks of ZYPADHERA product at a 300 mg dose. The study is further described in Example 2. SD=standard deviation

Results of the study are presented in FIG. 2 and Table 2.2.

1-month period, the mean plasma levels of olanzapine obtained after subcutaneous injections were generally within the range of mean plasma levels in control group for which 2 administrations were performed. The mean plasma profiles of the different test items maintained near steady exposure for nearly 3 weeks post-injection, followed by a slow rate of decrease in plasma levels. The $C_{max}$ values after SC administration of the different formulations were below the $C_{max}$ of the reference, ZypAdhera.

Example 3

Effect of Heating or Rubbing of Injection Site on PK of Formulation 1 in Male SD-IGS Rats The purpose of this study was to evaluate the effect of extrinsic factors, heating and rubbing at the site of injection, under clinical-like conditions, on olanzapine PK profile during the first 24 hours post-dose, following Formulation 1 single sc administration in male SD-IGS rats.

Test Item D is representative of Formulation 1, which is a pharmaceutical composition of the disclosure comprising: 30%-32% (w/w) of olanzapine; 52%-54% (w/w) of dimethyl sulfoxide; 12%-14% (w/w) of a diblock copolymer comprising polylactic acid and polyethylene glycol and having a

TABLE 2.2

| Group | Test item | Tmax[1] (h) | Cmax[2] (ng/mL) | Cmin[3] (ng/mL) | AUC$_{0-30\,D}$[4] (ng · h/mL) |
|---|---|---|---|---|---|
| 1 | ZypAdhera®-1st injection | 60 (24-288) | 60.3 ± 8.0 | 14.0 ± 5.3 | 24258 ± 5008** |
|   | ZypAdhera®-2nd injection | 144 (6-216) | 68.5 ± 19.3 | 9.7 ± 6.8 | |
| 2 | A | 3 (1-360) | 41.6 ± 20.4 | 6.8 ± 4.4 | 12863 ± 4132 |
| 3 | B | 180 (144-288) | 31.7 ± 12.9 | 11.9 ± 2.6 | 15256 ± 3534 |
| 4 | C | 2 (1-432) | 52.1 ± 10.2 | 9.8 ± 6.6 | 15240 ± 42440 |
| 5 | D | 96 (1-288) | 54.0 ± 20.7 | 6.8 ± 6.4 | 16704 ± 4619 |

[1]Median (Min-Max) are reported for $T_{max}$
[2], [3], [4]Mean ± SD
[3]$C_{30\,D}$ for SC; $C_{trough}$ for IM
**$AUC_{0-28\,D}$ As observed in FIG. 2, the mean PK profile confirmed the capability of the 4 compositions tested to release olanzapine for the target time period of 1 month. For all the SC formulations tested, the plasma concentrations were quantifiable after 1 month and were close to the $C_{trough}$ values obtained after im injection. Additionally, during this number average molecular weight of 6.5 to 12.5 kg/mol and comprising 75%-84% by weight (w/w) polylactic acid; and 3%-3.5% (w/w) of a triblock copolymer comprising polylactic acid and polyethylene glycol and having a number average molecular weight of 6 to 13 kg/mol and comprising 83%-88% by weight (w/w) polylactic acid; and wherein the diblock copolymer and triblock copolymer together comprise 15%-17.5% by weight (w/w) of the composition.

The study included 3 groups in total with 6 animals per group. The study design is presented in Table 3.1

TABLE 3.1

Study - Experimental Design

| Group number | Animal number | Route | Procedure after sc administration | Administration volume (µL/animal) |
|---|---|---|---|---|
| 1 | 1-6 | sc | Injection site intact (no palpation) | 70 |
| 2 | 7-12 | | Injection site rubbing 15 s, 10 min post-injection | 70 |
| 3 | 13-18 | | Injection site heating 15 min (40-42° C.), 10 min post-injection | 70 | sc = subcutaneous

All groups were given 70 µL Formulation 1 sc doses for a target dose of 80 mg/kg, maximum Formulation 1 tolerated dose in SD-IGS rats.

Blood samples were collected from the tail vein (serial sampling) of all animals using a serial collection scheme with the following time-points: pre-dose, 10 (for groups 1 and 2 only), 30 minutes and 1, 2, 4, 4.5, 5.5, 12, 24, 48, and 72 hours post-dose.

Olanzapine was present in all post-dose plasma samples, starting at 10 minutes and ending at 24 hours in all samples of the animals.

Low variability in exposure parameters (14-35%) was observed in all groups. In all groups, olanzapine plasma concentrations increased immediately, reaching $C_{max}$ within 10 min post-dose, followed by a decline to a plateau concentration up to 72 h.

In most of the animals in the study, $C_{max}$ occurred before the challenge, therefore, any variations in $C_{max}$ cannot be related to the challenge. In some animals, moderate elevation in olanzapine plasma concentrations was observed after the challenge with an insignificant effect on the exposure.

Small spikes in olanzapine plasma concentrations were observed in some of the animals, none can be related to the challenge, followed by a parallel elimination compared to the other individuals in the group, suggesting no dose dumping occurred.

All groups had the same exposure as indicated by the similar AUC0-72h values.

In conclusion, extreme manipulation of injection site of Formulation 1, either heating or rubbing 0.5 h or 4 h post-injection, did not have an effect on the PK of olanzapine in rats or on injection site local tolerability, supporting the conclusion that dose dumping with Formulation 1 is unlikely in humans. Dose dumping is a phenomenon in which there is premature and excessive release of a drug. This can significantly increase drug concentration in the plasma, which can lead to side effects and possible drug-induced toxicity.

Example 4

Following promising PK results from the study described in Examples 2 and 3, further studies in humans were performed with Formulation 1.

The drug product is intended for reconstitution. Vehicle containing the excipients is used for reconstitution.

Phase 1 clinical supplies include the following components:
- One single use vial containing olanzapine powder or empty vial (for use in placebo administration)
- One single use PFS containing vehicle (diluent)
- Two 16-gauge needles for reconstitution, one for adding the vehicle into the vial and one for withdrawing the drug product (Formulation 1) once reconstituted into the dosing syringe
- One luer lock disposable syringe with luer lock tip
- One 21-gauge, 16 mm hypodermic safety needle with needle protection device for sc administration.

The drug product olanzapine for extended release injectable suspension (Formulation 1) and vehicle should be stored between 2° C. and 8° C. At the prescribed storage conditions API (olanzapine) is a yellow powder, and the vehicle is frozen, opaque solid. Prior to reconstitution, both components need to be conditioned at room temperature, and at those conditions, the drug product is a yellow powder, and the vehicle is a clear, colorless solution. After reconstitution of drug product (i.e., drug substance powder with vehicle), a yellow, opaque suspension is obtained.

Example 5

This study was an open-label, SAD, and MAD study to evaluate the safety, tolerability, and PK of Formulation 1 in healthy subjects and patients with a diagnosis of schizophrenia or schizoaffective disorder. Healthy subjects received subtherapeutic Formulation 1 doses of up to 105 mg and patients received therapeutic doses of up to 566 mg. Patients were clinically stable and not currently on antipsychotic treatment other than oral olanzapine. Subjects and patients who met screening eligibility were assigned to 1 of 8 active cohorts, or the Vehicle Cohort, as detailed in Table 5.1 below.

TABLE 5.1

Treatment Allocations for Study

| Cohort | N | Oral Olanzapine (mg/day) | FORMULATION 1 Dosing Regimen |
|---|---|---|---|
| Vehicle | 6 | N/A | Vehicle sc (abdomen) × 3 doses (healthy subjects) |
| 1 | 11 | 2.5 | 70 mg sc (abdomen) × 1 dose (healthy subjects) |
| 2 | 8 | 5 | 105 mg sc (abdomen) × 1 dose (healthy subjects) |
| 3 | 11 | 5 | 105 mg sc (upper arm) × 1 dose (healthy subjects) |
| 4 | 14 | 10 | 425 mg sc (abdomen) × 1 dose (patients) |
| 5 | 14 | 15 | 318 mg sc (abdomen) × 1 dose (patients) |
| 6 | 14 | 20 | 531 mg sc (abdomen) × 1 dose (patients) |
| 8 | 14 | 10 | 283 mg sc (abdomen) q1m × 3 doses (patients) |
| 9 | 15 | 20 | 566 mg sc (abdomen) q1m × 3 doses (patients) |

N/A = not applicable; sc = subcutaneous; q1m = once monthly.

All cohorts included assessments of safety, tolerability, and intensive PK sampling.

Except for the starting dose of 70 mg, the study followed an adaptive design in which the decision to dose-escalate with Formulation 1 was based on a review of the PK and safety data from the preceding lower dose of Formulation 1.

Study Results

Subjects and patients in all cohorts were dosed as set out in Table 5.1; none of the stopping rules from the protocol were met.

Demographics 127 healthy subjects and patients met entry criteria and were considered to be eligible for enrollment into Period 1 of the study (oral olanzapine treatment period).

A total of 36 healthy subjects and 91 patients (54 patients randomized to single-dose Formulation 1 treatment and 37 patients randomized to multiple-dose Formulation 1 treatment) were enrolled during Period 1 of the study.

During Period 2, a total of 30 healthy subjects and 71 patients received at least 1 dose of Formulation 1 and were included in each of the Enrolled, Safety, and Pharmacokinetic Analysis Sets. A further 6 healthy subjects were randomized to a vehicle treatment group in Period 2 of the study.

Pharmacokinetics

During the study conduct the washout period between oral olanzapine last dose and Formulation 1, administration was reduced from 7 days to 2 days in single dose patient cohorts (4 and 5) and multiple dose cohorts (8 and 9). Adjustment of carry over effect of oral olanzapine concentration residues on Formulation 1 was not performed for the non-compartmental analysis. This approach was considered valid because the remaining residue of olanzapine following last oral dose is expected to be eliminated within hours after Formulation 1 dosing. Therefore, its impact on the PK parameters of Formulation 1 is expected to be minimal.

Oral Olanzapine Pharmacokinetics

Oral olanzapine (Zyprexa®) was administered at subtherapeutic doses to healthy subjects (2.5 and 5 mg/day) and to patients at therapeutic doses (10, 15, and 20 mg/day) for 7 days. An extensive PK collection scheme was applied following the last oral dose to fully characterize the PK at steady-state.

Figure 3:
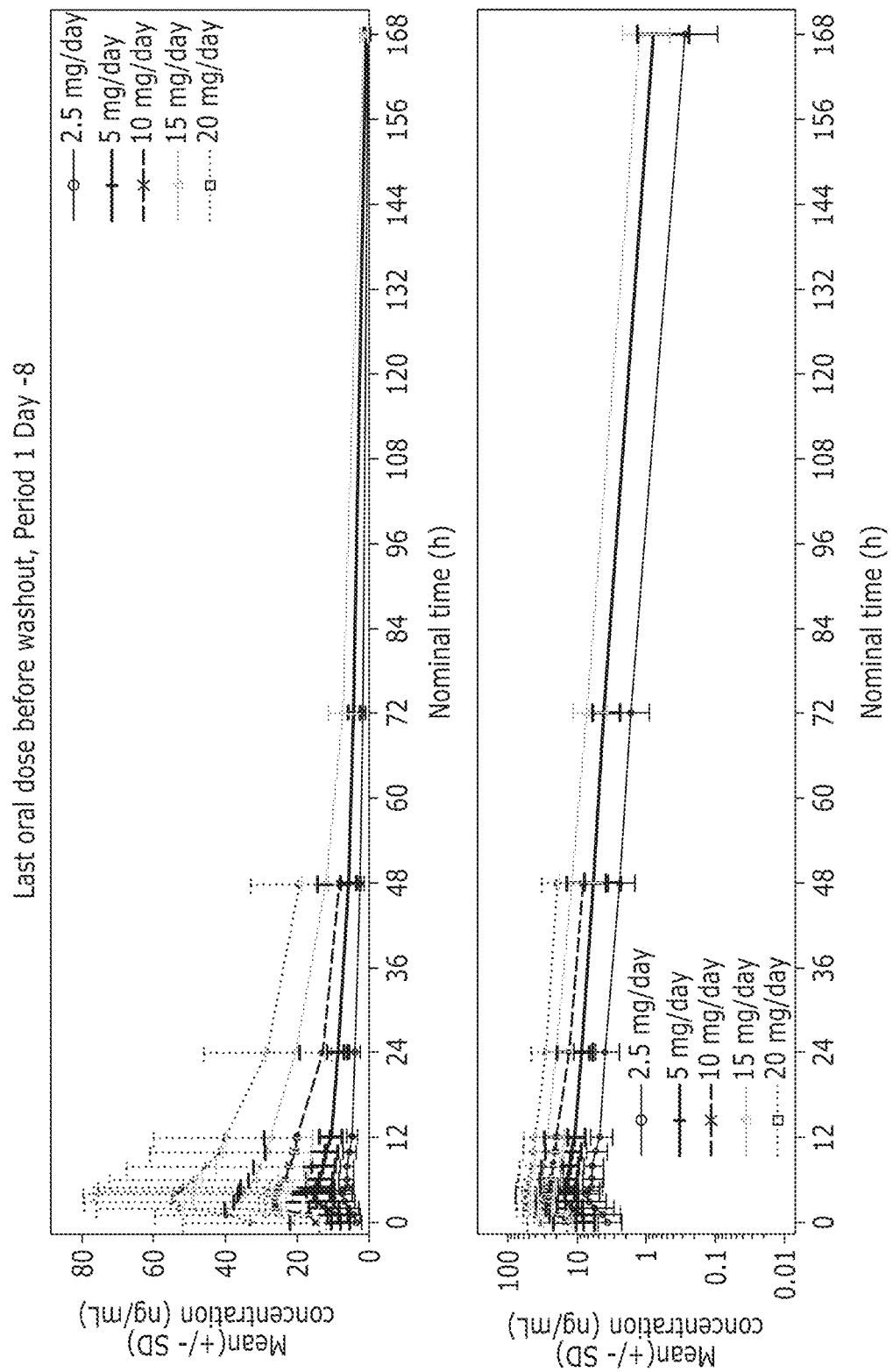
FIG. 3 shows a plot of Mean (+/−SD) Olanzapine Plasma Concentrations Versus Time on a Linear (upper) and Semi-log (lower) Scale by Dosing Day: Following Oral Olanzapine Concentration at Steady State and Washout Period—Safety Analysis Set from the study described in Example 5. SD=standard deviation.

Oral data PK parameters obtained in are summarized in FIG. 3. The PK parameters and inter-individual variability are in alignment with the published data for oral olanzapine (Zyprexa®).

The systemic exposure (i.e., $C_{max}$, $AUC_{\tau,ss}$) of olanzapine increased with dose in a dose-proportional manner over the 2.5 to 20 mg range Formulation 1 Single-Dose Pharmacokinetics (Healthy Subjects and Patients)

Figure 4:
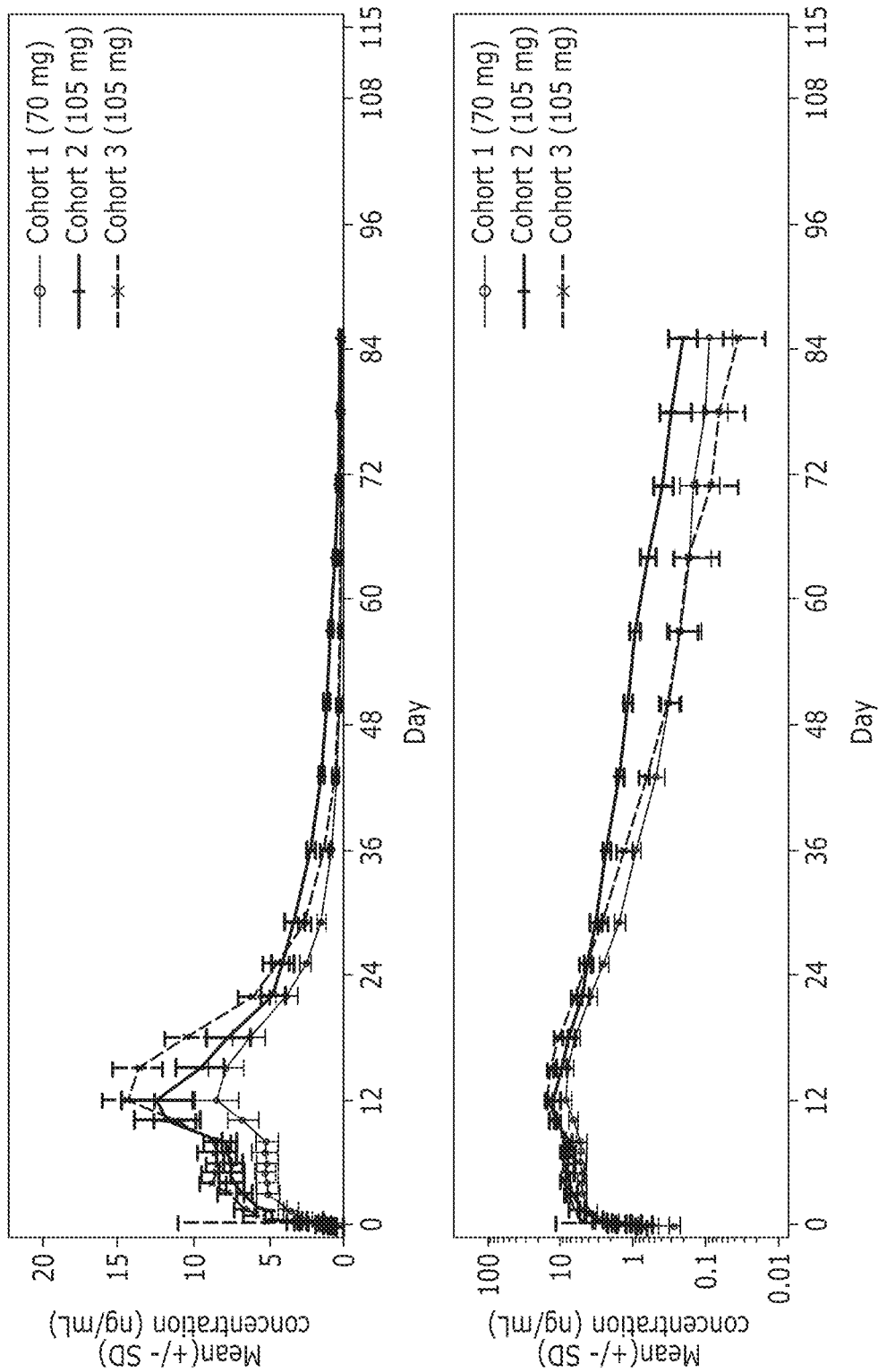
FIG. 4 shows the Mean (±SD) Plasma Olanzapine Concentrations (ng/mL) in Healthy Subjects Following Formulation 1 Single Subcutaneous Dose Administration on a Linear (Upper) and Semi-log (Lower) Scale from the study described in Example 5. SD=standard deviation.
Figure 5:
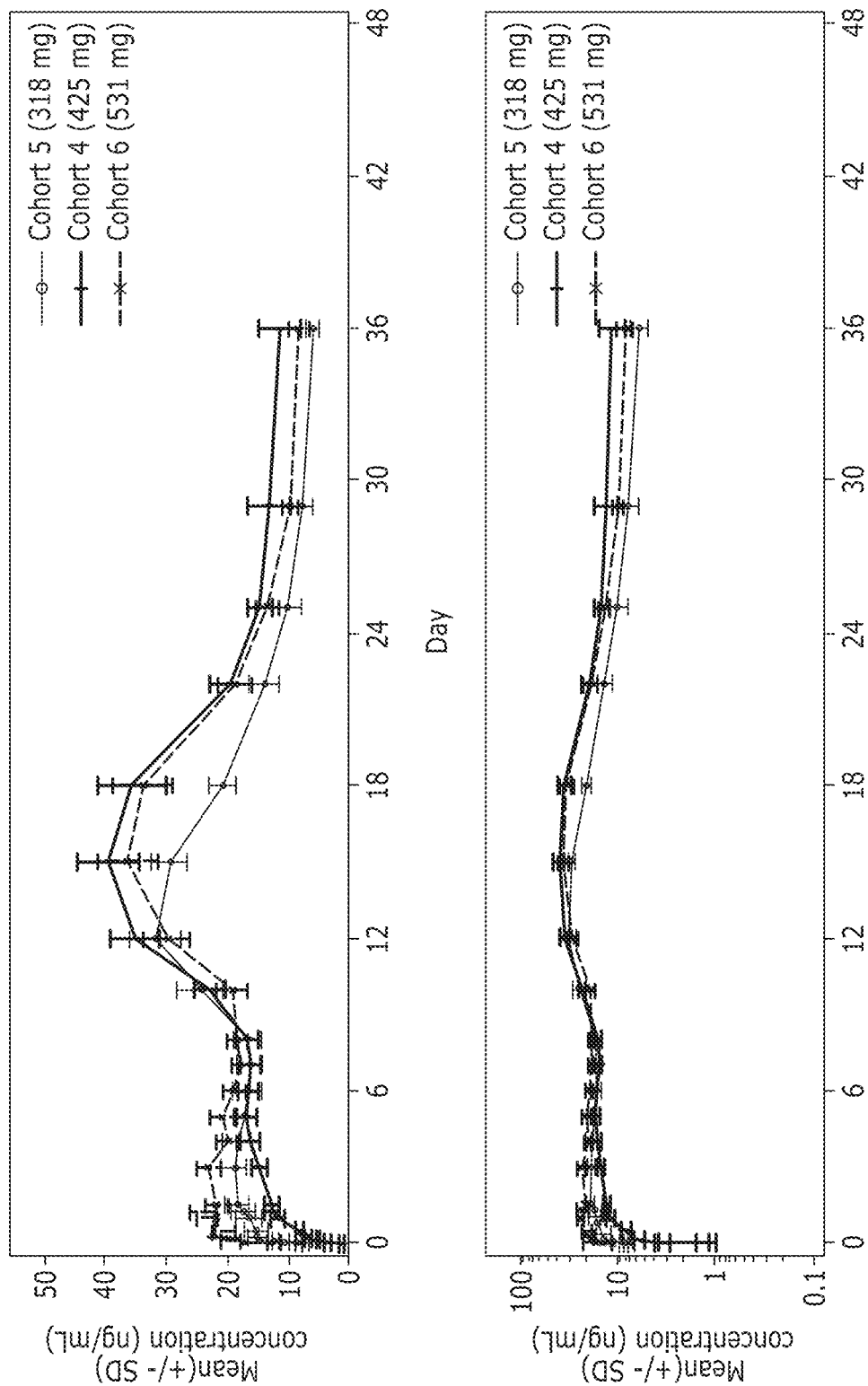
FIG. 5 shows the Mean (±SD) Plasma Olanzapine Concentrations (ng/mL) in Patients Following FORMULATION 1 Single Subcutaneous Dose Administration on a Linear (Upper) and Semi-log (Lower) Scale from the study described in Example 5. SD=standard deviation.

Olanzapine PK profiles following administration of single ascending doses of Formulation 1 via sc injection are displayed in FIG. 4 for healthy subjects and in FIG. 5 for patients.

In general, the Formulation 1 PK profiles were qualitatively similar in healthy subjects and patients. Formulation 1 presented an initial rapid increase in olanzapine plasma concentrations that reached clinically relevant levels (≥10 ng/mL; Meyer and Stahl 2021) within 1-2 days following Formulation 1 administration to patients enrolled in cohorts 4-6. The profile demonstrated initial immediate-release attributes, with gradual increases in plasma concentration and no abrupt spikes or unexplained increase in olanzapine exposure, suggesting that no dose dumping occurred after the Formulation 1 sc injection, which is in agreement with the preclinical studies.

Olanzapine plasma levels increased gradually, reaching a maximum ($C_{max}$) within 11-14 days (ie, 264-336 hours) after dosing with doses of 318 mg to 531 mg. The slow absorption of olanzapine following Formulation 1 sc administration is reflected in a long apparent terminal half-life (flip-flop kinetics). Arithmetic mean $t_{1/2}$ values of the therapeutic Formulation 1 single-dose cohorts (Cohorts 4 to 6) ranged from 11 to 17 days (264 to 406 hours) depending on the dose. Therapeutic levels were maintained over the dosing interval of 28 days for clinically relevant doses; thereafter, concentrations declined in an apparently multiphasic manner until the last sample collection time point of 84 days (cohorts 1-4) or 42 days (Cohort 5 and Cohort 6).

Injection Site Interchangeability

In the study, a dose of 105 mg Formulation 1 was administered sc to the abdomen (Cohort 2) and to the upper arm (Cohort 3) to investigate comparability in exposures. The 2 injection sites showed similar PK profiles. The rate of absorption of olanzapine in the abdomen was similar to absorption in the arm, with median $t_{max}$ values of 263 and 264 hours, respectively. The mean ratios of $C_{max}$ and $AUC_{0-28d}$ were approximately 38% and 20% higher, respectively, following sc administration to the upper arm compared with their corresponding values after sc injection into the abdomen. Importantly, $AUC_{0-t}$ and $AUC_{0-\infty}$ exhibited similar exposures for the 2 injection sites. Therefore, the exposure to Formulation 1 following administration via these 2 injection sites was considered to be comparable.

Formulation 1 Multiple-Dose Pharmacokinetics (Patients)

The multiple-dose PK of olanzapine was evaluated following administration of either 283 or 566 mg of Formulation 1 for 3 consecutive q1m injections in patients (Cohorts 8 and 9, respectively). Mean concentration versus time plots for olanzapine following the third sc injection are displayed in FIGS. 6 and 7.

In multiple-dose cohorts, the 3 doses of Formulation 1 were administered on day 1, day 29 (week 4) and day 57 (week 8), respectively.

Figure 6:
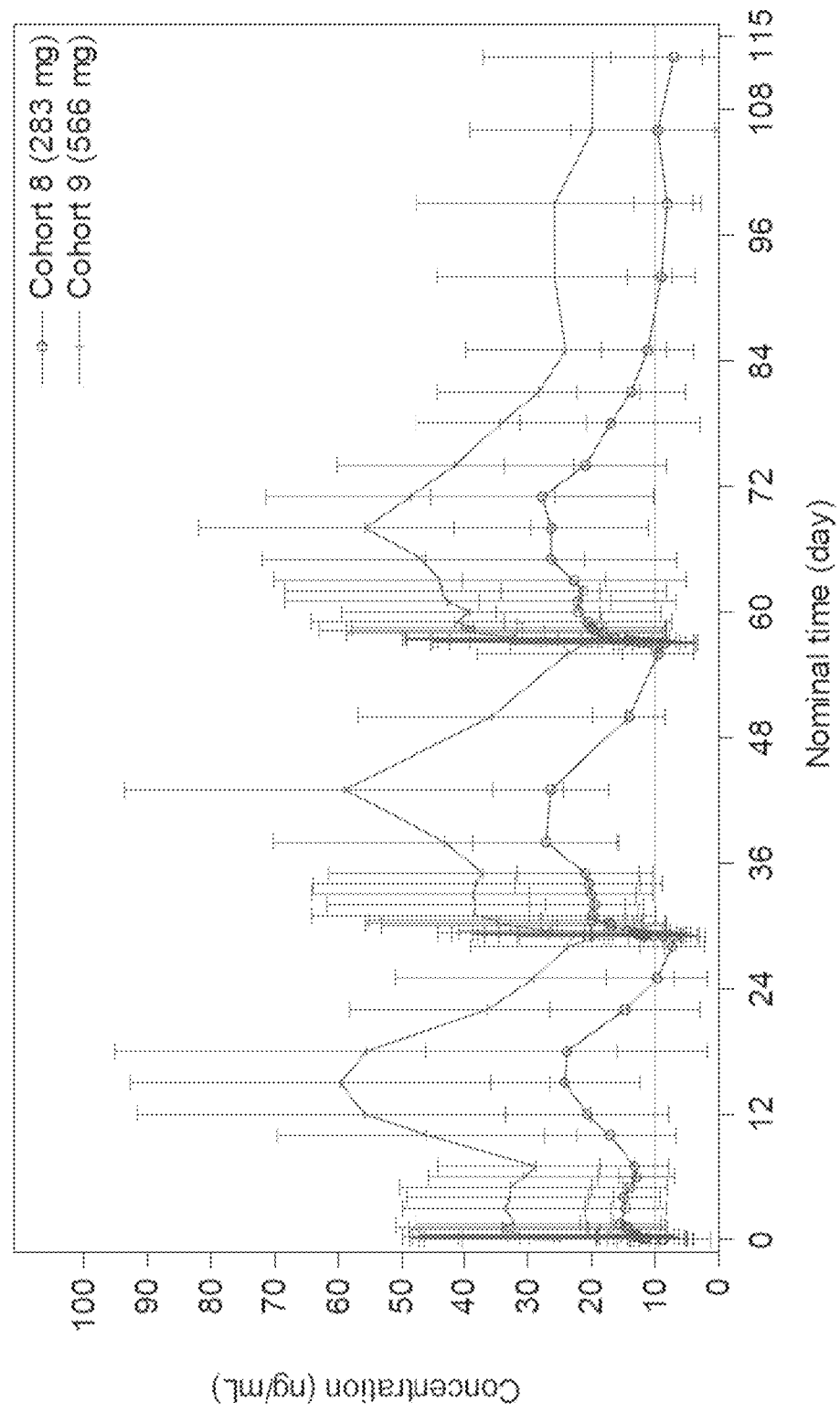
FIG. 6 shows the Mean (±Standard Deviation) Olanzapine Plasma Concentrations Versus Time on a Linear Scale by Cohort and Dosing Day: Multiple-Dose Patient Cohorts Following Formulation 1 (Safety Analysis Set). The horizontal line represents the clinically relevant olanzapine plasma concentration of 10 ng/mL.
Figure 7:
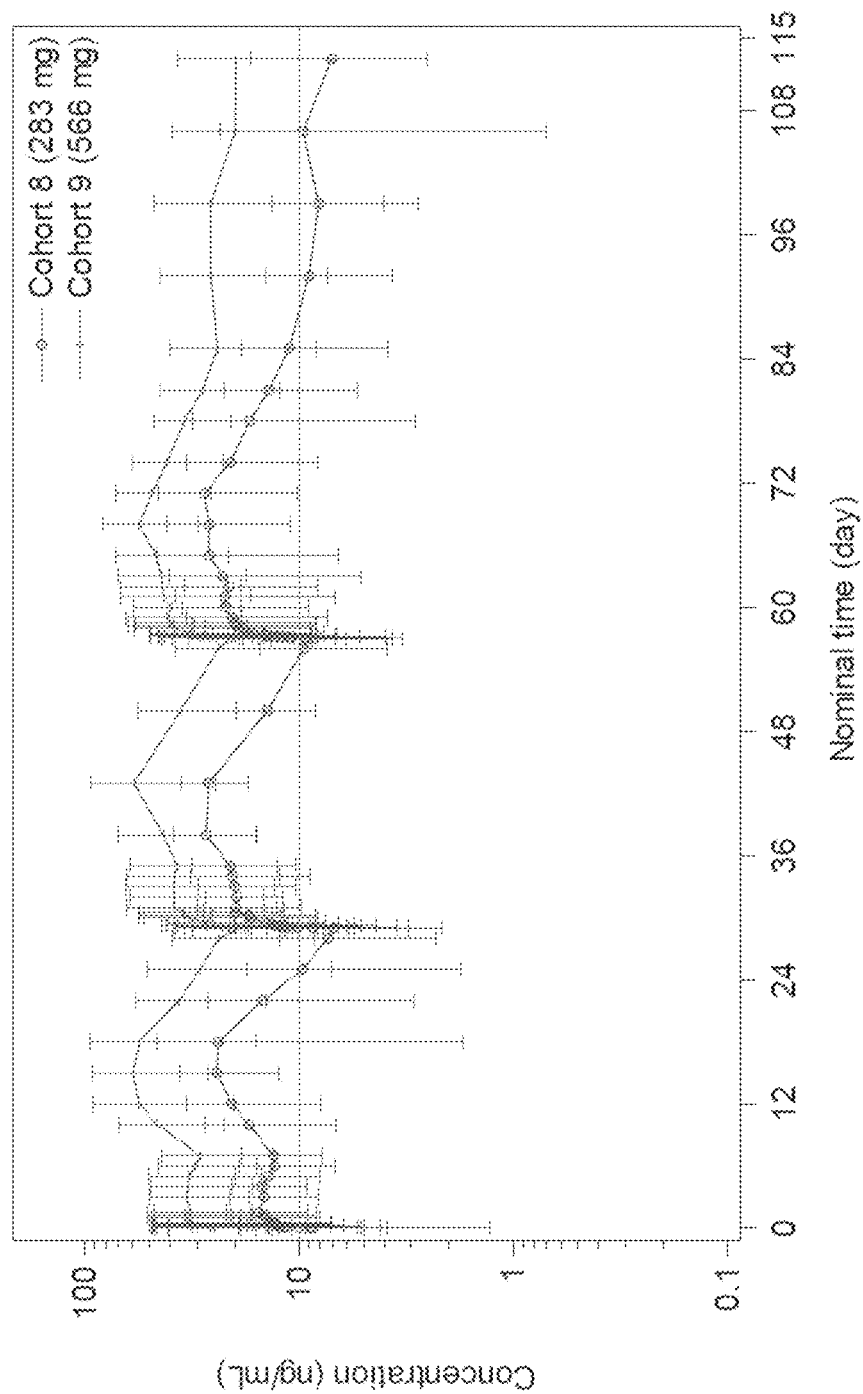
FIG. 7 shows the Mean (±Standard Deviation) Olanzapine Plasma Concentrations Versus Time on a Semi-Log Scale by Cohort and Dosing Day: Multiple-Dose Patient Cohorts Following Formulation 1 (Safety Analysis Set). The horizontal line represents the clinically relevant olanzapine plasma concentration of 10 ng/mL.

After 3 q1m sc administrations, median time to maximum plasma concentration was 11 and 10 days (262 and 236 hours) for Cohort 8 and Cohort 9, respectively. After reaching peak concentration, olanzapine levels declined slowly until the last sample collection. The increase in olanzapine exposure appeared to be proportional to the increase in dose in the multiple-dose cohorts. Following the last Formulation 1 dose (3rd dose), the data used to calculate the arithmetic mean $t_{1/2}$ values ranged from 22 to 25 days (539 to 589 hours) between Cohorts 8 and 9. Accumulation ratios for $AUC_{0-tau}$ and $C_{max}$ (injection 3/injection 1) indicated only modest accumulation of 1.30 and 1.14 for $AUC_{0-tau}$, and 1.09 and 0.90 for $C_{max}$, in Cohort 8 and Cohort 9, respectively. Both NCA and popPK analysis by inspection of Ctrough, AUCtau, and $C_{max}$ were relied upon to estimate attainment of steady state. Steady state was determined once stable values, both observed and simulated, were reached. As stated previously, Formulation 1 demonstrates minimal accumulation of olanzapine following a 2nd or 3rd dose in Cohort 8 and Cohort 9. It was concluded that steady state was attained rapidly within 2 injections, by the end of the 2nd administration at day 57 (week 8) (FIGS. 6 and 7).

Beta Elimination Phase Half-Life

The use of relevant beta elimination phase half-life in lieu of observed terminal elimination phase (observed-best-fit-lambda Z) may be beneficial for estimating time to steady-state attainment in cases of extended release with multi-compartment kinetics (Gidal et al, 2017; Krause et al, 2021). The relevance of using terminal half-life can be limited if drug concentrations decline slowly with low concentrations at the end of the tested pharmacokinetic profile which contributes only marginally to overall drug exposure.

The beta elimination phase half-life demonstrated better correlation to Formulation 1 steady-state as compared to the terminal elimination phase (observed-best-fit-lambda Z) half-life, due to the multi-phasic profile of Formulation 1. The mean beta half-life values for Formulation 1 ranged from 5 to 7 days for single-dose patient cohorts and 8 to 10 days for the multiple-dose patient cohorts (Table 5.2).

TABLE 5.2

Estimated Terminal (Lambda Z) Elimination Half-Life and Beta Half-Life

| Database | $t\frac{1}{2}$ (days) | Single-dose patient cohorts | | | Multiple-dose patient | |
|---|---|---|---|---|---|---|
| | | | | | Cohort 8 | Cohort 9 |
| | | Cohort 5 318 mg (n) | Cohort 4 425 mg (n) | Cohort 6 531 mg (n) | 283 mg - $3^{rd}$ dose (n) | 566 mg - $3^{rd}$ dose (n) |
| Final | Last sample (days) | 56 | 84 | 56 | 113 | 113 |
| | Lambda Z $t\frac{1}{2}$ (days) | 11.15 (12) | 16.83 (12) | 11.01 (12) | 24.56 (12) | 22.44 (7) |
| | Beta $t\frac{1}{2}$ (days) | 4.93 (4) | 7.16 (11) | 6.64 (12) | 8.49 (10) | 9.95 (5) |

Additional characterization of Formulation 1 at steady-state exposure was explored with the Pop PK modeling and simulations.

Dose Proportionality

Systemic exposure, as assessed by $C_{max}$ and AUC, increased in an approximately dose-proportional manner over the therapeutic dose range of 283 mg through 566 mg in patients, except for Cohort 6 (531 mg Formulation 1 sc dose) in whom $AUC_{0-28d}$ and $AUC_{0-\infty}$ were slightly lower than expected based on the exposures of the other dose levels; however, this change was not clinically significant and was most likely related to individuals with faster clearance of olanzapine following oral olanzapine and Formulation 1 administration and small sample size.

Figure 8:
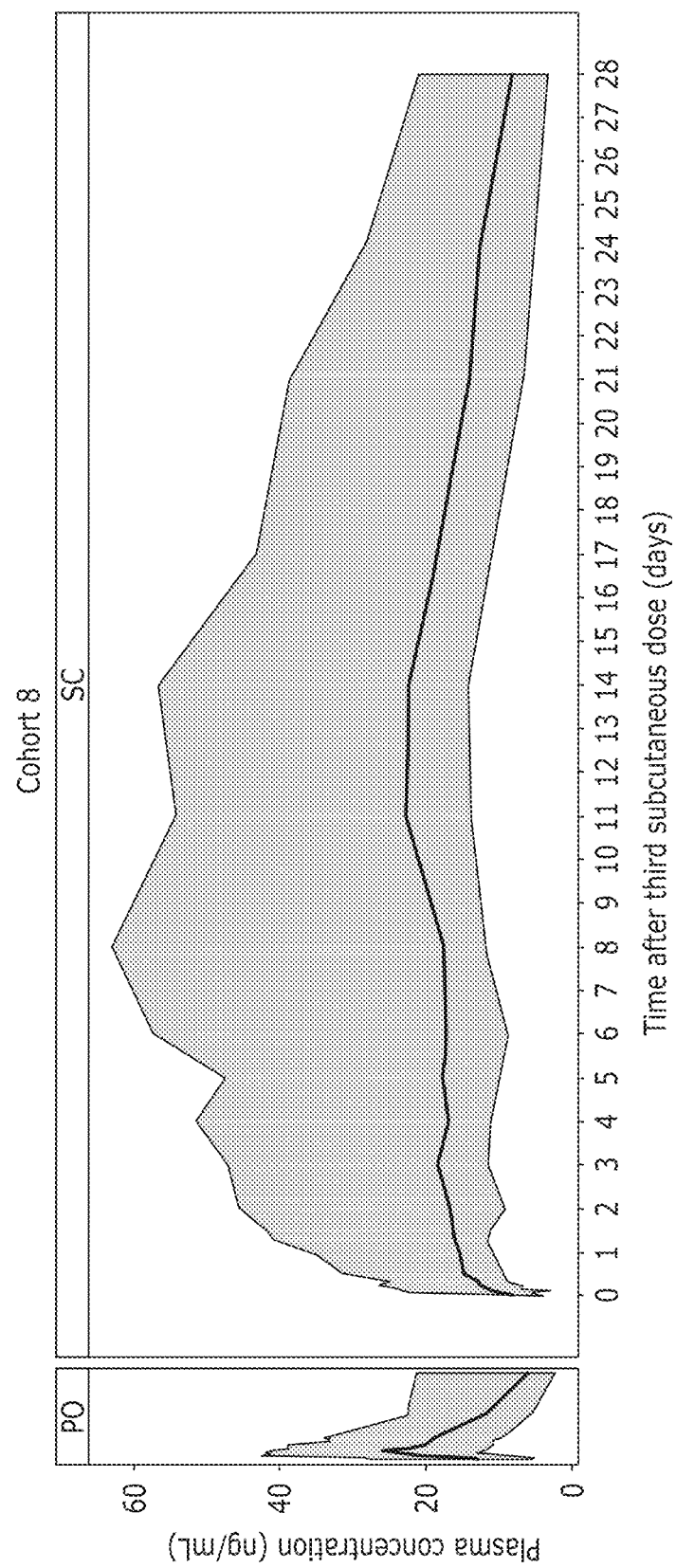
FIG. 8 shows the Observed Median Pharmacokinetic Profiles and Pharmacokinetic Variability (5th and 95th percentiles) of Olanzapine Concentration of Oral Olanzapine (Left Panels) and Formulation 1 (Right Panels) from the study described in Example 4. Top panel illustrates Cohort 8 (left panel: oral dose=10 mg; right panel: Formulation 1 dose=283 mg). Bottom panel illustrates Cohort 9 (left panel: oral dose=20 mg; right panel: Formulation 1 dose=566 mg).
Figure 8:
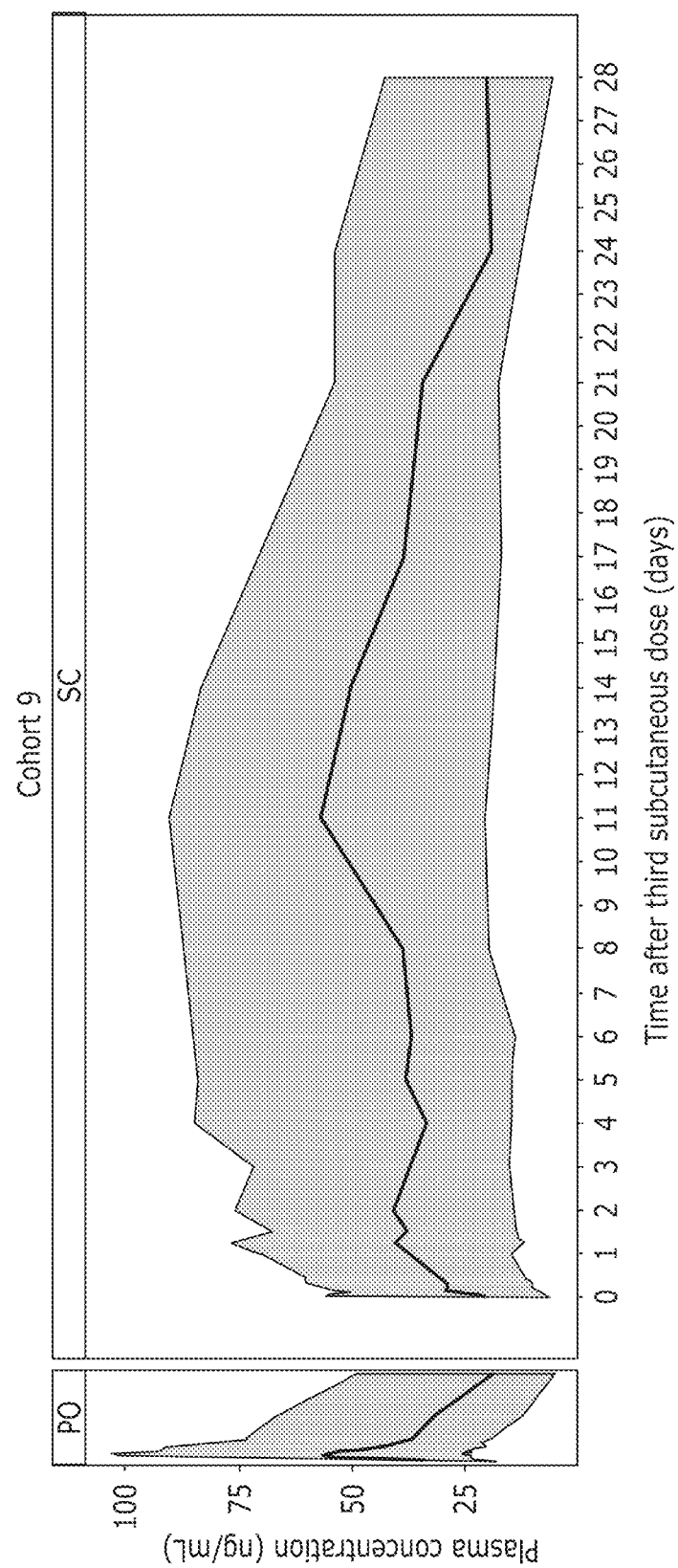

Although the study was not powered to assess dose proportionality, and despite the high variability observed for the PK parameters, there is a clear trend indicating dose proportionality. This finding is also supported by the popPK analysis. The observed olanzapine median PK profile and PK variability of oral olanzapine and Formulation 1 are shown in FIG. 8. Additionally, PK/PD simulations linked olanzapine concentration to D2 receptor occupancy, and determined the doses at which D2 receptor occupancy occurs. The simulations also confirmed the selected doses are targeted to result in a D2 receptor occupancy range of 60% to 80% D2RO, which is associated as the equilibrium point for antipsychotic efficacy and minimal side effects.

Formulation 1 Comparability to Oral Olanzapine

After the 3rd injection of Formulation 1 (day 57), when olanzapine plasma levels were considered to be at steady-state for doses of 283 and 566 mg, the systemic exposure range (Cmax,ss, trough plasma drug concentration at day 28 [C28d/Ctrough,ss], and average plasma concentration [Cavg,ss]) over a 28-day period were comparable to the systemic exposure observed after oral olanzapine administration over the dose range of 10 to 20 mg at steady-state.

The median concentrations including 5th and 95th percentiles for the observed olanzapine concentrations following the third of Formulation 1 (q1m; 283 mg) versus the seventh dose of oral olanzapine (10 mg/day), both of which are considered as steady-state, and Formulation 1 (q1m; 566 mg) versus oral olanzapine (20 mg/day) are shown in FIG. 8.

In general, the panels in FIG. 8 illustrate that pharmacokinetic variability of Formulation 1 over a 28-day dosing interval was comparable to that of oral olanzapine over a 24 hour dosing interval, with respect to 5th and 95th percentiles. Similarly, the overall exposure (ie, AUC) was comparable and had similar variability.

Relative Bioavailability

The relative bioavailability of Formulation 1 to oral olanzapine is presented in Table 5.3. Relative bioavailability at steady-state was calculated by the dose-normalized ratio of AUCinf after single dose of Formulation 1 (as a surrogate for AUCtau at steady-state) divided by AUCtau of oral olanzapine (calculated for 28 days). The relative bioavailability of the subcutaneous formulation of olanzapine is 112%, with 90% confidence intervals close to the bioequivalence acceptance criteria (0.969, 1.291) following Formulation 1 single-dose administration to patient cohorts (Cohorts 4 to 6). Following multiple-dose administration to patient cohorts (Cohorts 8 and 9), the relative bioavailability of Formulation 1 compared to oral olanzapine was 95% with 90% CIs of 0.855, 1.059. Although the sample size of the study was not powered to support bioavailability analysis, these results support the overall similarity of Formulation 1 to oral olanzapine, when given at comparable doses.

TABLE 5.3

Relative Bioavailability of Formulation 1 as Compared to Oral Olanzapine, Dose Normalized

| | Geometric LS Means | | | |
|---|---|---|---|---|
| | Single dose | | Comparison | |
| Parameter (unit) | Oral Olanzapine (Reference) | Formulation 1 (Test) | Geo LS Mean Ratio (Test/Ref) | 90% CI of Ratio (Test/Ref) |
| | Geo LS Mean | Geo LS Mean | | |

TABLE 5.3-continued

Relative Bioavailability of Formulation 1 as
Compared to Oral Olanzapine, Dose Normalized

| | Geometric LS Means | | Comparison | |
|---|---|---|---|---|
| | Single dose | | | |
| | Oral Olanzapine (Reference) | Formulation 1 (Test) | Geo LS Mean Ratio | 90% CI of Ratio |
| Single-dose patients cohorts (Cohorts 4, 5 and 6) | | | | |
| Dose-normalized AUC ([h*ng/mL]/mg)$^a$ | 38.12 | 42.65 | 1.12 | 0.969, 1.291 |
| Single-dose healthy subject and patient cohorts (Cohorts 1, 2, 3, 4, 5 and 6) | | | | |
| Dose-normalized AUC ([h*ng/mL]/mg)$^a$ | 42.09 | 47.57 | 1.13 | 1.043, 1.225 |
| Multiple-dose patient cohorts (Cohorts 8 and 9) | | | | |
| Dose-normalized AUC ([h*ng/mL]/mg)$^b$ | 49.25 | 46.88 | 0.95 | 0.855, 1.059 |

$^a$The relative bioavailability was evaluated for dose-normalized olanzapine AUC (ln-transformed $AUC_{0-\infty}$ for Formulation 1 and ln-transformed $AUC_{0-tau}$ for oral olanzapine, both treated as one outcome).
$^b$The relative bioavailability was evaluated for olanzapine dose-normalized AUC (ln-transformed $AUC_{0-tau}$ [Formulation 1] for the $3^{rd}$ Formulation 1 multiple dosing interval and dose-normalized ln-transformed $AUC_{0-tau28 d}$, calculated for oral olanzapine, both of which reflect the steady-state AUC over a 28-day dosing interval and is treated as one outcome). AUC = area under the plasma drug concentration-time curve; AUC0-∞ = area under the plasma drug concentration-time curve extrapolated to infinite time; AUC0-tau = area under the plasma drug concentration-time curve until end of dosing period; CI = confidence interval; Geo = geometric; GMR = geometric mean ratio; LS = least squares; Ref = reference.
Note:
Calculation of GMR: ratio of Formulation 1 dose normalized AUC0-∞ (based on pooled data from single dose cohorts) over oral olanzapine dose normalized AUC0-tau (multiplied by 28 days)

Safety Assessments

Safety was assessed during the study by evaluating AEs, clinical laboratory test results (serum, hematology, urinalysis, and prolactin), vital signs measurements, ECG, physical examination, injection site pain, local tolerability, and leakage assessment. In addition, psychiatric, neurological, and clinical symptoms assessments consisted of:

- Abnormal Involuntary Movement Scale (AIMS)
- Barnes Akathisia Rating Scale (BARS)
- Clinical Global Impression Scale-Severity of Illness (CGI-S)
- Columbia Suicide Severity Rating Scale (C-SSRS)
- Extrapyramidal Symptom Rating Scale (ESRS)
- Epworth Sleepiness Scale (ESS)
- Positive and Negative Syndrome Scale (PANSS)

The severity of an AE was graded according to the National Cancer Institute (NCI) Common Terminology Criteria for Adverse Events (CTCAE), Version 5.0 guideline for grades from Grade 1 (mild, asymptomatic or mild symptoms) to Grade 5 (death related to AE).

Formulation 1 Study Summary

The safety and the risk-benefit profile of Formulation 1 were evaluated using clinical safety data available to date from the study. All study cohorts were completed. The data cut-off included all safety and PK data from the single dose cohorts (cohorts 1 to 6). For the multiple dose cohorts (cohorts 8 and 9), partial PK and safety data following the third dose are available, as all patients had been dosed with Formulation 1 for three consecutive q1m injections and completed the treatment period (Day 85). For Cohort 8, 11 patients were in the FU period, and 1 patient completed the study. For Cohort 9, 6 patients were in the FU period, 6 completed the study, and 1 patient terminated early during the FU period.

The results from laboratory tests, vital signs, ECGs, clinical scales, and AEs do not suggest any new systemic safety signals for Formulation 1 and were consistent with the well characterized safety profile of olanzapine. No PDSS events or suspected PDSS events were observed during the study.

Injection site reactions observed in the study are related to the route of administration and do not appear to significantly alter the benefit-risk profile of Formulation 1.

Safety Conclusions

The safety endpoints in this study included incidence of adverse events, changes from baseline in ECG parameters, selected clinical laboratory values (including prolactin) and vital signs, as well as changes in neurological and clinical symptom assessments (eg, PANSS, ESRS, AIMS, BARS, CGI—S, C—SSRS), and other safety measures that were evaluated throughout the study.

Overall, single ascending doses and multiple-doses of olanzapine extended-release injectable suspension (Formulation 1) administered sc to healthy subjects and patients with a diagnosis of schizophrenia or schizoaffective disorder were well tolerated. The safety profile was similar to oral olanzapine, with the exception of the ISR's.

No deaths or treatment-related serious adverse events occurred in this study. During the washout period following oral olanzapine administration, 4/127 (3.1%) participants withdrew from the study due to adverse events (2 events of low density lipoprotein increased, and 1 event of neutropenia and rash); all these participants were healthy subjects. During Period 2 of the study, only 1 patient receiving a clinically relevant dose of Formulation 1 (Cohort 4; Formulation 1 425 mg) withdrew from the study due to a grade 3 serious adverse event of psychotic disorder, and 1 patient in Cohort 9 (multiple q1m Formulation 1 566 mg) experienced a grade 2 serious adverse event of schizophrenia during the study. Both these serious adverse events were considered by the investigators and sponsor to be not related to Formulation 1.

All treatment cohorts in Period 2 had at least 1 healthy subject or patient that experienced at least 1 treatment-related adverse event. The incidence of treatment-related adverse events was slightly higher in the single-dose healthy subject cohorts (30.0%) compared to the single-dose patient cohorts (23.8%), with the multiple-dose patient cohorts having the highest incidence of treatment-related adverse events (44.8%). The most frequently reported treatment-related adverse events (occurring in more than 4% of healthy subjects or patients overall) in the single-dose healthy subject cohorts were injection site erythema (6.7%) and headache (6.7%); in the single-dose patient cohorts were headache (4.8%), somnolence (4.8%), increased appetite (4.8%), or weight increased (4.8%); and in the multiple-dose patient cohorts were obesity (13.8%) and injection site pruritus (10.3%). Treatment-related adverse events were generally grade 1 or grade 2 in severity, with only 3 healthy subjects or patients experiencing grade 3 treatment-related events (1 healthy subject in Cohort 3 [Formulation 1, 105 mg, upper arm] experiencing ALT increased, 1 patient in Cohort 5 [Formulation 1, 318 mg] experiencing injection site abscess, and 1 patient in Cohort 9 [multiple q1m Formulation 1, 566 mg dose] experiencing an injection site erythema). No adverse events of grade 4 or grade 5 were reported during the study.

Protocol-defined adverse events of special interest included ISRs (only those defined as adverse events). ISR adverse events were observed in all treatment cohorts, except for Cohort 6 (Formulation 1, 531 mg). Of the injection site adverse events, the most frequently reported were events of injection site abscess (5 patients across all cohorts), injection site erythema (4 patients across all cohorts), and injection site pruritus (3 patients across all cohorts). Most of these injection site adverse events were grade 1 or grade 2 in severity, except for 1 event of grade 3 injection site abscess in Cohort 5 (Formulation 1, 318 mg) and 1 event of grade 3 injection site erythema in Cohort 9 (multiple q1m Formulation 1, 566 mg). Seven of these events were classified as pus-containing lesions: 5 cases of injection site abscesses with preceding inflammation reported in 1 of the cases, and 2 cases of injection site infection with no apparent dose-response. 1 event of injection site infection (1 patient in Cohort 4), was not considered as an ISR or related to Formulation 1 administration, as the cause of infection was irritation/scratching by the patient and was therefore classified as an injection site irritation. None of these events were identified as serious, and all events were recovered from and resolved following treatment with systemic antibiotics.

A dissimilar distribution and rate of pus-containing lesions per site of injection was observed; specifically, 3/11 (27.3%) healthy subjects with 3 injections out of 11 to the arm and 3/71 (4.2%) patients with 3 injections out of 129 to the abdomen. None of these events had an impact on Formulation 1 pharmacokinetics.

As expected with this class of drug, initial increases in mean prolactin levels were observed in both treatment periods (oral olanzapine and Formulation 1). However, no adverse events related to hyperprolactinaemia were observed during the study.

Overall, injections were generally well tolerated, with NPRS scores for injection pain intensity (0=no pain, 10=worst pain) immediately after dosing of 10 for 1 patient in Cohort 6 (Formulation 1, 531 mg), of 9 for 1 patient in Cohort 5 (Formulation 1, 318 mg single-dose) and 1 patient in Cohort 4 (Formulation 1, 425 mg), and of 8 for 2 patient in Cohorts 6 and 1 patient in Cohort 5; all other patients had NPRS scores ≤7. After day 8, minimal and sporadic injection site pain scores were recorded. Injection site reactions were generally grade 1 or grade 2 in severity and transient in nature.

Clinical laboratory test (including clinical chemistry, hematology, and urinalysis) vital signs and physical examination findings did not reveal any clinically meaningful trends in mean changes from baseline or clinically significant findings in any of these assessments, except for sporadic increases in creatine kinase that did not appear to be dose related in both treatment periods, and weight gain ≥7% from baseline in 38% of patients randomized to the multiple-dose patient cohorts. A slight worsening in ECG findings was observed across all treatment cohorts, although these were generally considered not to be clinically significant. Only 1 patient in the single-dose patient cohorts (Cohort 5; Formulation 1, 318 mg) experienced an adverse event of tachycardia.

No clinically meaningful changes in PANSS, ESRS, AIMS, BARS or ESS scores were observed during the study, and generally patient CGI-S and C-SSRS ratings remained stable throughout the study. No confirmed or suspected PDSS events (protocol-defined adverse event for expedited reporting) occurred during the study.

Formulation 1 Safety Summary

Safety data of Formulation 1 from 71 patients and 30 healthy subjects at doses of 70 to 566 mg, and 6 healthy subjects treated with Formulation 1 vehicle has been evaluated. The systematic safety profile emerging from these data is consistent with other formulations of olanzapine. The lack of clinically meaningful change from baseline in psychiatric, neurological, and clinical symptom assessment scales in this study, comprising clinically stable patients previously treated with oral olanzapine, supports the extended release of olanzapine following Formulation 1 injection, which results in a pharmacodynamic and systemic safety profile comparable to that of oral olanzapine. The identified ISR AEs were mostly mild to moderate in severity and have not been serious. These ISR AEs have not significantly altered the Formulation 1 benefit-risk profile.

Example 6

A Multinational, Multicenter, Randomized, Double-Blind, Parallel-Group, Placebo-Controlled Study with an Open-Label, Long-Term Safety Phase to Evaluate the Efficacy, Safety, and Tolerability of Olanzapine for Extended-Release Injectable Suspension (Formulation 1) for Subcutaneous Use as Treatment of Adult Patients with Schizophrenia

TABLE 6.1

Objectives and Endpoints:

| Objectives | Endpoints |
| --- | --- |
| The primary objective is to evaluate the efficacy of Formulation 1 in adult patients with schizophrenia. | The change from baseline to week 8 in the Positive and Negative Syndrome Scale (PANSS) total score |

TABLE 6.1-continued

Objectives and Endpoints:

| Objectives | Endpoints |
|---|---|
| A key secondary objective is to further evaluate the efficacy of Formulation 1 based on additional parameters in adult patients with schizophrenia. | Change in Clinical Global Impression-Severity (CGI-S) scale score from baseline to week 8; Change in Personal and Social Performance Scale (PSP) score from baseline to week 8 |
| A secondary objective is to evaluate the safety and tolerability of Formulation 1 in adult patients with schizophrenia. | The safety and tolerability endpoints will include, where appropriate, the following: adverse events (including serious adverse events, extrapyramidal symptoms, injection pain and other injection site reactions [local tolerability]), vital signs (blood pressure, pulse and orthostatic changes, and temperature), body weight, laboratory tests, electrocardiogram, concomitant medication use, time to all-cause discontinuation, all-cause discontinuation rates and discontinuation rates due to adverse events (tolerability), and the following rating scales: Abnormal Involuntary Movement Scale, Simpson-Angus Scale, Barnes Akathisia Rating Scale, Columbia Suicide Severity Rating Scale, and Calgary Depression Scale for Schizophrenia. |
| A secondary objective of this study is to evaluate the efficacy of Formulation 1 from baseline to endpoint in Period 1 in adult patients with schizophrenia. | Change in total PANSS score from baseline to weeks 1, 2, and 4; Change in Clinical Global Impression-Improvement scale score from baseline to weeks 4 and 8; Change in CGI-S scale score from baseline to weeks 1, 2, and 4; Change in Patient Global Impression-Improvement (PGI-I) scale score from baseline to week 8; Change in PGI-I scale score from baseline to weeks 2 and 4; Change in Schizophrenia Quality of Life Scale score from baseline to weeks 4 and 8; Change in PSP score from baseline to week 4 |

Overall Design

Patients with exacerbation of schizophrenia that started ≤8 weeks prior to screening and who would benefit from psychiatric hospitalization or continued hospitalization for symptoms of schizophrenia may be included. The study is composed of 2 periods: Period 1 (the double-blind, placebo-controlled, efficacy and safety period) and Period 2 (open-label safety period). For each patient, the duration of Period 1 is 8 weeks, and the duration of Period 2 is up to 48 weeks. Screening is up to 8 days prior to randomization. In Period 1, patients are randomized to one of 3 Formulation 1 treatment groups (318 mg once monthly [qIm], 425 mg qIm, or 531 mg qIm) or a placebo group qIm in a 1:1:1:1 ratio. In order to maintain the blind in Period 1, all patients are randomized again between Period 1 and Period 2; patients who were previously assigned to the active treatment groups will retain their Period 1 treatment assignment for Period 2, and patients who were previously assigned to the placebo group will be randomized to one of the active treatment groups in a 1:1:1 ratio for Period 2. The end-of-treatment and follow-up visits are at 4 and 8 weeks after the last dose of investigational medicinal product administration, respectively.

Study Intervention and Intervention Form

The purpose of this study is to assess the efficacy, safety, and tolerability of olanzapine extended-release injectable suspension for sc use (i.e., Formulation 1) compared with placebo in patients with schizophrenia. Total study duration is up to 61 weeks, and treatment duration is up to 56 weeks.

Number of Participants:

Approximately 985 patients are screened to achieve approximately 640 randomized patients.

This study enrolls patients diagnosed with schizophrenia according to the criteria of Diagnostic and Statistical Manual of Mental Disorders, 5$^{th}$ Edition (DSM-5). The diagnosis is confirmed using a structured assessment tool (Structured Clinical Interview for DSM-5, Clinical Trials Version [SCID-5-CT]).

The acute status is confirmed by the total PANSS score between 80 and 120, inclusive, at screening and baseline (prior to randomization), with a score ≥4 on at least 2 of the following 4 items of the PANSS positive subscale: hallucinatory behavior, delusions, conceptual disorganization, or suspiciousness/persecution, and a CGI-S score of ≥4 (moderately ill) at screening and baseline (prior to randomization).

Patient Inclusion Criteria

Patients may be randomized in this study only if they meet all of the following criteria:

a. The patient is a male or female of any ethnic origin, 18 to 65 years of age, inclusive, at the time of screening.

b. The patient is capable of providing signed informed consent. Patients will be asked to consent to share their information with a vendor that will verify that they are not currently participating or have not recently participated in another clinical study, unless prohibited by local requirements. In addition, patients will be asked to provide consent for audio recording of the PANSS assessments (which will be reviewed, as necessary, to monitor the quality of the ratings).

c. The patient has a current confirmed diagnosis of schizophrenia according to the DSM-5, for >1 year. Diagnosis must be reconfirmed by the SCID-5-CT.

d. The patient has a total PANSS score between 80 and 120, inclusive, at screening and baseline (prior to randomization) with a score ≥4 on at least 2 of the following 4 items of the PANSS positive subscale: hallucinatory behavior, delusions, conceptual disorganization, or suspiciousness/persecution.

e. The patient has exacerbation of schizophrenia that started ≤8 weeks prior to screening and would benefit from psychiatric hospitalization or continued hospitalization for symptoms of schizophrenia.

f. The patient has a CGI-S score of ≥4 (moderately ill) at screening and baseline (prior to randomization).

g. Patients who have received an antipsychotic treatment (other than clozapine) in the past year must have been responsive based on the investigator's judgment (and based on discussions with family members, caregivers, or healthcare professionals, as applicable).

h. The patient has an identified responsible person (referred to as the caregiver) who has agreed to provide information about the patient's location, condition, and overall status during outpatient portions of the study during Period 1. The site personnel must identify the caregiver at the screening visit and consider the caregiver a reliable contact person. The caregiver must have regular contact with the patient (defined as direct contact not fewer than 3 times per week), with the expectation that this frequency of contact would continue throughout the outpatient portion of Period 1 (it is also advised during the rest of the study, including Period 2 and the FU period). This regular contact with the patient is not mandatory during the hospitalization period of Period 1. The patient's caregiver will be asked to sign a caregiver ICF.

i. Body mass index between 18.0 and 40.0 kg/m², inclusive, at the time of screening.

j. Women may be included only if they have a negative beta-human chorionic gonadotropin (β-HCG) test at screening and baseline (if a borderline result is obtained on a urine test, a serum test should be performed and a negative result obtained) or are sterile (documented hysterectomy, bilateral oophorectomy, or bilateral salpingectomy or congenitally sterile) or postmenopausal.

k. Women of childbearing potential must agree not to try to become pregnant, and, unless they have exclusively same-sex partners, must agree to use a highly effective method of contraception prior to the first administration of IMP, and agree to continue the use of this method for the duration of the study, and for 70 days after the last dose of IMP. Highly effective methods of contraception include the following:

l. Combined estrogen and progestogen hormonal contraception (oral, intravaginal, transdermal) associated with inhibition of ovulation; these should be initiated at the screening visit before the first dose of IMP.

m. Progestogen-only hormonal contraception (oral, injectable, implantable) associated with inhibition of ovulation; these should be initiated at the screening visit before the first dose of IMP.

n. Intrauterine device and intrauterine hormone-releasing system; these need to be in place at least 2 months before screening.

o. Bilateral tubal occlusion.

p. Vasectomized partner, provided that he is the sole sexual partner and has received medical assessment of the surgical process.

q. Sexual abstinence is only considered a highly effective method if defined as refraining from heterosexual intercourse in the defined period. The reliability of sexual abstinence needs to be evaluated in relation to the duration of the clinical study and the preferred and usual lifestyle of the patient.

r. The patient, if an adult male, is surgically sterile, or, if capable of producing offspring, has exclusively same-sex partners or is currently using an approved method of birth control and agrees to the continued use of this method for the duration of the study (and for 70 days after the last dose of IMP). Male patients with sex partners who are women of childbearing potential must use condoms even if surgically sterile. In addition, male patients may not donate sperm for the duration of the study and for 70 days after the last dose of IMP.

s. The patient is able to understand the nature of the study and follow protocol requirements, including the prescribed dosage regimens (oral and sc administration), non-use of prohibited concomitant medications, and hospitalization for at least 4 weeks at the clinical site; can read and understand the written word in order to complete patient-reported outcomes measures by themselves; and can be reliably rated on assessment scales.

t. The patient must be willing and able to comply with study restrictions and to remain at the investigational center for the required duration during the study period (including hospitalization for at least 4 weeks at the clinical site) and must be willing to return to the investigational center for further visits, as applicable, and for the FU procedures and assessments as specified in this protocol.

u. The patient has a stable place of residence for approximately 3 months before screening, and changes in residence are not anticipated over the course of study participation.

v. The patient is in adequate health as determined by medical and psychiatric history, medical examination, electrocardiogram (ECG), serum chemistry, hematology, coagulation urinalysis, and serology.

Patient Exclusion Criteria

Patients are not randomized in this study if they meet any of the following criteria:

a. The patient has a current clinically significant DSM-5 diagnosis other than schizophrenia (has a primary current diagnosis other than schizophrenia or a comorbid diagnosis that is primarily responsible for the current symptoms and functional impairment).

b. The patient has a known history of the following: (a) borderline personality disorder, antisocial personality disorder, or bipolar disorder; (b) traumatic brain injury causing ongoing cognitive difficulties, Alzheimer's disease, or another form of dementia, or any chronic organic disease of the central nervous system; and (c) intellectual disability of a severity that would impact ability to participate in the study.

c. The patient has an improvement (reduction) in the total PANSS score of ≥20% between screening and day 1 (baseline [randomization] visit).

d. The patient was hospitalized for >14 days (with the exception of social or administrative hospitalization) in the current exacerbation episode prior to screening.

e. The patient has a significant risk of violent behavior based on the patient's medical history or investigator's judgment.

f. The patient has a significant risk of committing suicide based on the patient's medical history or C-SSRS, and the investigator's judgment.

Patients with a C-SSRS positive response to suicidal ideation items 3, 4, or 5 and/or positive suicidal behavior response in the past 6 months are not eligible.

g. The patient meets criteria for moderate to severe substance use disorder (based on DSM-5 criteria) within the past 6 months, such as chronic alcohol abuse or drug abuse (excluding those related to caffeine or nicotine). If, per the investigator's judgment, a patient does not meet the criteria for substance use disorder, a positive result on the urine drug test is not exclusionary. Patients' eligibility in such case of positive result, without medical explanation, will be determined by the investigator based on the patient's background, history of substance use, and the investigator's discussions with family members, caregivers, or healthcare professionals, as applicable.
h. The patient is currently using an LAI antipsychotic or is still under the coverage period of the specific LAI at time of screening.
i. The patient has taken clozapine or has received electroconvulsive therapy within the last 12 months prior to screening.
j. The patient is currently receiving daily oral olanzapine at a dose >20 mg/day.
k. The patient has current or a history of known hypersensitivity to olanzapine or any of the excipients of Formulation 1 or the oral formulation of olanzapine.
l. The patient has treatment-resistant schizophrenia according to medical and psychiatric history, as judged by the investigator or documented failure of 2 or more antipsychotic medications (administered at the maximum tolerated dose for at least 6 weeks each). Participants who have responded to antipsychotics only when paired with clozapine are considered treatment resistant.
m. The patient has had a significant sedation or delirium after antipsychotic treatment according to medical and psychiatric history and as judged by the investigator or suffered from delirium due to a medical condition.
n. The patient has any medical or psychiatric condition that, in the opinion of the investigator, could jeopardize or would compromise the patient's ability to participate in this study.
o. The patient has known risk factors for undiagnosed/instable arrhythmia, congenital long QT, hypokalemia, hypomagnesemia, or autonomic failure (mostly with clinically significant orthostatic hypotension).
p. The patient has any clinically significant uncontrolled medical condition (treated or untreated).
q. Any disorder that may interfere with absorption, metabolism, or elimination of olanzapine
r. The patient has a non-fasting glucose level of ≥200 mg/dL at screening.
s. The patient had a change in their diabetes treatment within 4 weeks before the first injection of the IMP.
t. The patient has serum triglycerides levels of ≥500 mg/dL.
u. The patient has low-density lipoprotein levels of ≥190 mg/dL.
v. The patient has a history of ketoacidosis or hyperosmolar coma.
w. The patient has known alanine aminotransferase (ALT)/serum glutamic pyruvic transaminase values ≥2× the upper limit of normal (ULN) of the performing laboratory, and aspartate aminotransferase (AST)/serum glutamic oxaloacetic transaminase values ≥2×ULN, and total bilirubin values ≥1.5×ULN.
Isolated parameters for exclusion are as follows:
ALT or AST >5×ULN
ALT or AST >3×ULN, and in addition either total bilirubin level >2×ULN or international normalized ratio >1.5 (if elevation of international normalized ratio is not caused by anticoagulants)
ALT or AST >3×ULN with the appearance of fatigue, nausea, vomiting, right upper quadrant pain or tenderness, fever, rash, and/or eosinophilia (>5%)
x. The patient has a neutrophil count of <1200/mm$^3$.
y. The patient has platelet count ≤75×10$^3$ μL.
z. The patient has serum creatinine >2.5 mg/dL.
aa. The patient has a positive serology for human immunodeficiency virus (HIV)-1, HIV-2, hepatitis B surface antigen, and/or hepatitis C. If serology is positive for hepatitis C but the ribonucleic acid (RNA) test is negative, and the patient has no history of liver disease or symptoms of active liver disease, enrollment will be allowed based on clinical judgment.
bb. The patient is a pregnant or lactating woman or plans to become pregnant during the study.
cc. The patient has previously participated in this study (except for rescreening).
dd. The patient is or has been using or consuming the medications prohibited in this protocol.
ee. The patient used an investigational drug (new chemical entity) or a medical device in a clinical study within 30 days or 5 half-lives (whichever is longer), or, in case of a biologic investigational drug, within 3 months or 5 half-lives (whichever is longer) prior to the first Formulation 1 administration.
ff. The patient has donated or received any blood, plasma, or platelet transfusions within 30 days prior to the study or have planned donations during the study period or 6 months following the last dose of IMP administration.
gg. The patient has a pending court appearance that may result in incarceration.

Eligibility Criteria for Period 2

In order to enter Period 2, the patient should meet the following eligibility criteria:
1. Patient has completed Period 1.
2. Patient is considered sufficiently clinically stable per the investigator's judgment.
3. Patient is an outpatient (ie, met RDQ criteria and was discharged prior to Period 2).

Patients who do not meet RDQ criteria, but in the opinion of the investigator show sufficient clinical stabilization for transition to Period 2 and may benefit from continuation of participation in the study, may continue to Period 2 as inpatients for up to an additional 8 weeks. For such patients, RDQ can be assessed periodically according to investigator discretion; if RDQ criteria are not met by the end of the additional 8-week hospitalization period (week 16), then the patient will be discontinued from study treatment and will be asked to complete ET and FU visits.

Intervention Groups and Duration

The screening period includes treatment with 2 consecutive daily doses of oral olanzapine to establish tolerability (for patients who were not previously treated with oral olanzapine in the past year) prior to randomization into Period 1. During Period 1 (8 weeks), patients receive 2 monthly sc injections of Formulation 1 (318 mg, 425 mg, or 531 mg) or placebo. During Period 2 (up to 48 weeks), all patients receive up to 12 monthly injections of Formulation 1.

Investigational Medicinal Products Used in the Study

IMP is defined as the test IMP and matching placebo IMP to the test IMP.

Refer to Table 6.3 for a description of the test IMP (Formulation 1) and placebo IMP.

Test Investigational Medicinal Product

Formulation 1, referred to in the Examples, is a pharmaceutical composition of the disclosure comprising: 30%-32% (w/w) of olanzapine; 52%-54% (w/w) of dimethyl sulfoxide; 12%-14% (w/w) of a diblock copolymer comprising polylactic acid and polyethylene glycol and having a number average molecular weight of 6.5 to 12.5 kg/mol and comprising 75%-84% by weight (w/w) polylactic acid; and 3%-3.5% (w/w) of a triblock copolymer comprising polylactic acid and polyethylene glycol and having a number average molecular weight of 6 to 13 kg/mol and comprising 83%-88% by weight (w/w) polylactic acid; and wherein the diblock copolymer and triblock copolymer together comprise 15%-17.5% by weight (w/w) of the composition.

The drug product is intended for reconstitution. Vehicle containing the excipients is used for reconstitution.

Formulation 1 requires reconstitution from 2 components as follows: 1 vial containing the olanzapine drug substance powder and 1 PFS containing vehicle (2 block copolymer excipients dissolved in an organic solvent comprising dimethyl sulfoxide). Before administration, Formulation 1 is reconstituted in the vial by adding the vehicle from the PFS and mixing.

Formulation 1 is administered in the abdomen, by sc injection at a q1m interval, at a dose equivalent to oral olanzapine 10, 15, or 20 mg/day per the conversion in Table 6.2. Upon reconstitution, Formulation 1 contains 305 mg of olanzapine per gram of total formulation. The dose is selected by withdrawing a specific, prescribed volume into the dosing syringe.

The injection is administered in an alternating manner to the right and to the left of the umbilicus. The subsequent monthly injections are rotated in a clockwise order between the abdomen quadrants.

Dosing Groups

Formulation 1 is administered at 3 doses in this study: low (318 mg q1m), medium (425 mg q1m), and high (531 mg q1m).

TABLE 6.2

Conversion Between Oral Olanzapine and Formulation 1 Doses

| Oral dose of olanzapine | Formulation 1 olanzapine dose | Formulation 1 volume to be dosed |
| --- | --- | --- |
| 10 mg | 318 mg | 0.9 mL |
| 15 mg | 425 mg | 1.2 mL |
| 20 mg | 531 mg | 1.5 mL |

Placebo Investigational Medicinal Product

Formulation 1 placebo is composed of 2 components as follows: 1 empty vial and 1 PFS containing vehicle (2 block copolymer excipients dissolved in DMc). Before administration, the placebo product is prepared in the vial by adding the vehicle from the PFS and mixing. The volume of the Formulation 1 placebo to be dosed is 0.8 mL.

Other Components

The kit for IMP and placebo IMP contains the following:

Two 16-gauge needle: one for adding vehicle to the vial for reconstitution and one for withdrawing the drug product once reconstituted into the dosing syringe One 3-mL luer lock disposable syringe with luer lock tip One 21-gauge, 16-mm (i.e., ⅝ inch) hypodermic safety needle with needle protection device for sc administration

TABLE 6.3

Investigational Medicinal Products Used in the Study

| IMP name | Test IMP | Placebo IMP |
| --- | --- | --- |
| Formulation | Formulation 1 powder and vehicle for extended-release injectable suspension | Formulation 1 placebo vehicle for extended-release injectable suspension |
| Unit dose strength(s)/ Dosage level(s) | Olanzapine powder and vehicle Dose levels: low (318 mg q1m), medium (425 mg q1m), and high (531 mg q1m) | Vehicle and empty vial for placebo |
| Route of administration | sc injection (abdomen) | sc injection (abdomen) |
| Dosing instructions | q1m injections per the patient's assigned treatment group | q1m injections per the patient's assigned treatment group |
| Packaging | IMP will be provided in a blister tray in a carton box. | IMP will be provided in a blister tray in a carton box. |

IMP = investigational medicinal product; INN = international nonproprietary name; q1m = once monthly; sc = subcutaneous.

Allowed Concomitant Medications
Rescue Medications

Allowed rescue medications will include zolpidem, zopiclone, zaleplon, or diphenhydramine for insomnia; benztropine, trihexyphenidyl, or diphenhydramine for parkinsonian symptoms; and propranolol and benzodiazepines for akathisia.

In addition, during the screening period and in Period 1, use of lorazepam (up to 6 mg/day or up to the maximal daily dose allowed locally [the lower of the two]) is permitted on an as-needed basis for indications other than akathisia (anxiety). Use in this context must be limited to no more than 72 consecutive hours, and lorazepam should not be taken within 8 hours prior to rating scale assessments.

In Period 2, use of lorazepam (per local label approved dose) is permitted on an as-needed basis for indications other than akathisia (anxiety). Antihistamine and anticholinergic drugs will be permitted during the study for agitation and insomnia.

Antidepressants and Mood Stabilizers

Screening Period and Period 1: Patients who are currently treated with antidepressants and/or mood stabilizers for at least 3 months prior to screening and with no change in dose for at least 4 weeks prior to screening (except for indications excluding the patient from entering the study, such as schizoaffective disorder) may continue their treatment during the screening period/Period 1. No change of dose or new treatment initiation with such medications will be permitted in the screening period/Period 1.

Period 2: During Period 2, patients who received mood stabilizers and antidepressants prior to study entrance for at least 3 months prior to screening and with no change in dose for at least 4 weeks prior to screening and continued their treatment during Period 1 will be allowed to continue their treatment. New administrations of mood stabilizers will be not permitted; dose adjustments of mood stabilizers may be allowed on a case-by-case basis after discussion with the MM.

Dose adjustment of antidepressants will be allowed in Period 2 according to the investigator's clinical judgment. Patients who did not receive antidepressants previously will be allowed to initiate treatment with some antidepressants (including selective serotonin reuptake inhibitors [other than fluvoxamine], serotonin and norepinephrine reuptake inhibitors, and trazodone) during Period 2 based on the investigator's clinical judgment.

Investigators are encouraged to approach the MM or the sponsor prior to initiating any new antidepressant treatment. The use of other antidepressants (such as tricyclic and tetracyclic antidepressants and bupropion) will be prohibited.

Screening (Up to 8 Days Prior to Randomization to Period 1):

Patients undergo screening procedures and assessments up to 8 days prior to randomization to Period 1. Patients provide informed consent at the screening visit before any study-related procedures are performed. Patients are asked to consent to share their information with a vendor that will verify that they are not currently participating or have not recently participated in another clinical study, unless prohibited by local requirements. In addition, patients are asked to provide consent for audio recording of the PANSS assessments (which are reviewed, as necessary, to monitor the quality of the ratings). Patients willing to participate in the optional pharmacogenetic and biomarker sampling and the optional exploratory assessment of audio recordings sign a separate informed consent form (ICF) for this purpose.

Patients with exacerbation that started ≤8 weeks prior to screening (the investigator should confirm the exacerbation based on the patient's medical records and/or based on anamnesis) and who would benefit from psychiatric hospitalization or continued hospitalization for symptoms of schizophrenia may be included in this study.

The patient's total Positive and Negative Syndrome Scale (PANSS) score should be between 80 and 120, inclusive, at screening with a score ≥4 on at least 2 of the following 4 items of the PANSS positive subscale: hallucinatory behavior, delusions, conceptual disorganization, or suspiciousness/persecution.

Patients must have an identified responsible person (referred to as the caregiver) who has agreed to provide information about the patient's location, condition, and overall status during outpatient portions of the study during Period 1. The site personnel must identify the caregiver at the screening visit and consider the caregiver a reliable contact person. The caregiver must have regular contact with the patient (defined as direct contact not fewer than 3 times per week), with the expectation that this frequency of contact would continue throughout the outpatient portion of Period 1 (it is also advised during the rest of the study, including Period 2 and the FU period). The patient's caregiver is asked to sign a caregiver ICF at screening.

Patients who are not already in an inpatient setting are hospitalized during the screening period (see details pertaining to hospitalization duration and discharge criteria in the description of "Period 1" below).

Patients taper off their prior oral antipsychotic medications at rates per the investigator's discretion. The tapering-off process should be completed prior to randomization.

Patients entering the study who have not previously received oral olanzapine receive 2 oral doses of olanzapine for 2 consecutive days during the screening period (the second dose should be administered at least 24 hours prior to randomization) to assess patient tolerability (oral olanzapine 10 mg/day or higher [but not exceeding 20 mg/day] per investigator decision). The PANSS and Clinical Global Impression-Severity (CGI-S) is completed prior to oral olanzapine administration.

Patients who received olanzapine within the last year are not required to receive the 2 doses of oral treatment. The investigator verifies the previous use, tolerability, and duration of olanzapine treatment to assure prior tolerability.

In the event that a patient meets all study inclusion criteria and does not meet any of the study exclusion criteria, but results of screening blood samples taken within the 8-day screening period are not available by day 8 of screening, the screening period may be extended by 2 days (until day 10 of screening) to allow the receipt of the results to confirm patients' eligibility. In case results are not available by day 10, the patient is considered a screening failure and may be considered for rescreening.

Period 1 (8 weeks):

Period 1 is an 8-week double-blind, placebo-controlled, efficacy and safety period (acute treatment phase).

Randomized patients have a PANSS total score between 80 and 120, inclusive, at baseline (prior to randomization) with a score ≥4 on at least 2 of the following 4 items of the PANSS positive subscale: hallucinatory behavior, delusions, conceptual disorganization, or suspiciousness/persecution.

Patients demonstrating a reduction in the total PANSS score of ≥20% between screening and the baseline (randomization) visit are not eligible for randomization into the study.

Randomized patients are treated with sc injections of Formulation 1 (low [318 mg q1m], medium [425 mg q1m], or high dose [531 mg q1m]) or placebo at visit 2 (week 0) and visit 7 (week 4).

At visits 2 and 7, the PANSS, Columbia Suicide Severity Rating Scale (C-SSRS), CGI-S, and Clinical Global Impression-Improvement (CGI-I; visit 7 [week 4] only) scales are completed prior to investigational medicinal product (IMP) administration; all other scales and questionnaires are completed either prior to IMP administration or after. Any assessments performed after IMP administration is completed on the day of IMP administration.

Prior to screening, patients are either outpatients or inpatients. All patients are hospitalized upon study entry (screening) and remain hospitalized during the screening period and for the first 4 weeks after randomization (until the second IMP administration). After the second injection, patients may be discharged if all discharge criteria are met and if, in the opinion of the investigator, discharge is appropriate.

For the entire duration of Period 1 (including the inpatient and outpatient setting), a window of ±3 days is allowed around the scheduled visit dates for dosing visits; a window of ±2 days is allowed for all other visits (during the inpatient period, every effort will be made to maintain the assessments on the scheduled dates). Visit dates are calculated from the date of previous IMP administration. In exceptional cases, per the discretion of the investigator and with permission from the medical monitor (MM) or sponsor, dosing visits take place up to 5 days before the scheduled visit date (and recorded accordingly).

Period 2 (Up to 48 Weeks):

Following completion of Period 1 (8 weeks), eligible patients continue to Period 2, the safety period (long-term safety phase; up to 48 weeks). During this period, patients receive monthly sc injections of Formulation 1.

Visit 11 (week 8) is the last visit of Period 1 and the first visit in Period 2. In order to maintain the blind in Period 1, all patients are randomized again between Period 1 and Period 2; patients who were previously assigned to the active treatment groups retain their Period 1 treatment assignment (the re-randomization of patients in the Formulation 1 groups is done only to maintain blinding of Period 1, and de facto is a deterministic assignment and not randomization), and patients who were previously assigned to the placebo group are randomized to one of the active treatment groups in a 1:1:1 ratio. The treatment with Formulation 1 at this visit is assigned to Period 2 and is performed according to the re-randomization treatment assignment. Scales and questionnaires and other assessments are completed only once. Revealing of the treatment assignment in Period 2 is performed only after completion and reporting of the relevant study procedures related to assessment of efficacy and safety endpoints in Period 1, on a patient-by-patient basis. The revealing of the Period 2 treatment assignment is performed between week 8 and week 12 by the sponsor or delegates according to a process predefined in the relevant study plans, provided that all requirements stipulated in this process are met. Therefore, the dosing at week 8, although assigned to Period 2, is handled in a blinded manner by all parties, similarly to the dosing in Period 1.

The study continues on an outpatient basis (or inpatient basis for patients who remain hospitalized for up to an additional 8 weeks), and telephone contacts (or other comparable form of remote communication) take place weekly between the monthly in-clinic visits. If, in the judgment of the investigator, the patient is likely to experience an exacerbation or pose a danger to himself/herself or others, that patient is invited for an unscheduled visit and/or hospitalized if needed, and the patient is treated per the investigator's judgment. If treatment with disallowed medications is required, including antipsychotics other than Formulation 1, the patient is discontinued from study treatment and is asked to complete ET and FU visits.

The PANSS, C-SSRS, CGI-S, and CGI-I scales are completed prior to IMP administration; all other scales and questionnaires may be completed either prior to IMP administration or after (except for visit 11 [week 8], where all assessments must be completed prior to IMP administration). Any assessments performed after IMP administration are completed on the day of IMP administration.

For the entire duration of Period 2 (including any phone visits), a window of ±3 days is allowed around the scheduled visit dates for dosing visits; for any patients who are inpatients at the beginning of Period 2, every effort is made to maintain the assessments on the scheduled dates during the inpatient period. Visit dates are calculated from the date of previous IMP administration. In exceptional cases, per the discretion of the investigator and with permission from the MM or sponsor, dosing visits may take place up to 5 days before the scheduled visit date (and recorded accordingly).

Patients entering Period 2 are treated for up to 48 weeks. An end-of-treatment (EOT) visit is completed 4 weeks after the patient's last injection.

Dose Adjustments:

During Period 2, the investigator may perform dose adjustments of Formulation 1 (to one of the doses offered in the protocol) from visit 12 (week 12) and onward, based on clinical judgment. Dose adjustment are documented in the CRF.

Procedures for Potential Post-Injection Delirium/Sedation Syndrome

During Period 1 and Period 2, following IMP administration, patients remain in the clinic for at least 3 hours for observation. If a potential PDSS event occurs, vital signs and blood samples for plasma drug concentration and biomarkers (for patients who provided consent for biomarker collection) should be collected as soon as a potential PDSS event is suspected. In case a suspected PDSS event is reported, a toxicological blood test should be collected from the patient as soon as PDSS is suspected. Additional pharmacokinetic samples will be collected at 3, 6, 12, and 24 hours after the onset of the event and 24 hours after resolution, or when feasible. Additional biomarker samples should be collected 24 hours after the onset of the event and 24 hours after resolution, or when feasible. Vital signs should be measured at the same time points that additional pharmacokinetic samples are collected.

The total duration of patient participation in the study includes up to 8 days of screening, during which oral olanzapine will be administered for 2 consecutive days (to establish tolerability), 8 weeks of treatment with Formulation 1 or placebo (Period 1 [acute treatment phase]), up to 48 weeks of treatment with Formulation 1 (Period 2 [long-term safety phase]), and 4 weeks of FU.

The end of study is defined as the last visit of the last patient.

Figure 9:
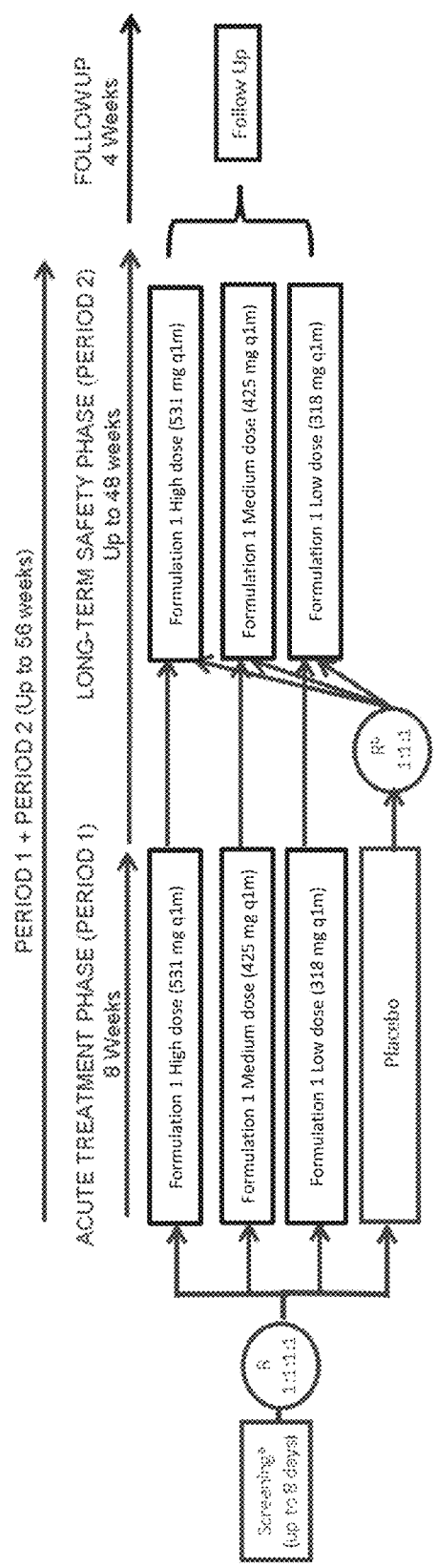
FIG. 9 shows a schematic outline of the study described in Example 6.

The study schematic diagram is presented in FIG. 9.

Assessment of Efficacy

The primary efficacy endpoint of the study is the change from baseline to week 8 in the PANSS total score.

A key secondary efficacy endpoint is change in Clinical Global Impression-Severity of Illness Scale (CGI-S) score from baseline to week 8.

A key secondary efficacy endpoint is change in Personal and Social Performance Scale (PSP) from baseline to week 8.

Additional secondary efficacy and safety endpoints to be measured include:
  Change in the total PANSS score from baseline to weeks 1, 2 and 4;
  Change from baseline in Clinical Global Impression-Improvement (CGI-I) scale score
  Change from baseline in Patient Global Impression-Improvement (PGI-I) scale score
  Change from baseline in Schizophrenia Quality of Life Scale (SQLS) score
  Number of participants reporting use of at least one concomitant medicament
  Number of participants that discontinues the trial
  Number of participants that discontinues the trial due to adverse events
  Change from baseline in abnormal Involuntary Movement Scale (AIMS) total score
  Change from baseline in Simpson-Angus Scale (SAS) mean score
  Change from baseline in Barnes Akathisia Rating Scale (BARS) total score
  Number of participants with any suicidal ideation or behavior according to the Columbia Suicide Severity Rating Scale (C-SSRS)
  Change from baseline in Calgary Depression Scale for Schizophrenia (CDSS)
  Other Assessment may include Structured Clinical Interview for DSM-5, Clinical Trials Version (SCID-5-CT) or 3-Level EuroQol Five Dimensions Questionnaire.

For a description of the Positive and Negative Syndrome Scale (PANSS) see paragraph [00418] supra.

The audio of PANSS assessments may be recorded (which will be reviewed, as necessary, to monitor the quality of the ratings).

The PANSS is administered by the investigator/trained rater at screening and all the time points specified in Table 6.4 and Table 6.5.

Quality of Life Scales

The quality of life scales used in this study include the 2 measures described below.

TABLE 6.4

Period 1

Week$^g$

| | Wk -2 to -1 | Wk 0 BL | Wk 0 | Wk 1 | Wk 2 | Wk 3 | Wk 4 | Wk 5 | Wk 6 | Wk 7 | Wk 8 | 4 weeks after last dose | 8 weeks after last dose |
|---|---|---|---|---|---|---|---|---|---|---|---|---|---|
| PANSS | X | X | | X | X | X | X | X | X | X | X | X | X |
| CGI-S | X | X | | X | X | X | X | X | X | X | X | X | X |
| CGI-I$^q$ | | | | | | | X | | | | X | X | X |
| PSP | X | X | | | | | X | | | | X | X | X |
| SQLS | X | X | | | | | X | | | | X | X | X |
| EQ-5D-3L | X | X | | | | | X | | | | X | X | X |
| PGI-I | | | | X | | X | | | | | X | X | |

TABLE 6.5

Period 2

Week$^g$

| | Wk 8 (Day 57) | Wk 9-11 | Wk 12 | Wk 13-15 | Wk 16 | Wk 17-19 | Wk 20 | Wk 21-23 | Wk 24 | Wk 25-27 | Wk 28 | Wk 29-31 | Wk 32 | Wk 33-35 | 4 wks after last dose | 8 wks after last dose |
|---|---|---|---|---|---|---|---|---|---|---|---|---|---|---|---|---|
| PANSS | X | | X | | X | | X | | X | | X | | X | | X | X |
| CGI-S | X | X | X | | X | | X | | X | | X | | | | X | X |
| CGI-I$^r$ | X | | | | X | | | | X | | | | X | | X | X |
| PSP | X | | | | X | | | | X | | | | X | | X | X |
| SQLS | X | | | | X | | | | X | | | | X | | X | X |
| EQ-5D-3L | X | | | | X | | | | X | | | | X | | X | X |
| PGI-I | X | | | | | | | | | | | | | | X | |

For a description of the Clinical Global Impression-Improvement (CGI-I) scale see paragraph [00420] supra. The CGI-I is administered by the investigator/trained rater at time points specified in Table 6.4 and Table 6.5. The CGI-I during Periods 1 and 2 are relative to the CGI-S score at the baseline visit (visit 2 in Period 1).

The Clinical Global Impression-Severity of Illness (CGI-S) Scale is described in paragraph [00422], supra. The investigator/trained rater completes the CGI-S at the time points specified in Table 6.4 and Table 6.5.

The Patient Global Impression-Improvement (PGI-I) scale is described in paragraph [00424], supra (see time points specified in Table 6.4 and Table 6.5).

The Personal and Social Performance (PSP) Scale is administered to patients at the time points specified in Table 6.4 and Table 6.5 and is a clinician-rated instrument as described further in paragraph [00426]. Other Assessments Structured Clinical Interview for DSM-5, Clinical Trials Version (SCID-5-CT)

The SCID-5-CT is a semi-structured interview guide for making DSM-5 diagnoses. It is administered at screening by a clinician or trained mental health professional who is familiar with the DSM-5 classification and diagnostic criteria.

The SCID-5-CT can be used to ensure that the major DSM-5 diagnoses are systematically evaluated and that all study patients have symptoms that meet the DSM-5 criteria for inclusion and exclusion, and to characterize a study population in terms of current and previous psychiatric diagnoses.

The Schizophrenia Quality of Life Scale (SQLS) Revision 4 (see paragraph [00428]) is administered at the time points specified in Table 6.4 and Table 6.5 and is used to capture quality of life.

The 3-Level EuroQol Five Dimensions Questionnaire (EQ-5D-3L; see paragraph [00430]) is administered at the time points specified in Table 6.4 and Table 6.5 and is a standardized questionnaire that assesses overall state of health.

Assessment of Safety

In this study, safety is assessed by qualified study personnel by evaluating reported adverse events (including serious adverse events, extrapyramidal symptoms, injection pain and other ISRs [local tolerability]), vital signs (blood pressure, pulse and orthostatic changes, and temperature), body weight, laboratory tests, ECG, concomitant medication use, time to all-cause discontinuation, all-cause discontinuation rates and discontinuation rates due to adverse events (tolerability), and rating scales (including AIMS, BARS, SAS, C-SSRS, and CDSS).

Post-Injection Delirium/Sedation Syndrome Monitoring

Patients who are administered Formulation 1 (according to the time points in Table 6.4 and Table 6.5) will remain under clinical observation for at least 3 hours postdose to be monitored for symptoms of a potential PDSS event.

In case a potential PDSS event is suspected, the MM and sponsor should be contacted immediately. Vital signs and blood samples for plasma drug concentration and biomarkers (for patients who provided consent for biomarker collection) should be collected as soon as potential PDSS is suspected. In case a suspected PDSS event is reported, a toxicological blood test should be collected from the patient as soon as PDSS is suspected.

Additional pharmacokinetic samples are collected at 3, 6, 12, and 24 hours after the onset of the event and 24 hours after resolution, or when feasible. Additional biomarker samples should be collected 24 hours after the onset of the event and 24 hours after resolution, or when feasible. Vital signs should be measured at the same time points that additional pharmacokinetic samples are collected.

Any potential PDSS event requires evaluation by the investigator according to the criteria listed below.

If a potential PDSS event occurs, the IDMC will review the case and determine whether it meets all 5 criteria in the following definition for a clinical diagnosis of PDSS:

1. One or both of the conditions listed in (a) and (b):
   a. Minimum of 1 sign or symptom from at least 3 of the following symptom clusters consistent with olanzapine overdose, with 1 or more of at least moderate severity:
      seizure
      sedation/somnolence
      delirium/confusion/disorientation/other cognitive impairment
      dysarthria/other speech impairment
      ataxia/other motor impairment
      extrapyramidal symptoms
      agitation/irritability/anxiety/restlessness
      dizziness/weakness/general malaise
   b. Any 1 of the following signs and symptoms such that the patient is:
      unarousable, unconscious, stuporous, or comatose
2. Condition develops within 24 hours of Formulation 1 administration.
3. Condition cannot be explained by a significant dose increase (ie, overdose) of Formulation 1 or initiation or addition of oral olanzapine (or other forms of olanzapine) or other sedating medication.
4. Underlying medical conditions have been ruled out, including concomitant substance use or abuse.
5. Olanzapine plasma level is >100 ng/mL≤3 hours after injection.

Example 7

In Vitro Release in Human Plasma

A commercially available human plasma was placed in well closed Erlenmeyer flasks on an orbital shaking water bath. The temperature was maintained at 37° C. and rotation was set at 100 RPMs throughout the test. Formulation 1 and Zyprexa Relprevv® were reconstituted as per instructions for use and injected directly in human plasma. At specified time points during 72 hours, an aliquot of sample solution was withdrawn from the Erlenmeyer flasks and immediately filtered through 0.45 μm syringe filters. Sampled volume of plasma was replaced with the same volume fresh plasma, thermostated at 37° C., to keep the total plasma volume constant within the flask. Olanzapine was quantified from the collected in vitro release samples by LC-MS/MS with ESI ion source. The study shows that the risk of PDSS with Formulation 1 technology is minimized. See FIG. 10.

The invention will now be described further with reference to the following clauses:

1. A pharmaceutical composition for administration by subcutaneous injection, the composition comprising 20%-45% (w/w) of olanzapine;
   35%-65% (w/w) of an organic solvent comprising dimethyl sulfoxide, N-methyl-2-pyrrolidinone (NMP), or a combination thereof;
   a diblock copolymer comprising polylactic acid and polyethylene glycol and having a number average molecular weight of 6 to 15 kg/mol and comprising 70%-90% by weight (w/w) polylactic acid; and
   a triblock copolymer comprising polylactic acid and polyethylene glycol and having a number average molecular weight of 6 to 19 kg/mol and comprising 80%-90% by weight (w/w) polylactic acid;
   and wherein the diblock copolymer and triblock copolymer together comprise 10%-25% by weight (w/w) of the composition.
2. The pharmaceutical composition of clause 1, wherein the composition comprises 20%-24% by weight (w/w) olanzapine.
3. The pharmaceutical composition of clause 2, wherein the composition comprises 20.5% by weight (w/w) olanzapine.
4. The pharmaceutical composition of clause 2, wherein the composition comprises 22% by weight (w/w) olanzapine.
5. The pharmaceutical composition of clause 2, wherein the composition comprises 23.5% by weight (w/w) olanzapine.
6. The pharmaceutical composition of clause 1, wherein the composition comprises 22%-34% by weight (w/w) olanzapine.
7. The pharmaceutical composition of clause 6, wherein the composition comprises 30%-32% by weight (w/w) olanzapine.
8. The pharmaceutical composition of clause 6, wherein the composition comprises 26.5% by weight (w/w) olanzapine.
9. The pharmaceutical composition of clause 6, wherein the composition comprises 29.0% by weight (w/w) olanzapine.
10. The pharmaceutical composition of clause 6 or clause 7, wherein the composition comprises 30.5% by weight (w/w) olanzapine.
11. The pharmaceutical composition of clause 6 or clause 7, wherein the composition comprises 32.0% by weight (w/w) olanzapine.
12. The pharmaceutical composition of clause 6, wherein the composition comprises 33.5% by weight (w/w) olanzapine.
13. The pharmaceutical composition of clause 1, wherein the composition comprises 40%-45% by weight (w/w) olanzapine.
14. The pharmaceutical composition of clause 13, wherein the composition comprises 40.7% by weight (w/w) olanzapine.
15. The pharmaceutical composition of clause 13, wherein the composition comprises 42.0% by weight (w/w) olanzapine.
16. The pharmaceutical composition of clause 13, wherein the composition comprises 43.5% by weight (w/w) olanzapine.
17. The pharmaceutical composition of any one of the preceding clauses, wherein the organic solvent is dimethyl sulfoxide (DMSO).
18. The pharmaceutical composition of any one of clauses 1-16, wherein the organic solvent is N-methyl-2-pyrrolidinone (NMP).

19. The pharmaceutical composition of any one of clauses 1-16, wherein the organic solvent is a mixture of dimethyl sulfoxide (DMSO) and N-methyl-2-pyrrolidinone (NMP).
20. The pharmaceutical composition of any one of the preceding clauses, wherein the composition comprises 35%-40% by weight (w/w) of the organic solvent.
21. The pharmaceutical composition of clause 20, wherein the composition comprises 35% by weight (w/w) of the organic solvent.
22. The pharmaceutical composition of clause 20, wherein the composition comprises 37.1% by weight (w/w) of the organic solvent.
23. The pharmaceutical composition of clause 20, wherein the composition comprises 38% by weight (w/w) of the organic solvent.
24. The pharmaceutical composition of any one of the clauses 1-19, wherein the composition comprises 50%-55% by weight (w/w) of the organic solvent.
25. The pharmaceutical composition of clause 24, wherein the composition comprises 50% by weight (w/w) of the organic solvent.
26. The pharmaceutical composition of clause 24, wherein the composition comprises 52% by weight (w/w) of the organic solvent.
27. The pharmaceutical composition of clause 24, wherein the composition comprises 53.5% by weight (w/w) of the organic solvent.
28. The pharmaceutical composition of clause 24, wherein the composition comprises 54% by weight (w/w) of the organic solvent.
29. The pharmaceutical composition of clause 24, wherein the composition comprises 55% by weight (w/w) of the organic solvent.
30. The pharmaceutical composition of any one of the clauses 1-19, wherein the composition comprises 58%-62% by weight (w/w) of the organic solvent.
31. The pharmaceutical composition of clause 30, wherein the composition comprises 58.5% by weight (w/w) of the organic solvent.
32. The pharmaceutical composition of clause 30, wherein the composition comprises 60% by weight (w/w) of the organic solvent.
33. The pharmaceutical composition of clause 30, wherein the composition comprises 61.5% by weight (w/w) of the organic solvent.
34. The pharmaceutical composition of any one of the preceding clauses, wherein the diblock copolymer comprises 75%-84% by weight (w/w) polylactic acid.
35. The pharmaceutical composition of clause 34, wherein the diblock copolymer comprises 76% by weight (w/w) polylactic acid.
36. The pharmaceutical composition of clause 34, wherein the diblock copolymer comprises 80% by weight (w/w) polylactic acid.
37. The pharmaceutical composition of clause 34, wherein the diblock copolymer comprises 82% by weight (w/w) polylactic acid.
38. The pharmaceutical composition of any one of clauses 1-37, wherein the diblock copolymer comprises 73%-77% by weight (w/w) polylactic acid.
39. The pharmaceutical composition of clause 38, wherein the diblock copolymer comprises 73% by weight (w/w) polylactic acid.
40. The pharmaceutical composition of clause 38, wherein the diblock copolymer comprises 75% by weight (w/w) polylactic acid.
41. The pharmaceutical composition of clause 38, wherein the diblock copolymer comprises 77% by weight (w/w) polylactic acid.
42. The pharmaceutical composition of any one of clauses 1-33, wherein the diblock copolymer comprises 84% to 88% by weight (w/w) polylactic acid.
43. The pharmaceutical composition of clause 42, wherein the diblock copolymer comprises 84% by weight (w/w) polylactic acid.
44. The pharmaceutical composition of clause 42, wherein the diblock copolymer comprises 86% by weight (w/w) polylactic acid.
45. The pharmaceutical composition of clause 42, wherein the diblock copolymer comprises 88% by weight (w/w) polylactic acid.
46. The pharmaceutical composition of any one of the preceding clauses, wherein the diblock copolymer has a number average molecular weight of 6.5 to 13.5 kg/mol, optionally 7.0 to 13.5 kg/mol.
47. The pharmaceutical composition of any one of the preceding clauses, wherein the diblock copolymer has a number average molecular weight of about 9 kg/mol.
48. The pharmaceutical composition of any one of clauses 1-47, wherein the diblock copolymer has a number average molecular weight of about 10 kg/mol.
49. The pharmaceutical composition of any one of clauses 1-47, wherein the diblock copolymer has a number average molecular weight of about 11 kg/mol.
50. The pharmaceutical composition of any one of clauses 1-49, wherein the weight ratio of the diblock copolymer to the triblock copolymer is from 6:1 to 2:1, optionally about 4:1.
51. The pharmaceutical composition of any one of the preceding clauses, wherein the composition comprises 10%-17% by weight (w/w) of the diblock copolymer.
52. The pharmaceutical composition of any one of clause 51, wherein the composition comprises 10%-15% by weight (w/w) of the diblock copolymer.
53. The pharmaceutical composition of clause 51, wherein the composition comprises 12.2% by weight (w/w) of the diblock copolymer.
54. The pharmaceutical composition of clause 51, wherein the composition comprises 12.8% by weight (w/w) of the diblock copolymer.
55. The pharmaceutical composition of clause 51, wherein the composition comprises 13.2% by weight (w/w) of the diblock copolymer.
56. The pharmaceutical composition of clause 51, wherein the composition comprises 13.6% by weight (w/w) of the diblock copolymer.
57. The pharmaceutical composition of clause 51, wherein the composition comprises 14.0% by weight (w/w) of the diblock copolymer.
58. The pharmaceutical composition of clause 51, wherein the composition comprises 14.4% by weight (w/w) of the diblock copolymer.
59. The pharmaceutical composition of any one of the preceding clauses, wherein the triblock copolymer comprises 85%-88% by weight (w/w) polylactic acid.
60. The pharmaceutical composition of clause 59, wherein the triblock copolymer comprises 87% by weight (w/w) polylactic acid.
61. The pharmaceutical composition of clause 59, wherein the triblock copolymer comprises 85% by weight (w/w) polylactic acid.
62. The pharmaceutical composition of any one of the preceding clauses, wherein the triblock copolymer has a number average molecular weight of 6.0 to 13.0 kg/mol, optionally 7.0 to 12.0 kg/mol.
63. The pharmaceutical composition of any one of the preceding clauses, wherein the triblock copolymer has a number average molecular weight of about 9.5 kg/mol.
64. The pharmaceutical composition of any one of clauses 1-62, wherein the triblock copolymer has a number average molecular weight of about 14 kg/mol.
65. The pharmaceutical composition of any one of the preceding clauses, wherein the composition comprises 3%-5% by weight (w/w) of the triblock copolymer.
66. The pharmaceutical composition of any one of the preceding clauses, wherein the composition comprises 3%-4% by weight (w/w) of the triblock copolymer.
67. The pharmaceutical composition of any one of the preceding clauses, wherein the composition comprises 3.0% by weight (w/w) of the triblock copolymer.
68. The pharmaceutical composition of any one of clauses 1-66, wherein the composition comprises 3.2% by weight (w/w) of the triblock copolymer.
69. The pharmaceutical composition of any one of clauses 1-66, wherein the composition comprises 3.5% by weight (w/w) of the triblock copolymer.
70. The pharmaceutical composition of any one of clauses 1-66, wherein the composition comprises 3.6% by weight (w/w) of the triblock copolymer.
71. The pharmaceutical composition of any one of clauses 1-66, wherein the composition comprises 3.7% by weight (w/w) of the triblock copolymer.
72. The pharmaceutical composition of any one of clauses 1-65, wherein the composition comprises 4.5% by weight (w/w) of the triblock copolymer.
73. The pharmaceutical composition of any one of the preceding clauses, wherein the diblock copolymer and triblock copolymer together comprise 10 to 20% by weight (w/w), optionally 14 to 20% by weight (w/w) of the composition.
74. The pharmaceutical composition of clause 73, wherein the diblock copolymer and triblock copolymer together comprise 12% by weight (w/w) of the composition.
75. The pharmaceutical composition of clause 73, wherein the diblock copolymer and triblock copolymer together comprise 14% by weight (w/w) of the composition.
76. The pharmaceutical composition of clause 73, wherein the diblock copolymer and triblock copolymer together comprise 16% by weight (w/w) of the composition.
77. The pharmaceutical composition of clause 73, wherein the diblock copolymer and triblock copolymer together comprise 18% by weight (w/w) of the composition.
78. The pharmaceutical composition of clause 73, wherein the diblock copolymer and triblock copolymer together comprise 20% by weight (w/w) of the composition.
79. The pharmaceutical composition of any one of clauses 1-72, wherein the diblock copolymer and triblock copolymer together comprise 22% by weight (w/w) of the composition.
80. The pharmaceutical composition of any one of the preceding clauses, wherein the composition contains from about 220 mg—about 340 mg of olanzapine per gram of composition.
81. The pharmaceutical composition of any one of the preceding clauses, wherein the composition contains about 265 mg of olanzapine per gram of composition.
82. The pharmaceutical composition of any one of clauses 1-80, wherein the composition contains about 290 mg of olanzapine per gram of composition.
83. The pharmaceutical composition of any one of clauses 1-80, wherein the composition contains about 305 mg of olanzapine per gram of composition.
84. The pharmaceutical composition of any one of clauses 1-80, wherein the composition contains about 320 mg of olanzapine per gram of composition.
85. The pharmaceutical composition of any one of clauses 1-80, wherein the composition contains about 335 mg of olanzapine per gram of composition.
86. A kit comprising:
  a container containing about 318 mg—about 950 mg of olanzapine; and
  a container containing a about 0.73—about 2.5 grams of a mixture of an organic solvent that is dimethyl sulfoxide (DMSO), N-methyl-2-pyrrolidinone (NMP), or a combination thereof, a diblock copolymer comprising polylactic acid and polyethylene glycol and having a number average molecular weight of 6 to 15 kg/mol and comprises 70%-90% by weight (w/w) polylactic acid, and a triblock copolymer comprising polylactic acid and polyethylene glycol and having a number average molecular weight of 6 to 19 kg/mol and comprises 80%-90% by weight (w/w) polylactic acid.
87. The kit of clause 86, wherein the container containing olanzapine contains about 318 mg of olanzapine.
88. The kit of clause 86, wherein the container containing olanzapine contains about 575 mg of olanzapine.
89. The kit of clause 86, wherein the container containing olanzapine contains about 600 mg of olanzapine.
90. The kit of clause 86, wherein the container containing olanzapine contains about 710 mg of olanzapine.
91. The kit of clause 86, wherein the container containing olanzapine contains about 815 mg of olanzapine.
92. The kit of clause 86, wherein the container containing olanzapine contains about 885 mg of olanzapine.
93. The kit of any one of clauses 86-92, wherein the container containing the mixture of organic solvent, diblock copolymer and triblock copolymer, contains about 0.73 grams of the mixture.
94. The kit of any one of clauses 86-92, wherein the container containing the mixture of organic solvent, diblock copolymer and triblock copolymer, contains about 1.5 grams of the mixture.
95. The kit of any one of clauses 86-92, wherein the container containing the mixture of organic solvent, diblock copolymer and triblock copolymer, contains about 1.7 grams of the mixture.
96. The kit of any one of clauses 86-92, wherein the container containing the mixture of organic solvent, diblock copolymer and triblock copolymer, contains about 2.0 grams of the mixture.
97. The kit of any one of clauses 86-96, wherein the container containing olanzapine is a glass vial.
98. The kit of any one of clauses 86-97, wherein the container containing the mixture of an organic solvent, a diblock copolymer comprising polylactic acid and polyethylene glycol, and a triblock copolymer comprising polylactic acid and polyethylene glycol, is a syringe.

99. The kit of clause 98, further comprising a needle, wherein the needle is capable of being fitted to the syringe.
100. The kit of clause 99, wherein the needle is a 21 gauge needle.
101. The kit of clause 99 or clause 100, wherein the needle is ⅝ inches in length.
102. The kit of any one of clauses 86-101, for use in preparing a composition of any one of clauses 1-84.
103. A method of preparing the composition of any one of clauses 1-85, the method comprising adding a mixture of the organic solvent, the diblock copolymer comprising polylactic acid and polyethylene glycol, and the triblock copolymer comprising polylactic acid and polyethylene glycol, to solid olanzapine.
104. The method of clause 103, wherein the mixture of the organic solvent, the diblock copolymer comprising polylactic acid and polyethylene glycol, and the triblock copolymer comprising polylactic acid and polyethylene glycol is added by syringe to the solid olanzapine in a vial.
105. The kit of any one of clauses 86-102 or the method of clause 103 or 104, wherein the olanzapine has a particle size distribution characterized by a D(90) of from about 20 μm to about 37 μm, a particle size distribution characterized by a D(3,2) of from about 5.5 μm to about 7.5 μm, or a tapped density from about 0.35 g/ml to 0.44 g/ml, or any combination thereof.
106. The kit or method of clause 105 wherein the olanzapine has a particle size distribution characterized by a D(90) of from 20 μm to about 37 μm.
107. The kit or method of clause 106 wherein the olanzapine has a particle size distribution characterized by a D(90) of from about 24 μm to about 35 μm.
108. The kit or method of clause 106 wherein the olanzapine has a particle size distribution characterized by a D(3,2) of from about 5.5 μm to about 7.5 μm.
109. The kit or method of clause 106 wherein the olanzapine has a particle size distribution characterized by a D(3,2) of from about 5.8 μm to about 7.0 μm.
110. The kit or method of any one of clauses 105-109 wherein the olanzapine has a tapped density of the olanzapine is from about 0.35 g/ml to about 0.44 g/ml.
111. The kit or method of clause 105 wherein the olanzapine has a particle size distribution characterized by a D(90) of from about 20 μm to about 37 μm and by a D(3,2) of from about 5.5 μm to about 7.5 μm.
112. The kit or method of clause 105 wherein the olanzapine has a particle size distribution characterized by a D(90) of from about 20 μm to about 37 μm, and has a tapped density of about 0.35 g/ml to about 0.44 g/ml.
113. The kit or method of clause 105 wherein the olanzapine has a particle size distribution characterized by a D(3,2) of from about 5.5 μm to about 7.5 μm, and has a tapped density of about 0.35 g/ml to about 0.44 g/ml.
114. The kit or method of clause 105 wherein the olanzapine has a particle size distribution characterized by a D(90) of from about 20 μm to about 37 μm and by a D(3,2) of from about 5.5 μm to about 7.5 μm, and has a tapped density of about 0.35 g/ml to about 0.44 g/ml.
115. The kit or method of any one of clauses 86-114, wherein the olanzapine is polymorph form II.
116. A method of administering olanzapine to a patient, the method comprising subcutaneously injecting the patient with a composition of any one of clauses 1-85.
117. A method of treating a disease or disorder that is schizophrenia, schizoaffective disorder, bipolar disorder, or depression, in a patient in need thereof, the method comprising subcutaneously administering to the patient a composition of any one of clauses 1-85.
118. The method of clause 117, wherein the disease or disorder is schizophrenia.
119. The method of clause 117, wherein the disease or disorder is schizoaffective disorder.
120. The method of clause 117, wherein the disease or disorder is bipolar disorder.
121. The method of clause 117, wherein the disease or disorder is depression.
122. The method of any one of clauses 116-121, wherein the patient has a PANSS total score between 80 and 120, inclusive, at baseline (prior to randomization) with a score ≥4 on at least 2 of the following 4 items of the PANSS positive subscale: hallucinatory behavior, delusions, conceptual disorganization, or suspiciousness/persecution.
123. The method of any one of clauses 116-122, wherein the subcutaneously administered composition comprises 300 mg-600 mg of olanzapine.
124. The method of clause 123, wherein the subcutaneously administered composition comprises 300-350 mg, optionally 310-320 mg, of olanzapine.
125. The method of clause 124, wherein the subcutaneously administered composition comprises about 318 mg of olanzapine.
126. The method of clause 123, wherein the subcutaneously administered composition comprises 400-450 mg, optionally 415-435 mg, of olanzapine.
127. The method of clause 126, wherein the subcutaneously administered composition comprises about 425 mg of olanzapine.
128. The method of clause 123, wherein the subcutaneously administered composition comprises 500-550 mg, optionally 520-540 mg, of olanzapine.
129. The method of clause 128, wherein the subcutaneously administered composition comprises about 531 mg of olanzapine.
130. The method of any one of clauses 116-129, wherein the subcutaneously administered composition has a volume of about 0.5-1.8 mL.
131. The method of any one of clauses 116-130 wherein the subcutaneously administered composition has a volume of about 0.9-1.5 mL.
132. The method of clause 131, wherein the composition has a volume of about 0.9 mL.
133. The method of clause 131, wherein the composition has a volume of about 1.2 mL.
134. The method of clause 131, wherein the composition has a volume of about 1.5 mL.
135. The method of any one of clauses 116-134, wherein the composition is administered once per month.
136. The method of any one of clauses 116-135, wherein the composition is administered once per 28±5 days.
137. The method of any one of clauses 116-136, wherein the composition is administered once per 28±3 days.
138. The method of any one of clauses 116-137, wherein the composition is administered once per 28 days.
139. The method of any one of clauses 116-138, wherein the dose-normalized ratio of $AUC_\infty$, after a single subcutaneous dose of the composition to the $AUC_{tau}$ of oral olanzapine calculated for 28 days is between 0.97-1.29.
140. The method of any one of clauses 116-139, wherein the dose-normalized ratio of $AUC_\infty$ after a single subcutaneous dose of the composition to the $AUC_{tau}$ of oral olanzapine calculated for 28 days is about 1.1.

141. The method of any one of clauses 116-140, wherein administration of the composition to the patient by subcutaneous injection results in the patient having an olanzapine plasma $C_{max}$ within 11-14 days after the administration.

142. The method of any one of clauses 116-141, wherein administration of the composition to a patient by subcutaneous injection results in the patient having an olanzapine plasma $C_{max}$ of less than 100 ng/mL after the first subcutaneous injection.

143. The method of any one of clauses 116-142, wherein administration of the composition to a patient by subcutaneous injection results in the patient having an olanzapine plasma $C_{max}$ of less than 100 ng/mL after the second subcutaneous injection.

144. The method of any one of clauses 116-143, wherein administration of the composition to a patient by subcutaneous injection results in the patient having an olanzapine plasma $C_{max}$ of less than 90 ng/mL after the first subcutaneous injection.

145. The method of any one of clauses 116-144, wherein administration of the composition to a patient by subcutaneous injection results in the patient having an olanzapine plasma $C_{max}$ of less than 90 ng/mL after the second subcutaneous injection.

146. The method of any one of clauses 116-145, wherein administration of the composition to a patient by subcutaneous injection results in the patient having an olanzapine plasma $C_{max}$ of less than 80 ng/mL after the first subcutaneous injection.

147. The method of any one of clauses 115-146, wherein administration of the composition to a patient by subcutaneous injection results in the patient having an olanzapine plasma $C_{max}$ of less than 80 ng/mL after the second subcutaneous injection.

148. The method of any one of clauses 116-147, wherein administration of the composition to a patient by subcutaneous injection results in the patient having an olanzapine plasma $C_{max}$ of less than 70 ng/mL after the first subcutaneous injection.

149. The method of any one of clauses 116-148, wherein administration of the composition to a patient by subcutaneous injection results in the patient having an olanzapine plasma $C_{max}$ of less than 70 ng/mL after the second subcutaneous injection.

150. The method of any one of clauses 116-149, wherein administration of the composition to a patient by subcutaneous injection results in the patient having an olanzapine plasma $C_{max}$ of less than 60 ng/mL after the first subcutaneous injection.

151. The method of any one of clauses 116-150, wherein administration of the composition to a patient by subcutaneous injection results in the patient having an olanzapine plasma $C_{max}$ of less than 60 ng/mL after the second subcutaneous injection.

152. The method of any one of clauses 116-151, wherein administration of the composition to a patient by subcutaneous injection results in the patient having an olanzapine plasma $C_{max}$ of less than 50 ng/mL after the first subcutaneous injection.

153. The method of any one of clauses 116-152, wherein administration of the composition to a patient by subcutaneous injection results in the patient having an olanzapine plasma $C_{max}$ of less than 50 ng/mL after the second subcutaneous injection.

154. The method of any one of clauses 116-153, wherein administration of the composition to a patient by subcutaneous injection results in the patient having an olanzapine plasma $C_{max}$ of less than 40 ng/mL after the first subcutaneous injection.

155. The method of any one of clauses 116-154, wherein administration of the composition to a patient by subcutaneous injection results in the patient having an olanzapine plasma $C_{max}$ of less than 40 ng/mL after the second subcutaneous injection.

156. The method of any one of clauses 116-155, wherein administration of the composition to a patient by subcutaneous injection results in the patient having an olanzapine plasma concentration of at least 10 ng/mL for at least 21 days of the 30 days following the subcutaneous injection.

157. The method of any one of clauses 116-156, wherein administration of the composition to a patient by subcutaneous injection results in the patient having an olanzapine plasma concentration of at least 20 ng/mL for at least 21 days of the 30 days following the subcutaneous injection.

158. The method of any one of clauses 116-157, wherein administration of the composition to a patient by subcutaneous injection results in the patient having an olanzapine plasma concentration of at least 10 ng/mL for at least 30 days following the subcutaneous injection.

159. The method of any one of clauses 116-158, wherein administration of the composition to a patient by subcutaneous injection results in the patient having an olanzapine plasma concentration of at least 20 ng/mL for at least 30 days following the subcutaneous injection.

160. A method of treating a patient with olanzapine comprising
a) providing the kit of any one of clauses 86-102 or 105-115;
b) withdrawing the mixture of organic solvent, diblock copolymer, and triblock copolymer from the container in the kit containing said mixture;
c) adding the mixture from b) to the container in the kit containing olanzapine and then mixing, to form a subcutaneous olanzapine pharmaceutical composition; and
d) subcutaneously administering the subcutaneous olanazpine pharmaceutical composition to the patient in need of olanzapine treatment; wherein the treatment is effective for about one month.

161. The method of any one of clauses 116-160, wherein the treatment results in the patient having a lower score on the Positive and Negative Syndrome Scale (PANSS) than the patient had prior to receiving the treatment.

162. The method of any one of clauses 116-161, wherein the treatment results in the patient having a lower score on the Clinical Global Impression-Improvement (CGI-I) scale than the patient had prior to receiving the treatment.

163. The method of any one of clauses 116-162, wherein the treatment results in the patient having a lower score on the Clinical Global Impression—Severity of Illness Scale (CGI-S) scale than the patient had prior to receiving the treatment.

164. The method of any one of clauses 116-163, wherein the treatment results in the patient having a lower score on the Patient Global Impression-Improvement (PGI-I) than the patient had prior to receiving the treatment.

165. The method of any one of clauses 116-164, wherein treatment results in the patient having a higher score on the Personal and Social Performance Scale (PSP) than the patient had prior to receiving the treatment.

166. The method of any one of clauses 116-165, wherein the treatment results in the patient having a lower score on the Schizophrenia Quality of Life Scale (SQLS) Revision 4 than the patient had prior to receiving the treatment.

167. The method of any one of clauses 116-166, wherein the treatment results in the patient having a lower score on the 3-Level EuroQol Five Dimensions Questionnaire (EQ-5D-3L) than the patient had prior to receiving the treatment.

168. The method of any one of clauses 116-167, wherein the treatment results in the patient having a $D_2$-receptor occupancy of 60-80%, optionally 65-80%, optionally 65-70%, as determined by positron emission tomography (PET).

169. A method of switching a patient from a daily oral olanzapine therapy to a therapy comprising once per month administration of the composition of any one of clauses 1-85, the method comprising i) orally administering a final administration of the daily oral olanzapine therapy, after which no further oral olanzapine therapy is administered; and the next day subcutaneously administering to the patient a composition of any one of clauses 1-85; thereby switching the subject from a daily oral olanzapine therapy to a therapy comprising administration of the composition of any one of clauses 1-84.

170. A method of switching a patient from a long acting intramuscular injectable olanzapine formulation to a composition of any one of clauses 1-85, without the need for supplemental oral olanzapine therapy, wherein the method comprises administering a final dose of the long acting intramuscularly injectable olanzapine formulation; and at the next dosing, optionally one month after the preceding dose when the preceding dose is a once monthly dose, or optionally two weeks after the preceding dose when the preceding dose is a once every two-weeks dose, subcutaneously administering a composition of any one of clauses 1-85; wherein the method is performed without administering to the patient a supplemental oral olanzapine therapy.

171. A pharmaceutical composition as defined in any one of clauses 1-85 for use in medicine.

172. A pharmaceutical composition as defined in any one of clauses 1-85 for use in a method as defined in any of clauses 116-170.

173. A method of treating an olanzapine naïve patient, comprising administering to the patient an oral daily dose of 10 mg-20 mg olanzapine for 2 consecutive days to assess the patient's tolerance of olanzapine, and if the patient tolerates the oral olanzapine, then subcutaneously administering a pharmaceutical composition of any one of clauses 1-86.

What is claimed:

1. A method of treating schizophrenia in a patient in need thereof, the method comprising subcutaneously administering to the abdomen or upper arm of the patient, once per 28±5 days, 0.9-1.5 mL of a pharmaceutical composition comprising 305 mg of olanzapine per gram of composition, wherein the composition comprises:
   30%-32% (w/w) of olanzapine;
   52%-54% (w/w) of dimethyl sulfoxide;
   12%-14% (w/w) of a diblock copolymer comprising polylactic acid and polyethylene glycol and having a number average molecular weight of 6.5 to 12.5 kg/mol and comprising 75%-84% by weight (w/w) polylactic acid; and
   3%-3.5% (w/w) of a triblock copolymer comprising polylactic acid and polyethylene glycol and having a number average molecular weight of 6 to 13 kg/mol and comprising 83%-88% by weight (w/w) polylactic acid;
   and wherein the diblock copolymer and triblock copolymer together comprise 15%-17.5% by weight (w/w) of the composition;
   wherein the administration of the composition to the patient by subcutaneous injection results in
   the patient having an olanzapine plasma $C_{max}$ within 11-14 days after the administration;
   an olanzapine plasma $C_{max}$ of less than 100 ng/mL after any subcutaneous injection administered in the method;
   a dose-normalized ratio of AUC∞ after any subcutaneous dose of the composition to the AUCtau of oral olanzapine calculated for 28 days is between 0.97-1.29; and
   an olanzapine plasma concentration of at least 10 ng/ml for at least 21 days of the 30 days following any of the subcutaneous injections.

2. The method of claim 1, wherein 0.9 mL of the pharmaceutical composition is subcutaneously administered.

3. The method of claim 1, wherein 1.2 mL of the pharmaceutical composition is subcutaneously administered.

4. The method of claim 1, wherein 1.5 mL of the pharmaceutical composition is subcutaneously administered.

5. The method of claim 1, wherein the pharmaceutical composition is administered once per month.

6. The method of claim 1, wherein the pharmaceutical composition is administered once per 28±3 days.

7. The method of claim 1, wherein the pharmaceutical composition is administered once per 28 days.

8. The method of claim 1, wherein administration of the pharmaceutical composition to the patient by subcutaneous injection results in the patient having an olanzapine plasma $C_{max}$ of less than 100 ng/ml after the first subcutaneous injection.

9. The method of claim 1, wherein administration of the pharmaceutical composition to the patient by subcutaneous injection results in the patient having an olanzapine plasma $C_{max}$ of less than 90 ng/mL after the first subcutaneous injection.

10. The method of claim 1, wherein administration of the pharmaceutical composition to the patient by subcutaneous injection results in the patient having an olanzapine plasma $C_{max}$ of less than 80 ng/ml after the first subcutaneous injection.

11. The method of claim 1, wherein administration of the pharmaceutical composition to the patient by subcutaneous injection results in the patient having an olanzapine plasma $C_{max}$ of less than 70 ng/ml after the first subcutaneous injection.

12. The method of claim 1, wherein administration of the pharmaceutical composition to the patient by subcutaneous injection results in the patient having an olanzapine plasma $C_{max}$ of less than 60 ng/ml after the first subcutaneous injection.

13. The method of claim 1, wherein administration of the pharmaceutical composition to the patient by subcutaneous injection results in the patient having an olanzapine plasma $C_{max}$ of less than 50 ng/mL after the first subcutaneous injection.

14. The method of claim 1, wherein administration of the pharmaceutical composition to the patient by subcutaneous injection results in the patient having an olanzapine plasma $C_{max}$ of less than 40 ng/ml after the first subcutaneous injection.

15. The method of claim 1, wherein administration of the pharmaceutical composition to the patient by subcutaneous injection results in the patient having an olanzapine plasma $C_{max}$ of less than 100 ng/ml after the second subcutaneous injection.

16. The method of claim 1, wherein administration of the pharmaceutical composition to the patient by subcutaneous injection results in the patient having an olanzapine plasma $C_{max}$ of less than 90 ng/ml after the second subcutaneous injection.

17. The method of claim 1, wherein administration of the pharmaceutical composition to the patient by subcutaneous injection results in the patient having an olanzapine plasma $C_{max}$ of less than 80 ng/mL after the second subcutaneous injection.

18. The method of claim 1, wherein administration of the pharmaceutical composition to the patient by subcutaneous injection results in the patient having an olanzapine plasma $C_{max}$ of less than 70 ng/ml after the second subcutaneous injection.

19. The method of claim 1, wherein administration of the pharmaceutical composition to the patient by subcutaneous injection results in the patient having an olanzapine plasma $C_{max}$ of less than 60 ng/mL after the second subcutaneous injection.

20. The method of claim 1, wherein administration of the pharmaceutical composition to the patient by subcutaneous injection results in the patient having an olanzapine plasma $C_{max}$ of less than 50 ng/ml after the second subcutaneous injection.

21. The method of claim 1, wherein administration of the pharmaceutical composition to the patient by subcutaneous injection results in the patient having an olanzapine plasma $C_{max}$ of less than 40 ng/ml after the second subcutaneous injection.

22. The method of claim 1, wherein administration of the pharmaceutical composition to a patient by subcutaneous injection results in the patient having an olanzapine plasma concentration of at least 20 ng/ml for at least 21 days of the 30 days following the subcutaneous injection.

23. The method of claim 1, wherein administration of the pharmaceutical composition to a patient by subcutaneous injection results in the patient having an olanzapine plasma concentration of at least 10 ng/ml for at least 30 days following the subcutaneous injection.

24. The method of claim 1, wherein administration of the pharmaceutical composition to a patient by subcutaneous injection results in the patient having an olanzapine plasma concentration of at least 20 ng/ml for at least 30 days following the subcutaneous injection.

\* \* \* \* \*